2016.

United States Patent
Wittrup et al.

(10) Patent No.: US 9,464,136 B2
(45) Date of Patent: Oct. 11, 2016

(54) ANTIBODY-BASED CONSTRUCTS DIRECTED AGAINST TYROSINE KINASE RECEPTORS

(75) Inventors: Karl Dane Wittrup, Chestnut Hill, MA (US); Jamie B. Spangler, Palo Alto, CA (US); Benjamin E. Epstein, Berkeley, CA (US); Brian L. Ross, Baltimore, MD (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/817,525

(22) PCT Filed: Aug. 20, 2011

(86) PCT No.: PCT/US2011/048529
§ 371 (c)(1),
(2), (4) Date: Apr. 29, 2013

(87) PCT Pub. No.: WO2012/024659
PCT Pub. Date: Feb. 23, 2012

(65) Prior Publication Data
US 2013/0216543 A1 Aug. 22, 2013

Related U.S. Application Data

(60) Provisional application No. 61/375,765, filed on Aug. 20, 2010.

(51) Int. Cl.
*C07K 16/28* (2006.01)
*A61K 39/395* (2006.01)

(52) U.S. Cl.
CPC ....... *C07K 16/2863* (2013.01); *C07K 2317/31* (2013.01); *C07K 2317/35* (2013.01); *C07K 2317/60* (2013.01); *C07K 2317/76* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,943,533 A | 7/1990 | Mendelsohn et al. | |
| 5,558,864 A | 9/1996 | Bendig et al. | |
| 6,165,464 A | 12/2000 | Hudziak et al. | |
| 6,217,866 B1 | 4/2001 | Schlessinger et al. | |
| 6,235,883 B1 | 5/2001 | Jakobovits et al. | |
| 7,122,646 B2 | 10/2006 | Holliger et al. | |
| 7,226,592 B2 * | 6/2007 | Kreysch | 424/136.1 |
| 7,767,792 B2 | 8/2010 | Johns et al. | |
| 8,124,085 B2 * | 2/2012 | Nielsen et al. | 424/136.1 |
| 2005/0186203 A1 | 8/2005 | Singh et al. | |
| 2009/0010840 A1 | 1/2009 | Adams et al. | |
| 2011/0064653 A1 | 3/2011 | Hansen et al. | |
| 2012/0270797 A1 * | 10/2012 | Wittrup et al. | 514/19.3 |

FOREIGN PATENT DOCUMENTS

WO 2006/066340 A1 6/2006
WO 2011/020033 A2 2/2011

OTHER PUBLICATIONS

Vajdos et al., Comprehensive functional maps of the antigen-binding site of an anti-ErbB2 antibody obtained with shotgun scanning mutagenesis. J. Mol. Biol. 320:415-428, 2002.*
Bonner, James A. et al., "Radiotherapy plus Cetuximab for Squamous-Cell Carcinoma of the Head and Neck," The New England Journal of Medicine, vol. 354:567-578 (2006).
Ciardiello, Fortunato et al., "Antitumor Activity of Sequential Treatment with Topotecan and Anti-Epidermal Growth Factor Receptor Monoclonal Antibody C225," Clinical Cancer Research, vol. 5:909-916 (1999).
Cohenuram, Michael et al., "Panitumumab the first fully human monoclonal antibody: from the bench to the clinic," Anti-Cancer Drugs, vol. 18:7-15 (2007).
Crombet, Tania et al., "Use of the Humanized Anti-Epidermal Growth Factor Receptor Monoclonal Antibody h-R3 in Combination With Radiotherapy in the Treatment of Locally Advanced Head and Neck Cancer Patients," Journal of Clinical Oncology, vol. 22(9):1646-1654 (2004).
Cunningham, David et al., "Cetuximab Monotherapy and Cetuximab plus Irinotecan in Irinotecan-Refractory Metastatic Colorectal Cancer," The New England Journal of Medicine, vol. 351:337-345 (2004).
De Bono, Johann S. et al., "Therapeutics targeting signal transduction for patients with colorectal carcinoma," British Medical Bulletin, vol. 64:227-254 (2002).
Ennis, Bruce W. et al., "The EGF Receptor System as a Target for Antitumor Therapy," Cancer Investigation, vol. 9 (5):553-562 (1991).
Friedman, Lilach M. et al., "Synergistic down-regulation of receptor tyrosine kinases by combinations of mAbs: Implications for cancer immunotherapy," PNAS, vol. 102(6):1915-1920 (2005).
Garrett, Thomas P.J. et al., "Antibodies specifically targeting a locally misfolded region of tumor associated EGFR," PNAS, vol. 106(13):5082-5087 (2009).
Grunwald, Viktor et al., "Developing Inhibitors of the Epidermal Growth Factor Receptor for Cancer Treatment," Journal of the National Cancer Institute, vol. 95(12):851-867 (2003).
Johns, Terrance G. et al., "Novel Monoclonal Antibody Specific for the DE2-7 Epidermal Growth Factor Receptor (EGFR) that also Recognizes teh EGFR Expressed in Cells Containing Amplification of the EGFR Gene," Int. J. Cancer, vol. 98:398-408 (2002).
Lee, Jeffrey C. et al., "Epidermal Growth Factor Receptor Activation in Glioblastoma through Novel Missense Mutations in the Extracellular Domain," PLoS Medicine, vol. 3(12):e485, pp. 2264-2273 (2006).

(Continued)

*Primary Examiner* — Ruixiang Li
(74) *Attorney, Agent, or Firm* — Nelson Mullins Riley & Scarborough LLP; Amy E. Mandragouras, Esq.; Ariana D. Harris

(57) ABSTRACT

The present invention features antibody-based constructs that include a combination of two or more of a tetrameric antibody, a single chain antibody, a diabody, a triabody, another immunoglobulin-based moiety, as described herein, or biologically active variants thereof.

9 Claims, 21 Drawing Sheets

(56) References Cited

OTHER PUBLICATIONS

Li, Shiqing et al., "Structural basis for inhibition of the epidermal growth factor receptor by cetuximab," Cancer Cell, vol. 7:301-311 (2005).
Martinelli, E. et al., "Anti-epidermal growth factor receptor monoclonal antibodies in cancer therapy," Clinical and Experimental Immunology, vol. 158:1-9 (2009).
Mateo, Cristina et al., "Humanization of a mouse monoclonal antibody that blocks the epidermal growth factor receptor: recovery of antagonistic activity," Immunotechnology, vol. 3:71-81 (1997).
Messersmith, Wells A. et al., "Panitumumab, a Monoclonal Anti-Epidermal Growth Factor Receptor Antibody in Colorectal Cancer: Another One or the One?" Clin. Cancer Res., vol. 13(16):4664-4666 (2007).
Nicholson, R.I. et al., "EGFR and cancer prognosis," European Journal of Cancer, vol. 37:S9-S15 (2001).
Pedersen, M.W. et al., "The type III epidermal growth factor receptor mutation, Biological significance and potential target for anti-cancer therapy," Annals of Oncology, vol. 12:745-760 (2001).
Prewett, Marie C. et al., "Enhanced Antitumor Activity of Anti-epidermal Growth Factor Receptor Monoclonal Antibody IMC-C225 in Combination with Irinotecan (CPT-11) against Human Colorectal Tumor Xenografts," Clinical Cancer Research, vol. 8:994-1003 (2002).
Sebastian, Sinto et al., "The complexity of targeting EGFR signalling in cancer: From expression to turnover," Biochimica et Biophysica Acta, vol. 1766:120-139 (2006).
Sharma, Sreenath V. et al., "Epidermal growth factor receptor mutations in lung cancer," Nature Reviews Cancer, vol. 7:169-181 (2007).
Spangler, Jamie B. et al., "Combination antibody treatment downregulates epidermal growth factor by inhibiting endosomal recycling," PNAS, vol. 107(30):13252-13257 (2010).
Tateishi, Masahiro et al., "Immunohistochemical Evidence of Autocrine Growth Factors in Adenocarcinoma of the Human Lung," Cancer Research, vol. 50:7077-7080 (1990).
Van Cutsem, Eric et al., "Open-Label Phase III Trial of Panitumumab Plus Best Supportive Care Compared With Best Supportive Care Alone in Patients With Chemotherapy-Refractory Metastatic Colorectal Cancer," Journal of Clinical Oncology, vol. 25(13):1658-1664 (2007).
Yarden, Yosef et al., "Untangling the ErbB Signalling Network," Nature Reviews Molecular Cell Biology, vol. 2:127-137 (2001).
Ben-Kasus T, Schechter B, Lavi S, Yarden Y, Sela M. Persistent elimination of ErbB-2/HER2-overexpressing tumors using combinations of monoclonal antibodies: relevance of receptor endocytosis. Proc Natl Acad Sci U S A 2009;106 (9):3294-9.
Chao G, Cochran JR, Wittrup KD. Fine epitope mapping of anti-epidermal growth factor receptor antibodies through random mutagenesis and yeast surface display. J Mol Biol 2004;342(2):539-50.
Cochran JR. Engineered proteins pull double duty. Sci Transl Med 2010;2(17):17ps5.
Cohenuram M, Saif MW. Panitumumab the first fully human monoclonal antibody: from the bench to the clinic. Anticancer Drugs 2007;18(1):7-15.
Cunningham D, Humblet Y, Siena S, Khayat D, Bleiberg H, Santoro A, et al. Cetuximab monotherapy and cetuximab plus irinotecan in irinotecan-refractory metastatic colorectal cancer. N Engl J Med 2004;351(4):337-45.
Earp HS, 3rd, Calvo BF, Sartor CI. The EGF receptor family—multiple roles in proliferation, differentiation, and neoplasia with an emphasis on HER4. Trans Am Clin Climatol Assoc 2003;114:315-33; discussion 33-4.
Ekstrand AJ, James CD, Cavenee WK, Seliger B, Pettersson RF, Collins VP. Genes for epidermal growth factor receptor, transforming growth factor alpha, and epidermal growth factor and their expression in human gliomas in vivo. Cancer Res 1991;51(8):2164-72.
Ekstrand AJ, Sugawa N, James CD, Collins VP. Amplified and rearranged epidermal growth factor receptor genes in human glioblastomas reveal deletions of sequences encoding portions of the N- and/or C-terminal tails. Proc Natl Acad Sci U S A 1992;89(10):4309-13.
Friedman LM, Rinon A, Schechter B, Lyass L, Lavi S, Bacus SS, et al. Synergistic down-regulation of receptor tyrosine kinases by combinations of mAbs: implications for cancer immunotherapy. Proc Natl Acad Sci U S A 2005;102 (6):1915-20.
Gan HK, Burgess AW, Clayton AH, Scott AM. Targeting of a conformationally exposed, tumor-specific epitope of EGFR as a strategy for cancer therapy. Cancer Res 2012;72(12):2924-30.
Garrett TP, Burgess AW, Gan HK, Luwor RB, Cartwright G, Walker F, et al. Antibodies specifically targeting a locally misfolded region of tumor associated EGFR. Proc Natl Acad Sci U S A 2009;106(13):5082-7.
Grunwald V, Hidalgo M. Developing inhibitors of the epidermal growth factor receptor for cancer treatment. J Natl Cancer Inst 2003;95(12):851-67.
Herbst RS, Kim ES, Harari PM. IMC-C225, an anti-epidermal growth factor receptor monoclonal antibody, for treatment of head and neck cancer. Expert Opin Biol Ther 2001;1(4):719-32.
Huang HS, Nagane M, Klingbeil CK, Lin H, Nishikawa R, Ji XD, et al. The enhanced tumorigenic activity of a mutant epidermal growth factor receptor common in human cancers is mediated by threshold levels of constitutive tyrosine phosphorylation and unattenuated signaling. J Biol Chem 1997;272(5):2927-35.
Huang PH, Mukasa A, Bonavia R, Flynn RA, Brewer ZE, Cavenee WK, et al. Quantitative analysis of EGFRvIII cellular signaling networks reveals a combinatorial therapeutic strategy for glioblastoma. Proc Natl Acad Sci U S A 2007;104 (31):12867-72.
Johns TG, Adams TE, Cochran JR, Hall NE, Hoyne PA, Olsen MJ, et al. Identification of the epitope for the epidermal growth factor receptor-specific monoclonal antibody 806 reveals that it preferentially recognizes an untethered form of the receptor. J Biol Chem 2004;279(29):30375-84.
Johns TG, Stocked E, Ritter G, Jungbluth AA, Huang HJ, Cavenee WK, et al. Novel monoclonal antibody specific for the de2-7 epidermal growth factor receptor (EGFR) that also recognizes the EGFR expressed in cells containing amplification of the EGFR gene. Int J Cancer 2002;98(3):398-408.
Kamat V, Donaldson JM, Kari C, Quadros MR, Lelkes PI, Chaiken I, et al. Enhanced EGFR inhibition and distinct epitope recognition by EGFR antagonistic mAbs C225 and 425. Cancer Biol Ther 2008;7(5):726-33.
Kontermann, R. et al., Dual Targeting Strategies with Bispecific Antibodies, MABS, 2012, 4:2, 187-197, DOI:10.4161/mabs.4.2.19000.
Li S, Schmitz KR, Jeffrey PD, Wiltzius JJ, Kussie P, Ferguson KM. Structural basis for inhibition of the epidermal growth factor receptor by cetuximab. Cancer Cell 2005;7(4):301-11.
Liu L, Backlund LM, Nilsson BR, Grander D, Ichimura K, Goike HM, et al. Clinical significance of EGFR amplification and the aberrant EGFRvIII transcript in conventionally treated astrocytic gliomas. J Mol Med 2005;83(11):917-26.
Lynch TJ, Bell DW, Sordella R, Gurubhagavatula S, Okimoto RA, Brannigan BW, et al. Activating mutations in the epidermal growth factor receptor underlying responsiveness of non-small-cell lung cancer to gefitinib. N Engl J Med 2004;350(21):2129-39.
Martinelli E, De Palma R, Orditura M, De Vita F, Ciardiello F. Anti-epidermal growth factor receptor monoclonal antibodies in cancer therapy. Clin Exp Immunol 2009;158(1):1-9.
Muller D, Kontermann RE. Bispecific antibodies for cancer immunotherapy: Current perspectives. BioDrugs 2010;24(2):89-98.
Nicholson RI, Gee JM, Harper ME. EGFR and cancer prognosis. Eur J Cancer 2001;37 Suppl 4:S9-15.
Orcutt KD, Ackerman ME, Cieslewicz M, Quiroz E, Slusarczyk AL, Frangioni JV, et al. A modular IgG-scFv bispecific antibody topology. Protein engineering, design & selection : PEDS 2010;23(4):221-8.
Paez JG, Janne PA, Lee JC, Tracy S, Greulich H, Gabriel S, et al. EGFR mutations in lung cancer: correlation with clinical response to gefitinib therapy. Science 2004;304(5676):1497-500.

(56) References Cited

OTHER PUBLICATIONS

Pao W, Miller V, Zakowski M, Doherty J, Politi K, Sarkaria I, et al. EGF receptor gene mutations are common in lung cancers from "never smokers" and are associated with sensitivity of tumors to gefitinib and erlotinib. Proc Natl Acad Sci U S A 2004;101(36):13306-11.

Pedersen MW, Jacobsen HJ, Koefoed K, Hey A, Pyke C, Haurum JS, et al. Sym004: a novel synergistic anti-epidermal growth factor receptor antibody mixture with superior anticancer efficacy. Cancer Res 2010;70(2):588-97.

Perera RM, Narita Y, Furnari FB, Gan HK, Murone C, Ahlkvist M, et al. Treatment of human tumor xenografts with monoclonal antibody 806 in combination with a prototypical epidermal growth factor receptor-specific antibody generates enhanced antitumor activity. Clin Cancer Res 2005;11(17):6390-9.

Roovers RC, Vosjan MJ, Laeremans T, El Khoulati R, de Bruin RC, Ferguson KM, et al. A bi-paratopic anti-EGFR nanobody efficiently inhibits solid tumour growth. Int J Cancer 2011.

Sato JD, Kawamoto T, Le AD, Mendelsohn J, Polikoff J, Sato GH. Biological effects in vitro of monoclonal antibodies to human epidermal growth factor receptors. Mol Biol Med 1983;1(5):511-29.

Scott AM, Lee FT, Tebbutt N, Herbertson R, Gill SS, Liu Z, et al. A phase I clinical trial with monoclonal antibody ch806 targeting transitional state and mutant epidermal growth factor receptors. Proc Natl Acad Sci U S A 2007;104 (10):4071-6.

Simister NE, Mostov KE. An Fc receptor structurally related to MHC class I antigens. Nature 1989;337(6203):184-7.

Sordella R, Bell DW, Haber DA, Settleman J. Gefitinib-sensitizing EGFR mutations in lung cancer activate anti-apoptotic pathways. Science 2004;305(5687):1163-7.

Spangler JB, Manzari MT, Rosalia EK, Chen TF, Wittrup KD. Triepitopic antibody fusions inhibit cetuximab-resistant BRAF and KRAS mutant tumors via EGFR signal repression. J Mol Biol 2012;422(4):532-44.

Spangler JB, Neil JR, Abramovitch S, Yarden Y, White FM, Lauffenburger DA, et al. Combination antibody treatment down-regulates epidermal growth factor receptor by inhibiting endosomal recycling. Proc Natl Acad Sci U S A 2010;107(30):13252-7.

Tateishi M, Ishida T, Mitsudomi T, Kaneko S, Sugimachi K. Immunohistochemical evidence of autocrine growth factors in adenocarcinoma of the human lung. Cancer Res 1990;50(21):7077-80.

Tracy S, Mukohara T, Hansen M, Meyerson M, Johnson BE, Janne PA. Gefitinib induces apoptosis in the EGFRL858R non-small-cell lung cancer cell line H3255. Cancer Res 2004;64(20):7241-4.

Van Cutsem E, Peeters M, Siena S, Humblet Y, Hendlisz A, Neyns B, et al. Open-label phase III trial of panitumumab plus best supportive care compared with best supportive care alone in patients with chemotherapy-refractory metastatic colorectal cancer. J Clin Oncol 2007;25(13):1658-64.

Wong AJ, Ruppert JM, Bigner SH, Grzeschik CH, Humphrey PA, Bigner DS, et al. Structural alterations of the epidermal growth factor receptor gene in human gliomas. Proc Natl Acad Sci U S A 1992;89(7):2965-9.

Yang XD, Jia XC, Corvalan JR, Wang P, Davis CG. Development of ABX-EGF, fully human anti-EGF receptor monoclonal antibody, for cancer therapy. Crit Rev Oncol Hematol 2001;38(1):17-23.

Hirai, T. et al., "Clinical results of transhiatal esophagectomy for carcinoma of the lower thoracic esophagus according to biological markers," Diseases of the Esophagus, vol. 11(4), pp. 221-225 (1998).

Muller, D. et al., "Recombinant bispecific antibodies for cellular cancer immunotherapy," Current Opinion in Molecular Therapy, vol. 9(4), pp. 319-326 (2006).

* cited by examiner

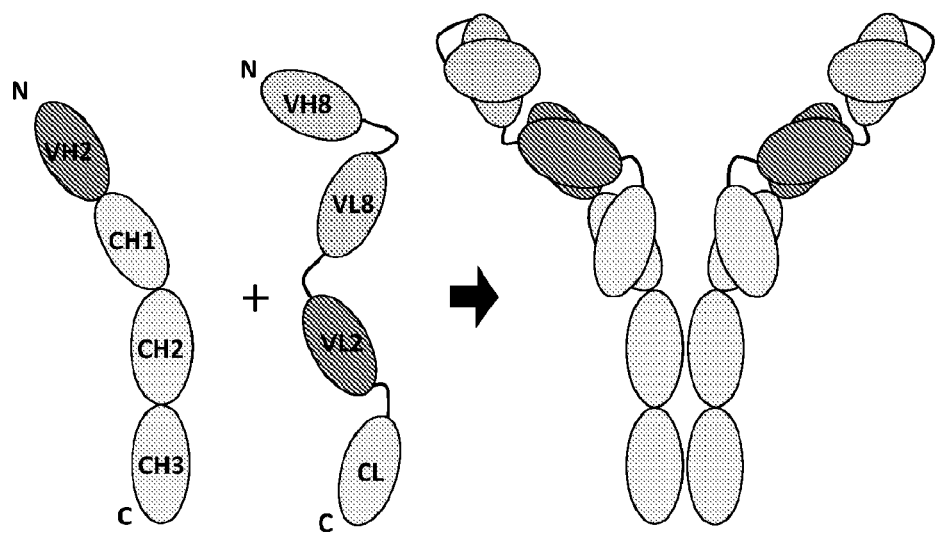
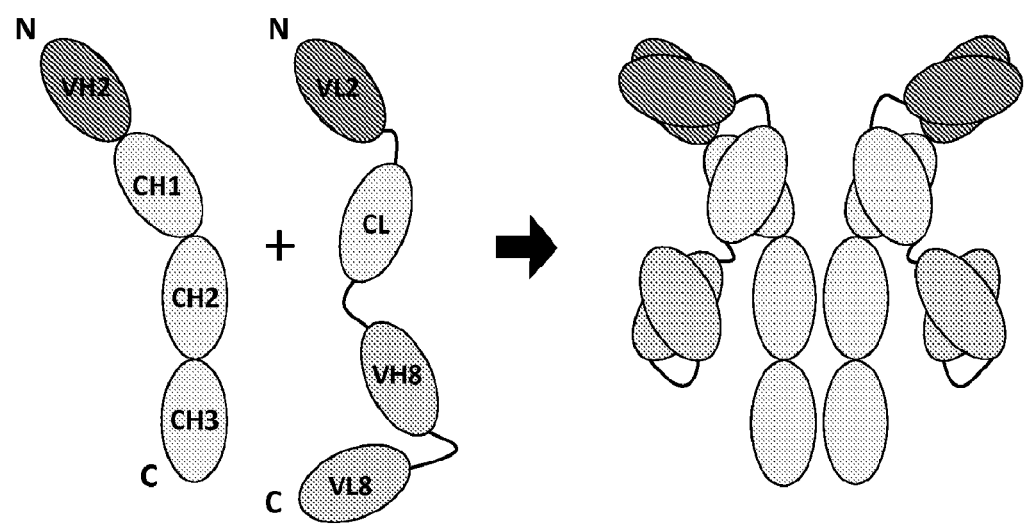
Figure 1 (Continued)

Ab-Fn3 Fusion Sequences

Abbreviations: HC=Heavy Chain; LC=Light Chain; VH=Heavy Chain Variable Domain; VL=Light Chain Variable Domain gWiz BS28-HN

PstI -- Kozak Sequence -- *Leader* -- NdeI -- NheI -- 806 VH -- (Gly4Ser)3 linker -- 806 VL -- BamHI -- (Gly4Ser)3 Linker -- MluI -- 225HC -- NheI -- CH1,2,3 -- *Stop* -- SalI

```
TCGCGCGTTTCGGTGATGACGGTGAAAACCTCTGACACATGCAGCTCCCGGAGACGGTCACAGC
TTGTCTGTAAGCGGATGCCGGGAGCAGACAAGCCCGTCAGGGCGCGTCAGCGGGTGTTGGCGGG
TTCGGGGCTGGCTTAACTATGCGGCATCAGAGCAGATTGTACTGAGAGTGCACCATATGCGGTG
TGAAATACCGCACAGATGCGTAAGGAGAAAATACCGCATCAGATTGGCTATTGGCCATTGCATA
CGTTGTATCCATATCATAATATGTACATTTATATTGGCTCATGTCCAACATTACCGCCATGTTG
ACATTGATTATTGACTAGTTATTAATAGTAATCAATTACGGGTCATTAGTTCATAGCCCATAT
ATGGAGTTCCGCGTTACATAACTTACGGTAAATGGCCCGCCTGGCTGACCGCCAACGACCCCC
GCCCATTGACGTCAATAATGACGTATGTTCCCATAGTAACGCCAATAGGGACTTTCCATTGACG
TCAATGGGTGGAGTATTTACGGTAAACTGCCCACTTGGCAGTACATCAAGTGTATCATATGCCA
AGTACGCCCCCTATTGACGTCAATGACGGTAAATGGCCCGCCTGGCATTATGCCCAGTACATGA
CCTTATGGGACTTTCCTACTTGGCAGTACATCTACGTATTAGTCATCGCTATTACCATGGTGAT
GCGGTTTTGGCAGTACATCAATGGGCGTGGATAGCGGTTTGACTCACGGGGATTTCCAAGTCTC
CACCCCATTGACGTCAATGGGAGTTTGTTTTGGCACCAAAATCAACGGGACTTTCCAAAATGTC
GTAACAACTCCGCCCCATTGACGCAAATGGGCGGTAGGCGTGTACGGTGGGAGGTCTATATAAG
CAGAGCTCGTTTAGTGAACCGTCAGATCGCCTGGAGACGCCATCCACGCTGTTTGACCTCCAT
AGAAGACACCGGGACCGATCCAGCCTCCGCGGCCGGGAACGGTGCATTGGAACGCGGATTCCCC
GTGCCAACAGTGACGTAAGTACCGCCTATAGACTCTATAGGCACACCCCTTTGGCTCTTATGCA
TGCTATACTGTTTTTGGCTTGGGGCCTATACACCCCGCTTCCTTATGCTATAGGTGATGGTAT
AGCTTAGCCTATAGGTGTGGGTTATTGACCATTATTGACCACTCCCCTATTGGTGACGATACTT
TCCATTACTAATCCATAACATGGCTCTTTGCCACAACTATCTCTATTGGCTATATGCCAATACT
CTGTCCTTCAGAGACTGACACGGACTCTGTATTTTACAGGATGGGGTCCCATTTATTATTTAC
AAATTCACATATACAACAACGGCCGTCCCCCGTGCCCGCAGTTTTTATTAAACATAGCGTGGGAT
CTCCACGCGAATCTCGGGTACGTGTTCCGGACATGGGCTCTTCTCCGGTAGCGGCGGAGCTTCC
ACATCCGAGCCCTGGTCCCATGCCTCCAGCGGCTCATGGTCGCTCGGCAGCTCCTTGCTCCTAA
CAGTGGAGGCCAGACTTAGGCACAGCACAATGCCCACCACCACCAGTGTGCCGGCACAAGGCCGT
GGCGGTAGGGTATGTGTCTGAAAATGAGCGTGGAGATTGGGCTCGCACGGCTGACGCAGATGGA
AGACTTAAGGCAGCGGCAGAAGAAGATGCAGGCAGCTGAGTTGTTGTATTCTGATAAGAGTCAG
AGGTAACTCCCGTTGCGGTGCTGTTAACGGTGGAGGGCAGTGTAGTCTGAGCAGTACTCCTTGC
TGCCGCGCGCCGCCACCAGACATAATAGCTGACAGACTAACAGACTGTTCCTTTCCATGGGTCTT
TTCTGCAGGCCGCCACCATGGGTTGGAGCCTCATCTTGCTCTTCCTTGTCGCTGTTGCT**CATAT
GGCTAGC**AGCTTCAGGAGTCGGGACCTAGCCTGGTGAAACCTTCTCAGTCTCTGTCCCTCACC
TGCACTGTCACTGGTTACTCAATCACCAGTGATTTTGCCTGGAACTGGATCCGGCAGTTTCCAG
GAAACAAGCTGGAGTGGATGGGCTACATAAGTTATAGTGGTAACACTAGGTACAACCCATCTC
```

```
GATACCTGTCCGCCTTTCTCCCTTCGGGAAGCGTGGCGCTTTCTCAATGCTCACGCTGTAGGTA
TCTCAGTTCGGTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACACGACTTATCGC
CACTGGCAGCAGCCACTGGTAACAGGATTAGCAGAGCGAGGTATGTAGGCGGTGCTACAGAGTT
CTTGAAGTGGTGGCCTAACTACGGCTACACTAGAAGGACAGTATTTGGTATCTGCGCTCTGCTG
AAGCCAGTTACCTTCGGAAAAAGAGTTGGTAGCTCTTGATCCGGCAAACAAACCACCGCTGGTA
GCGGTGGTTTTTTGTTTGCAAGCAGCAGATTACGCGCAGAAAAAAGGATCTCAAGAAGATCC
TTTGATCTTTTCTACGGGGTCTGACGCTCAGTGGAACGAAAACTCACGTTAAGGGATTTTGGTC
ATGAGATTATCAAAAAGGATCTTCACCTAGATCCTTTTAAATTAAAAATGAAGTTTTAAATCAA
TCTAAAGTATATATGAGTAAACTTGGTCTGACAGTTACCAATGCTTAATCAGTGAGGCACCTAT
CTCAGCGATCTGTCTATTTCGTTCATCCATAGTTGCCTGACTCCGGGGGGGGGGGCGCTGAGG
TCTGCCTCGTGAAGAAGGTGTTGCTGACTCATACCAGGCCTGAATCGCCCCATCATCCAGCCAG
AAAGTGAGGGAGCCACGGTTGATGAGAGCTTTGTTGTAGGTGGACCAGTTGGTGATTTTGAACT
TTTGCTTTGCCACGGAACGGTCTGCGTTGTCGGGAAGATGCGTGATCTGATCCTTCAACTCAGC
AAAAGTTCGATTTATTCAACAAAGCCGCCGTCCCGTCAAGTCAGCGTAATGCTCTGCCAGTCTT
ACAACCAATTAACCAATTCTGATTAGAAAAACTCATCGAGCATCAAATGAAACTGCAATTTATT
CATATCAGGATTATCAATACCATATTTTTGAAAAAGCCGTTTCTGTAATGAAGGAGAAAACTCA
CCGAGGCAGTTCCATAGGATGGCAAGATCCTGGTATCGGTCTGCGATTCCGACTCGTCCAACAT
CAATACAACCTATTAATTTCCCCTCGTCAAAAATAAGGTTATCAAGTGAGAAATCACCATGAGT
GACGACTGAATCCGGTGAGAATGGCAAAAGCTTATGCATTTCTTTCCAGACTTGTTCAACAGGC
CAGCCATTACGCTCGTCATCAAAATCACTCGCATCAACCAAACCGTTATTCATTCGTGATTGCG
CCTGAGCGAGACGAAATACGCGATCGCTGTTAAAAGGACAATTACAAACAGGAATCGAATGCAA
CCGGCGCAGGAACACTGCCAGCGCATCAACAATATTTTCACCTGAATCAGGATATTCTTCTAAT
ACCTGGAATGCTGTTTTCCCGGGGATCGCAGTGGTGAGTAACCATGCATCATCAGGAGTACGGA
TAAAATGCTTGATGGTCGGAAGAGGCATAAATTCCGTCAGCCAGTTTAGTCTGACCATCTCATC
TGTAACATCATTGGCAACGCTACCTTTGCCATGTTTCAGAAACAACTCTGGCGCATCGGGCTTC
CCATACAATCGATAGATTGTCGCACCTGATTGCCCGACATTATCGCGAGCCCATTTATACCCAT
ATAAATCAGCATCCATGTTGGAATTTAATCGCGGCCTCGAGCAAGACGTTTCCCGTTGAATATG
GCTCATAACACCCCTTGTATTACTGTTTATGTAAGCAGACAGTTTTATTGTTCATGATGATATA
TTTTATCTTGTGCAATGTAACATCAGAGATTTTGAGACACAACGTGGCTTTCCCCCCCCCCCC
ATTATTGAAGCATTTATCAGGGTTATTGTCTCATGAGCGGATACATATTTGAATGTATTTAGAA
AAATAAACAAATAGGGGTTCCGCGCACATTTCCCCGAAAAGTGCCACCTGACGTCTAAGAAACC
ATTATTATCATGACATTAACCTATAAAAATAGGCGTATCACGAGGCCCTTTCGTC
```

Figure 10 (Continued)

Ab-Fn3 Fusion Sequences

Abbreviations: HC=Heavy Chain; LC=Light Chain; VH=Heavy Chain Variable Domain; VL=Light Chain Variable Domain gWiz BS28-HC

PstI -- Kozak Sequence -- *Leader* -- MluI -- 225HC -- NheI -- CH1,2,3 -- (Gly4Ser)2 Linker -- 806 VH -- (Gly4Ser)3 linker -- 806 VL -- *Stop* -- SalI

```
TCGCGCGTTTCGGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGTGTTGGCGGGTT
CGGGGCTGGCTTAACTATGCGGCATCAGAGCAGATTGTACTGAGAGTGCACCATATGCGGTGTGA
AATACCGCACAGATGCGTAAGGAGAAAATACCGCATCAGATTGGCTATTGGCCATTGCATACGTT
GTATCCATATCATAATATGTACATTTATATTGGCTCATGTCCAACATTACCGCCATGTTGACATT
GATTATTGACTAGTTATTAATAGTAATCAATTACGGGGTCATTAGTTCATAGCCCATATATGGAG
TTCCGCGTTACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACGTCAATGGG
TGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGA
CTTTCCTACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTCGTTTAG
TGAACCGTCAGATCGCCTGGAGACGCCATCCACGCTGTTTTGACCTCCATAGAAGACACCGGGAC
CGATCCAGCCTCCGCGGCCGGGAACGGTGCATTGGAACGCGGATTCCCCGTGCCAAGAGTGACGT
AAGTACCGCCTATAGACTCTATAGGCACACCCCTTTGGCTCTTATGCATGCTATACTGTTTTTGG
CTTGGGGCCTATACACCCCCGCTTCCTTATGCTATAGGTGATGGTATAGCTTAGCCTATAGGTGT
GGGTTATTGACCATTATTGACCACTCCCCTATTGGTGACGATACTTTCCATTACTAATCCATAAC
ATGGCTCTTTGCCACAACTATCTCTATTGGCTATATGCCAATACTCTGTCCTTCAGAGACTGACA
CGGACTCTGTATTTTTACAGGATGGGGTCCCATTTATTATTTACAAATTCACATATACAACAACG
CCGTCCCCCGTGCCCGCAGTTTTTATTAAACATAGCGTGGGATCTCCACGCGAATCTCGGGTACG
TGTTCCGGACATGGGCTCTTCTCCGGTAGCGGCGGAGCTTCCACATCCGAGCCCTGGTCCCATGC
CTCCAGCGGCTCATGGTCGCTCGGCAGCTCCTTGCTCCTAACAGTGGGAGGCCAGACTTAGGCACA
GCACAATGCCCCACCACCACCAGTGTGCCGCACAAGGCCGTGGCGGTAGGGTATGTGTCTGAAAAT
GAGCGGTGGAGATTGGGCTCGCACGGCTGACGCAGATGGAAGACTTAAGGGCAGCGGCAGAAGAAGA
TGCAGGCAGCTGAGTTGTTGTATTCTGATAAGAGTCAGAGGGTAACTCCCGTTGCGGTGCTGTTAA
CGGTGGAGGGCAGTGTAGTCTGAGCAGTACTCGTTGCTGCCGCGCGCCACCAGACATAATAGC
TGACAGACTAACAGACTGTTCCTTTCCATGGGTCTTTTCTGCAGGCCGCCACC*ATGGGTTGGAGC
CTCATCTTGCTCTTCCTTGTCGCTGTTGCTACGCGTCAGGTACAACTGAAGCAGTCAGGACCTGG
CCTAGTGCAGCCCTTCACAGAGCCTGTCCATCACCTGCACAGTCTCTGGTTTCTCATTAACTAACT
ATGGTGTACACTGGGTTCGCCAGTCTCCAGGAAAGGGTCTGGAGTGGCTGGGAGTGATATGGAGT
GGTGGAAACACAGACTATAATACACCTTTCACATCCAGACTGAGCATCAACAAGGACAATTCCAA
GAGCCAAGTTTTCTTTAAAATGAACAGTCTGCAATCTAATGACACAGCCATATATTACTGTGCCA
GAGCCCTCACCTACTATGATTACGAGTTTGCTTACTGGGGCCAAGGGACCCTGGTCACCGTTTCC
GCTGCTAGCACCAAGGGCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGACGGTGTCGTGGAACT
CAGGCGCCCTGACCAGCGGCGTGCACACCTTCCCGGCTGTCCTACAGTCCTCAGGACTCTACTCC
CTCAGCAGCGTGGTGACCGTGCCCTCCAGCAGCTTGGGCACCCAGACCTACATCTGCAACGTGAA
TCACAAGCCCAGCAACACCAAGGTGGACAAGAAAGTTGAGCCCAAATCTTGTGACAAAACTCACA
```

AATGCTCTGCCAGTGTTACAACCAATTAACCAATTCTGATTAGAAAAACTCATCGAGCATCAAAT
GAAACTGCAATTTATTCATATCAGGATTATCAATACCATATTTTTGAAAAAGCCGTTTCTGTAAT
GAAGGAGAAAACTCACCGAGGCAGTTCCATAGGATGGCAAGATCCTGGTATCGGTCTGCGATTCC
GACTCGTCCAACATCAATACAACCTATTAATTTCCCCTCGTCAAAAATAAGGTTATCAAGTGAGA
AATCACCATGAGTGACGACTGAATCCGGTGAGAATGGCAAAAGCTTATGCATTTCTTTCCAGACT
TGTTCAACAGGCCAGCCATTACGCTCGTCATCAAAATCACTCGCATCAACCAAACCGTTATTCAT
TCGTGATTGCGCCTGAGCGAGACGAAATACGCGATCGCTGTTAAAAGGACAATTACAAACAGGAA
TCGAATGCAACCGGCGCAGGAACACTGCCAGCGCATCAACAATATTTTCACCTGAATCAGGATAT
TCTTCTAATACCTGGAATGCTGTTTTCCCGGGGATCGCAGTGGTGAGTAACCATGCATCATCAGG
AGTACGGATAAATGCTTGATGGTCGGAAGAGGCATAAATTCCGTCAGCCAGTTTAGTCTGACCA
TCTCATCTGTAACATCATTGGCAACGCTACCTTTGCCATGTTTCAGAAACAACTCTGGCGCATCG
GGCTTCCCATACAATCGATAGATTGTCGCACCTGATTGCCCGACATTATCGCGAGCCCATTTATA
CCCATATAAATCAGCATCCATGTTGGAATTTAATCGCGGCCTCGAGCAAGACGTTTCCCGTTGAA
TATGGCTCATAACACCCCTTGTATTACTGTTTATGTAAGCAGACAGTTTTATTGTTCATGATGAT
ATATTTTTATCTTGTGCAATGTAACATCAGAGATTTTGAGACACAACGTGGCTTTCCCCCCCCCC
CCATTATTGAAGCATTTATCAGGGTTATTGTCTCATGAGCGGATACATATTTGAATGTATTTAGA
AAAATAAACAAATAGGGGTTCCGCGCACATTTCCCCGAAAAGTGCCACCTGACGTCTAAGAAACC
ATTATTATCATGACATTAACCTATAAAAATAGGCGTATCACGAGGCCCTTTCGTC

Figure 11 (Continued)

Ab-Fn3 Fusion Sequences

Abbreviations: HC=Heavy Chain; LC=Light Chain; VH=Heavy Chain Variable Domain; VL=Light Chain Variable Domain gWiz BS28-LN

PstI -- Kozak Sequence -- *Leader* -- NdeI -- NheI -- 806 VH -- (Gly4Ser)3 linker -- 806 VL --
BamHI -- (Gly4Ser)3 Linker -- DraIII -- 225LC -- BsiWI -- Ckappa -- *Stop* -- SalI

```
TCGCGCGTTTCGGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGTGTTGGCGGGTT
CGGGGCTGGCTTAACTATGCGGCATCAGAGCAGATTGTACTGAGAGTGCACCATATGCGGTGTGA
AATACCGCACAGATGCGTAAGGAGAAAATACCGCATCAGATTGGCTATTCGCCATTGCATACGTT
GTATCCATATCATAATATGTACATTTATATTGGCTCATGTCCAACATTACCGCCATGTTGACATT
GATTATTGACTAGTTATTAATAGTAATCAATTACGGGGTCATTAGTTCATAGCCCATATATGGAG
TTCCGCGTTACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACGTCAATGGG
TGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGA
CTTTCCTACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTCGTTTAG
TGAACCGTCAGATCGCCTGGAGACGCCATCCACGCTGTTTTGACCTCCATAGAAGACACCGGGAC
CGATCCAGCCTCCGCGGCCGGAACGTGCATTGGAACGCGGATTCCCCGTGCCAAGAGTGACGT
AAGTACCGCCTATAGACTCTATAGGCACACCCCTTGGCTCTTATGCATGCTATACTGTTTTTGG
CTTGGGGCCTATACACCCCCGCTTCCTTATGCTATAGGTGATGGTATAGCTTAGCCTATAGGTGT
GGGTTATTGACCATTATTGACCACTCCCCTATTGGTGACGATACTTTCCATTACTAATCCATAAC
ATGGCTCTTTGCCACAACTATCTCTATTGCTATATGCCAATACTCTGTCCTTCAGAGACTGACA
CGGACTCTGTATTTTTACAGGATGGGGTCCCATTTATTATTTACAAATTCACATATACAACAACG
CCGTCCCCCGTGCCCGCAGTTTTTATTAAACATAGCGTGGGATCTCCACGCGAATCTCGGGTACG
TGTTCCGGACATGGGCTCTTCTCCGGTAGCGGCGGAGCTTCCACATCCGAGCCCTGGTCCCATGC
CTCCAGCGGCTCATGGTCGCTCGGCAGCTCCTTGCTCCTAACAGTGGAGGCCAGACTTAGGCACA
GCACAATGCCCACCACCACCAGTGTGCCGCACAAGGCCGTGGCGGTAGGGTATGTGTCTGAAAAT
GAGCGTGGAGATTGGGCTCGCACGGCTGACGCAGATGGAAGACTTAAGGCAGCGGCAGAAGAAGA
TGCAGGCAGCTGAGTTGTTCTATTCTGATAAGAGTCAGAGGTAACTCCCGTTGCGGTGCTGTTAA
CGGTGGAGGGCAGTGTAGTCTGAGCAGTACTCGTTGCTGCCGCGCGCCACCAGACATAATAGC
TGACAGACTAACAGACTGTTCCTTTCCATGGGTCTTTTCTGCAGGCCGCCACCATGAGGGTCCCC
GCTCAGCTCCTGGGGCTCCTGCTGCTCTGGCTCCCAGGTGCACATATGGCTAGC**CAGCTTCAGGA
GTCGGGACCTAGCCTGGTGAAACCTTCTCAGTCTCTGTCCCTCACCTGCACTGTCACTGGCTACT
CAATCACCAGTGATTTTGCCTGGAACTGGATCCGGCAGTTTCCAGGAAACAAGCTGGAGTGGATG
GGCTACATAAGTTATAGTGGTAACACTAGGTACAACCCATCTCTCAAAAGTCGAATCTCTATCAC
TCGAGACACATCCAAGAACCAATTCTTCCTGCAGTTGAATTCTGTGACTATTGAGGACACAGCCA
CATATTACTGTGTAACGGCGGACGCGGGTTTCCTTATTGGCGCCAAGGGACTCTGGTCACTGTC
TCTGCAGGAGCGGCGGATCTGGCGGTGGAGGTTCTGGCGGCGGCGGATCTGACATCCTGATGAC
CCAATCTCCATCCTCCATGTCTGTATCTCTGGGAGACACAGTCAGCATCACTTGCCATTCAAGTC
AGGACATTAACAGTAATATAGGGTGGTTGCAGCAGAGACCAGGGAAATCATTTAAGGGCCTGATC
TATCATGGAACCAACTTGGACGATGAAGTTCCATCAAGGTTCAGTGGCAGTGGATCTGGAGCCGA
TTATTCTCTCACCATCAGCAGCCTGGAATCTGAAGATTTTGCAGACTATTACTGTGTACAGTATG
```

Figure 12

```
CTCAGTTTCCGTGGACGTTCGGTGGAGGCACCAAGCTGGAAATCAAACGTGGATCCCGGAGGTGGC
GGTAGTGGCGGAGGTGGTTCTTCACGATGTGACATCCTGCTGACCCAGTCTCCAGTCATCCTGTC
TGTGAGTCCAGGAGAAAGAGTCAGTTTCTCCTGCAGGGCCAGTCAGAGTATTGGCACAAACATAC
ACTGGTATCAGCAAAGAACAAATGGTTCTCCAAGGCTTCTCATAAAGTATGCTTCTGAGTCTATC
TCTGGCATCCCTTCCAGGTTTAGTGGCAGTGGATCAGGGACAGATTTTACTCTTAGCATCAACAG
TGTGGAGTCTGAAGATATTGCAGATTATTACTGTCAACAAAATAATAACTGGCCAACCACGTTCG
GTGCTGGGACCAAGCTGGAGCTCAAACGTACGGTGGCTGCACCATCTGTCTTCATCTTCCCGCCA
TCTGATGAGCAGTTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCCCAGGAGAGTGTCA
CAGAGCAGGACAGCAAGGACAGCACCTACAGCCTCAGCAGCACCCTGACGCTGAGCAAAGCAGAC
TACGAGAAACACAAAGTCTACGCCTGCGAAGTCACCCATCAGGGCCTGAGCTCGCCCGTCACAAA
GAGCTTCAACAGGGGAGAGTGTTAATAGGTCGACACGTGTGATCAGATATCGCGGCCGCTCTAGA
CCAGGCGCCTGGATCCAGATCACTTCTGGCTAATAAAGATCAGAGCTCTAGAGATCTGTGTGTT
GGTTTTTTTGTGGATCTGCTGTGCCTTCTAGTTGCCAGCCATCTGTTGTTTGCCCCTCCCCCGTGC
CTTCCTTGACCCTGGAAGGTGCCACTCCCACTGTCCTTTCCTAATAAAATGAGGAAATTGCATCG
CATTGTCTGAGTAGGTGTCATTCTATTCTGGGGGGTGGGGTGGGGCAGCACAGCAAGGGGGAGGA
TTGGGAAGACAATAGCAGGCATGCTGGGGATGCGGTGGGCTCTATGGGTACCTCTCTCTCTCTCT
CTCTCTCTCTCTCTCTCTCTCTCTCTCTCGGTACCTCTCTCTCTCTCTCTCTCTCTCTCTCTCTC
TCTCTCTCGGTACCAGGTGCTGAAGAATTGACCCGGTTCCTCCTGGGCCAGAAAGAAGCAGGCAC
ATCCCCTTCTCTGTGACACACCCTGTCCACGCCCCTGGTTCTTAGTTCCAGCCCCACTCATAGGA
CACTCATAGCTCAGGAGGGCTCCGCCTTCAATCCCACCCGCTAAAGTACTTGGAGCGGTCTCTCC
CTCCCTCATCAGCCCACCAAACCAAACCTAGCCTCCAAGAGTGGGAAGAAATTAAAGCAAGATAG
GCTATTAAGTGCAGAGGGAGAGAAAATGCCTCCAACATGTGAGGAAGTAATGAGAGAAATCATAG
AATTTCTTCCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCATAG
GCTCCGCCCCCCTGACGAGCATCACAAAAATCGACGCTCAAGTCAGAGGTGGCGAAACCCGACAG
GACTATAAAGATACCAGGCGTTTCCCCCTGGAAGCTCCCTCGTGCGCTCTCCTGTTCCGACCCTG
CCGCTTACCGGATACCTGTCCGCCTTTCTCCCTTCGGGAAGCGTGGCGCTTTCTCAATGCTCACG
CTGTAGGTATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAAGACACGAC
TTATCGCCACTGGCAGCAGCCACTGGTAACAGGATTAGCAGAGCGAGGTATGTAGGCGGTGCTAC
AGAGTTCTTGAAGTGGTGGCCTAACTACGGCTACACTAGAAGGACAGTATTTGGTATCTGCGCTC
TGCTGAAGCCAGTTACCTTCGGAAAAAGAGTTGGTAGCTCTTGATCCGGCAAACAAACCACCGCT
GGTAGCGGTGGTTTTTTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCACGTTAAGGGATTTTGG
TCATGAGATTATCAAAAAGGATCTTCACCTAGATCCTTTTAAATTAAAAATGAAGTTTTAAATCA
ATCTAAAGTATATATGAGTAAACTTGGTCTGACAGTTACCAATGCTTAATCAGTGAGGCACCTAT
CTCAGCGATCTGTCTATTTCGTTCATCCATAGTTGCCTGACTCCCGGGGGGGGGGGCGCTGAGGT
CTGCCTCGTGAAGAAGGTGTTGCTGACTCATACCAGGCCTGAATCGCCCCATCATCCAGCCAGAA
AGTGAGGGAGCCACGGTTGATGAGAGCTTTGTTGTAGGTGGACCAGTTGGTGATTTTGAACTTTT
GCTTTGCCACGGAACGGTCTGCGTTGTCGGGAAGATGCGTGATCTGATCCTTCAACTCAGCAAAA
GTTCGATTTATTCAACAAAGCCGCCGTCCCGTCAAGTCAGCGTAATGCTCTGCCAGTGTTACAAC
CAATTAACCAATTCTGATTAGAAAAACTCATCGAGCATCAAATGAAACTGCAATTTATTCATATC
AGGATTATCAATACCATATTTTTGAAAAAGCCGTTTCTGTAATGAAGGAGAAAACTCACCGAGGC
AGTTCCATAGGATGGCAAGATCCTGGTATCGGTCTGCGATTCCGACTCGTCCAACATCAATACAA
CCTATTAATTTCCCCTCGTCAAAAATAAGGTTATCAAGTGAGAAATCACCATGAGTGACGACTGA
ATCCGGTGAGAATGGCAAAAGCTTATGCATTTCTTTCCAGACTTGTTCAACAGGCCAGCCATTAC
GCTCGTCATCAAAATCACTCGCATCAACCAAACCGTTATTCATTCGTGATTGCGCCTGAGCGAGA
CGAAATACGCGATCGCTGTTAAAAGGACAATTACAAACAGGAATCGAATGCAACCGGCGCAGGAA
CACTGCCAGCGCATCAACAATATTTTCACCTGAATCAGGATATTCTTCTAATACCTGGAATGCTG
TTTTCCCGGGGATCGCAGTGGTGAGTAACCATGCATCATCAGGAGTACGGATAAAATGCTTGATG
GTCGGAAGAGGCATAAATTCCGTCAGCCAGTTTAGTCTGACCATCTCATCTGTAACATCATTGGC
```

```
AACGCTACCTTTGCCATGTTTCAGAAACAACTCTGGCGCATCGGGCTTCCCATACAATCGATAGA
TTGTCGCACCTGATTGCCCGACATTATCGCGAGCCCATTTATACCCATATAAATCAGCATCCATG
TTGGAATTTAATCGCGGCCTCGAGCAAGACGTTTCCCGTTGAATATGGCTCATAACACCCCTTGT
ATTACTGTTTATGTAAGCAGACAGTTTTATTGTTCATGATGATATATTTTTATCTTGTGCAATGT
AACATCAGAGATTTTGAGACACAACGTGGCTTTCCCCCCCCCCCATTATTGAAGCATTTATCAG
GGTTATTGTCTCATGAGCGGATACATATTTGAATGTATTTAGAAAAATAAACAAATAGGGGTTCC
GCGCACATTTCCCCGAAAAGTGCCACCTGACGTCTAAGAAACCATTATTATCATGACATTAACCT
ATAAAAATAGGCGTATCACGAGGCCCTTTCGTC
```

Figure 12 (Continued)

Ab-Fn3 Fusion Sequences

Abbreviations: HC=Heavy Chain; LC=Light Chain; VH=Heavy Chain Variable Domain; VL=Light Chain Variable Domain gWiz BS28-LC

PstI -- Kozak Sequence -- *Leader* -- DraIII -- 225LC -- BsiWI -- Ckappa -- (Gly₄Ser)₃ Linker -- 806 VH -- (Gly4Ser)₃ linker -- 806 VL -- GS Spacer -- Cmyc Epitope Tag -- *Stop* -- SalI

```
TCGCGCGTTTCGGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGTGTTGGCGGGTT
CGGGGCTGGCTTAACTATGCGGCATCAGAGCAGATTGTACTGAGAGTGCACCATATGCGGTGTGA
AATACCGCACAGATGCGTAAGGAGAAAATACCGCATCAGATTGGCTATTGGCCATTGCATACGTT
GTATCCATATCATAATATGTACATTTATATTGGCTCATGTCCAACATTACCGCCATGTTGACATT
GATTATTGACTAGTTATTAATAGTAATCAATTACGCGGTCATTAGTTCATAGCCCATATATGGAG
TTCCGGCGTTACATAACTTACGGTAAATGGCCCGCCTGGCTGACCGCCCAACGACCCCCGCCCATT
GACGTCAATAATGACGTATGTTCCCATAGTAACGCCAATAGGGACTTTCCATTGACGTCAATGGG
TGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGA
CTTTCCTACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACCCCATTGAC
GTCAATGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTCGTTTAG
TGAACCGTCAGATCGCCTGGAGACGCCATCCACGCTGTTTTGACCTCCATAGAAGACACCGGGAC
CGATCCAGCCTCCGCGGCCGGGAACGGTGCATTGGAACGCGGATTCCCCGTGCCAAGAGTGACGT
AAGTACCGCCTATAGACTCTATAGGCACACCCCTTTGGCTCTTATGCATGCTATACTGTTTTTGG
CTTGGGGCCTATACACCCCGCTTCCTTATGCTATAGGTGATGGTATAGCTTAGCCTATAGGTGT
GGGTTATTGACCATTATTGACCACTCCCCTATTGGTGACGATACTTTCCATTACTAATCCATAAC
ATGGCTCTTTGCCACAACTATCTCTATTGGCTATATGCCAATACTCTGTCCTTCAGAGACTGACA
CGGACTCTGTATTTTTACAGGATGGGGTCCCATTTATTATTTACAAATTCACATATACAACAACG
CCGTCCCCCGTGCCCGCAGTTTTTATTAAACATAGCGTGGGATCTCCACGCGAATCTCGGGTACG
TGTTCCGGACATGGGCTCTTCTCCGGTAGCGGCGGAGCTTCCACATCCGAGCCCTGGTCCCATGC
CTCCAGCGGCTCATGGTCGCTCGGCAGCTCCTTGCTCCTAACAGTGGAGGCCAGACTTAGGCACA
GCACAATGCCCACCACCACCAGTGTGCCGCACAAGGCCGTGGCGGTAGGGTATGTGTCTGAAAAT
GAGCGTGGAGATTGGGCTCGCACGGCTGACGCAGATGGAAGACTTAAGGCAGCGGCAGAAGAAGA
TGCAGGCAGCTGAGTTGTTGTATTCTGATAAGAGTCAGAGGTAACTCCCGTTGCGGTGCTGTTAA
CGGTGGAGGGCAGTGTAGTCTGAGCAGTACTCGTTGCTGCCGCGCGCCACCAGACATAATAGC
TGACAGACTAACAGACTGTTCCTTTCCATGGGTCTTTTCTGCAGGCCGCCACCATGAGGGTCCCC
GCTCAGCTCCTGGGGCTCCTGCTGCTCTGGCTCCCAGGTGCACACGATGTGACATCCTGCTGACC
CAGTCTCCAGTCATCCTGTCTGTGAGTCCAGGAGAAAGAGTCAGTTTCTCCTGCAGGGCCAGTCA
GAGTATTGGCACAAACATACACTGGTATCAGCAAAGAACAAATGGTTCTCCAAGGCTTCTCATAA
AGTATGCTTCTGAGTCTATCTCTGGCATCCCTTCCAGGTTTAGTGGCAGTGGATCAGGGACAGAT
TTTACTCTTAGCATCAACAGTGTGGAGTCTGAAGATATTGCAGATTATTACTGTCAACAAATAA
TAACTGGCCAACCACGTTCGGTGCTGGGACCAAGCTGGAGCTCAAACGTACGGTGGCTGCACCAT
CTGTCTTCATCTTCCCGCCATCTGATGAGCAGTTGAAATCTGGAACTGCCTCTGTTGTGTGCCTG
CTGAATAACTTCTATCCCAGAGAGGCCAAAGTACAGTGGAAGGTGGATAACGCCCTCCAATCGGG
TAACTCCCAGGAGAGTGTCACAGAGCAGGACAGCAAGGACAGCACCTACAGCCTCAGCAGCACCC
TGACGCTGAGCAAAGCAGACTACGAGAAACACAAAGTCTACGCCTGCGAAGTCACCCATCAGGGC
CTGAGCTCGCCCGTCACAAAGAGCTTCAACAGGGGAGAGTGTGGAGGTGGCGGTAGTGCGGAGG
```

```
TCTGTAACATCATTGGCAACGCTACCTTTGCCATGTTTCAGAAACAACTCTGGCGCATCGGGCTT
CCCATACAATCGATAGATTGTCGCACCTGATTGCCCGACATTATCGCGAGCCCATTTATACCCAT
ATAAATCAGCATCCATGTTGGAATTTAATCGCGGCCTCGAGCAAGACGTTTCCCGTTGAATATGG
CTCATAACACCCCTTGTATTACTGTTTATGTAAGCAGACAGTTTTATTGTTCATGATGATATATT
TTTATCTTGTGCAATGTAACATCAGAGATTTTGAGACACAACGTGGCTTTCCCCCCCCCCCATT
ATTGAAGCATTTATCAGGGTTATTGTCTCATGAGCCGATACATATTTGAATGTATTTACAAAAAT
AAACAAATAGGGGTTCCGCGCACATTTCCCCGAAAAGTGCCACCTGACGTCTAAGAAACCATTAT
TATCATGACATTAACCTATAAAAATAGGCGTATCACGAGGCCCTTTCGTC
```

Figure 13 (Continued)

SEQUENCE LISTING

```
<160> NUMBER OF SEQ ID NOS: 32

<210> SEQ ID NO 1
<211> LENGTH: 15
<212> TYPE: PRT
<213> ORGANISM: Artificial Sequence
<220> FEATURE:
<223> OTHER INFORMATION: Synthetic: Polypeptide linker

<400> SEQUENCE: 1

Gly Ser Gly Gly Gly Ser Gly Gly Gly Lys Gly Gly Gly Gly Thr
1               5                   10                  15

<210> SEQ ID NO 2
<211> LENGTH: 1864
<212> TYPE: DNA
<213> ORGANISM: Artificial Sequence
<220> FEATURE:
<223> OTHER INFORMATION: Synthetic: Vector sequence

<400> SEQUENCE: 2
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg      120
ttggcgggtt cggggctggc ttaactatgc ggcatcagag cagattgtac tgagagtgca      180
ccatatgcgg tgtgaaatac cgcacagatg cgtaaggaga aaataccgca tcagattggc      240
tattggccat tgcatacgtt gtatccatat cataatatgt acatttatat tggctcatgt      300
ccaacattac cgccatgttg acattgatta ttgactagtt attaatagta atcaattacg      360
gggtcattag ttcatagccc atatatggag ttccgcgtta cataacttac ggtaaatggc      420
ccgcctggct gaccgcccaa cgacccccgc ccattgacgt caataatgac gtatgttccc      480
atagtaacgc caatagggac tttccattga cgtcaatggg tggagtattt acggtaaact      540
```

```
gcccacttgg cagtacatca agtgtatcat atgccaagta cgccccctat tgacgtcaat      600
gacggtaaat ggcccgcctg gcattatgcc cagtacatga ccttatggga ctttcctact      660
tggcagtaca tctacgtatt agtcatcgct attaccatgg tgatgcggtt ttggcagtac      720
atcaatgggc gtggatagcg gtttgactca cggggatttc caagtctcca ccccattgac      780
gtcaatggga gtttgttttg gcaccaaaat caacgggact ttccaaaatg tcgtaacaac      840
tccgccccat tgacgcaaat gggcggtagg cgtgtacggt gggaggtcta tataagcaga      900
gctcgtttag tgaaccgtca gatcgcctgg agacgccatc cacgctgttt tgacctccat      960
agaagacacc gggaccgatc cagcctccgc ggccgggaac ggtgcattgg aacgcggatt     1020
ccccgtgcca agagtgacgt aagtaccgcc tatagactct ataggcacac ccctttggct     1080
cttatgcatg ctatactgtt tttggcttgg ggcctataca ccccgcttc cttatgctat      1140 aggtgatggt atagcttagc ctataggtgt gggttattga ccattattga ccactcccct     1200
attggtgacg atactttcca ttactaatcc ataacatggc tctttgccac aactatctct     1260
attggctata tgccaatact ctgtccttca gagactgaca cggactctgt attttacag      1320 gatggggtcc catttattat ttacaaattc acatatacaa caacgccgtc ccccgtgccc     1380
gcagttttta ttaaacatag cgtgggatct ccacgcgaat ctcgggtacg tgttccggac     1440
atgggctctt ctccggtagc ggcggagctt ccacatccga ccctggtcc catgcctcca     1500 gcggctcatg gtcgctcggc agctccttgc tcctaacagt ggaggccaga cttaggcaca     1560
gcacaatgcc caccaccacc agtgtgccgc acaaggccgt ggcggtaggg tatgtgtctg     1620
aaaatgagcg tggagattgg gctcgcacgg ctgacgcaga tggaagactt aaggcagcgg     1680
cagaagaaga tgcaggcagc tgagttgttg tattctgata agagtcagag gtaactcccg     1740
ttgcggtgct gttaacggtg gagggcagtg tagtctgagc agtactcgtt gctgccgcgc     1800
gcgccaccag acataatagc tgacagacta acagactgtt cctttccatg ggtcttttct     1860
gcag                                                                  1864
```

<210> SEQ ID NO 3
<211> LENGTH: 9
<212> TYPE: DNA
<213> ORGANISM: Artificial Sequence
<220> FEATURE:
<223> OTHER INFORMATION: Synthetic: Kozak Sequence

<400> SEQUENCE: 3

```
gccgccacc                                                               9
```

<210> SEQ ID NO 4
<211> LENGTH: 42
<212> TYPE: DNA
<213> ORGANISM: Artificial Sequence
<220> FEATURE:
<223> OTHER INFORMATION: Synthetic: leader sequence

<400> SEQUENCE: 4

```
atgggttgga gcctcatctt gctcttcctt gtcgctgttg ct                          42
```

<210> SEQ ID NO 5
<211> LENGTH: 6
<212> TYPE: DNA
<213> ORGANISM: Artificial Sequence
<220> FEATURE:
<223> OTHER INFORMATION: Synthetic: NdeI restriction site

```
<400> SEQUENCE: 5 catatg                                                                    6

<210> SEQ ID NO 6
<211> LENGTH: 6
<212> TYPE: DNA
<213> ORGANISM: Artificial Sequence
<220> FEATURE:
<223> OTHER INFORMATION: Synthetic: NheI restriction site

<400> SEQUENCE: 6 gctagc                                                                    6

<210> SEQ ID NO 7
<211> LENGTH: 342
<212> TYPE: DNA
<213> ORGANISM: Artificial Sequence
<220> FEATURE:
<223> OTHER INFORMATION: Synthetic: 806 VH sequence

<400> SEQUENCE: 7
cagcttcagg agtcgggacc tagcctggtg aaaccttctc agtctctgtc cctcacctgc         60
actgtcactg gctactcaat caccagtgat tttgcctgga actggatccg gcagtttcca        120
ggaaacaagc tggagtggat gggctacata agttatagtg gtaacactag gtacaaccca        180
tctctcaaaa gtcgaatctc tatcactcga gacacatcca gaaccaatt cttcctgcag         240 ttgaattctg tgactattga ggacacagcc acatattact gtgtaacggc gggacgcggg        300
tttccttatt ggggccaagg gactctggtc actgtctctg ca                          342

<210> SEQ ID NO 8
<211> LENGTH: 45
<212> TYPE: DNA
<213> ORGANISM: Artificial Sequence
<220> FEATURE:
<223> OTHER INFORMATION: Synthetic: linker sequence

<400> SEQUENCE: 8
ggaggcggcg gatctggcgg tggaggttct ggcggcggcg gatct                        45

<210> SEQ ID NO 9
<211> LENGTH: 324
<212> TYPE: DNA
<213> ORGANISM: Artificial Sequence
<220> FEATURE:
<223> OTHER INFORMATION: Synthetic: 806 VL sequence

<400> SEQUENCE: 9
gacatcctga tgacccaatc tccatcctcc atgtctgtat ctctgggaga cacagtcagc         60
atcacttgcc attcaagtca ggacattaac agtaatatag ggtggttgca gcagagacca        120
gggaaatcat ttaagggcct gatctatcat ggaaccaact ggacgatga agttccatca         180 aggttcagtg gcagtggatc tggagccgat tattctctca ccatcagcag cctggaatct        240
gaagattttg cagactatta ctgtgtacag tatgctcagt ttccgtggac gttcggtgga        300
ggcaccaagc tggaaatcaa acgt                                              324

<210> SEQ ID NO 10
<211> LENGTH: 6
<212> TYPE: DNA
<213> ORGANISM: Artificial Sequence
<220> FEATURE:
<223> OTHER INFORMATION: Synthetic: BamHI restriction site
```

<400> SEQUENCE: 10 ggatcc                                                                          6

<210> SEQ ID NO 11
<211> LENGTH: 30
<212> TYPE: DNA
<213> ORGANISM: Artificial Sequence
<220> FEATURE:
<223> OTHER INFORMATION: Synthetic: linker sequence

<400> SEQUENCE: 11
ggaggtggcg gtagtggcgg aggtggttct                                               30

<210> SEQ ID NO 12
<211> LENGTH: 6
<212> TYPE: DNA
<213> ORGANISM: Artificial Sequence
<220> FEATURE:
<223> OTHER INFORMATION: Synthetic: MluI restriction site

<400> SEQUENCE: 12 acgcgt                                                                          6

<210> SEQ ID NO 13
<211> LENGTH: 357
<212> TYPE: DNA
<213> ORGANISM: Artificial Sequence
<220> FEATURE:
<223> OTHER INFORMATION: Synthetic: 225 HC sequence

<400> SEQUENCE: 13
caggtacaac tgaagcagtc aggacctggc ctagtgcagc cctcacagag cctgtccatc              60
acctgcacag tctctggttt ctcattaact aactatggtg tacactgggt tcgccagtct             120
ccaggaaagg gtctggagtg gctgggagtg atatggagtg gtggaaacac agactataat             180
acacctttca catccagact gagcatcaac aaggacaatt ccaagagcca gttttctttt             240
aaaatgaaca gtctgcaatc taatgacaca gccatatatt actgtgccag agccctcacc             300
tactatgatt acgagtttgc ttactggggc caagggaccc tggtcaccgt ttccgct                357

<210> SEQ ID NO 14
<211> LENGTH: 984
<212> TYPE: DNA
<213> ORGANISM: Artificial Sequence
<220> FEATURE:
<223> OTHER INFORMATION: Synthetic: CH 1,2,3 sequence

<400> SEQUENCE: 14
accaagggcc catcggtctt ccccctggca ccctcctcca agagcacctc tgggggcaca              60
gcggccctgg gctgcctggt caaggactac ttccccgaac cggtgacggt gtcgtggaac             120
tcaggcgccc tgaccagcgg cgtgcacacc ttcccggctg tcctacagtc ctcaggactc             180
tactccctca gcagcgtggt gaccgtgccc tccagcagct gggcacccca gacctacatc             240
tgcaacgtga atcacaagcc cagcaacacc aaggtggaca agaaagttga gcccaaatct             300
tgtgacaaaa ctcacacatg cccaccgtgc ccagcacctg aactcctggg ggaccgtca              360 gtcttcctct tccccccaaa acccaaggac accctcatga tctcccggac ccctgaggtc             420
acatgcgtgg tggtggacgt gagccacgaa gaccctgagg tcaagttcaa ctggtacgtg             480
gacggcgtgg aggtgcataa tgccaagaca aagccgcggg aggagcagta caacagcacg             540

| | |
|---|---|
| taccgtgtgg tcagcgtcct caccgtcctg caccaggact ggctgaatgg caaggagtac | 600 |
| aagtgcaagg tctccaacaa agccctccca gcccccatcg agaaaaccat ctccaaagcc | 660 |
| aaagggcagc cccgagaacc acaggtgtac accctgcccc catcccggga tgagctgacc | 720 |
| aagaaccagg tcagcctgac ctgcctggtc aaaggcttct atcccagcga catcgccgtg | 780 |
| gagtgggaga gcaatgggca gccggagaac aactacaaga ccacgcctcc cgtgctggac | 840 |
| tccgacggct ccttcttcct ctacagcaag ctcaccgtgg acaagagcag gtggcagcag | 900 |
| gggaacgtct tctcatgctc cgtgatgcat gaggctctgc acaaccacta cacgcagaag | 960 |
| agcctctccc tgtctccggg taaa | 984 |

```
<210> SEQ ID NO 15
<211> LENGTH: 6
<212> TYPE: DNA
<213> ORGANISM: Artificial Sequence
<220> FEATURE:
<223> OTHER INFORMATION: Synthetic: stop sequence

<400> SEQUENCE: 15
```

| | |
|---|---|
| tgataa | 6 |

```
<210> SEQ ID NO 16
<211> LENGTH: 6
<212> TYPE: DNA
<213> ORGANISM: Artificial Sequence
<220> FEATURE:
<223> OTHER INFORMATION: Synthetic: SalI sequence

<400> SEQUENCE: 16
```

| | |
|---|---|
| gtcgac | 6 |

```
<210> SEQ ID NO 17
<211> LENGTH: 3184
<212> TYPE: DNA
<213> ORGANISM: Artificial Sequence
<220> FEATURE:
<223> OTHER INFORMATION: Synthetic: Vector sequence

<400> SEQUENCE: 17
```

| | |
|---|---|
| acgtgtgatc agatatcgcg gccgctctag accaggcgcc tggatccaga tcacttctgg | 60 |
| ctaataaaag atcagagctc tagagatctg tgtgttggtt ttttgtggat ctgctgtgcc | 120 |
| ttctagttgc cagccatctg ttgtttgccc ctcccccgtg ccttccttga ccctggaagg | 180 |
| tgccactccc actgtccttt cctaataaaa tgaggaaatt gcatcgcatt gtctgagtag | 240 |
| gtgtcattct attctggggg gtggggtggg gcagcacagc aaggggagg attgggaaga | 300 |
| caatagcagg catgctgggg atgcggtggg ctctatgggt acctctctct ctctctctct | 360 |
| ctctctctct ctctctctct ctcggtacct ctctctctct ctctctctct ctctctctct | 420 |
| ctctctctcg gtaccaggtg ctgaagaatt gacccggttc ctcctgggcc agaaagaagc | 480 |
| aggcacatcc ccttctctgt gacacaccct gtccacgccc ctggttctta gttccagccc | 540 |
| cactcatagg acactcatag ctcaggaggg ctccgccttc aatcccaccc gctaaagtac | 600 |
| ttggagcggt ctctcccctcc ctcatcagcc caccaaacca aacctagcct ccaagagtgg | 660 |
| gaagaaatta aagcaagata ggctattaag tgcagaggga gagaaaatgc ctccaacatg | 720 |
| tgaggaagta atgagagaaa tcatagaatt tcttccgctt cctcgctcac tgactcgctg | 780 |
| cgctcggtcg ttcggctgcg gcgagcggta tcagctcact caaaggcggt aatacggtta | 840 |
| tccacagaat caggggataa cgcaggaaag aacatgtgag caaaaggcca gcaaaaggcc | 900 |

```
aggaaccgta aaaaggccgc gttgctggcg ttttccata ggctccgccc ccctgacgag    960
catcacaaaa atcgacgctc aagtcagagg tggcgaaacc cgacaggact ataaagatac   1020
caggcgtttc ccctggaag ctccctcgtg cgctctcctg ttccgaccct gccgcttacc    1080
ggatacctgt ccgcctttct cccttcggga agcgtggcgc tttctcaatg ctcacgctgt   1140
aggtatctca gttcggtgta ggtcgttcgc tccaagctgg gctgtgtgca cgaaccccc    1200
gttcagcccg accgctgcgc cttatccggt aactatcgtc ttgagtccaa cccggtaaga   1260
cacgacttat cgccactggc agcagccact ggtaacagga ttagcagagc gaggtatgta   1320
ggcggtgcta cagagttctt gaagtggtgg cctaactacg gctacactag aaggacagta   1380
tttggtatct gcgctctgct gaagccagtt accttcggaa aaagagttgg tagctcttga   1440
tccggcaaac aaaccaccgc tggtagcggt ggttttttg tttgcaagca gcagattacg     1500
cgcagaaaaa aaggatctca agaagatcct ttgatctttt ctacggggtc tgacgctcag   1560
tggaacgaaa actcacgtta agggattttg gtcatgagat tatcaaaaag gatcttcacc   1620
tagatccttt taaattaaaa atgaagtttt aaatcaatct aaagtatata tgagtaaact   1680
tggtctgaca gttaccaatg cttaatcagt gaggcaccta tctcagcgat ctgtctattt   1740
cgttcatcca tagttgcctg actccggggg ggggggcgc tgaggtctgc ctcgtgaaga    1800
aggtgttgct gactcatacc aggcctgaat cgccccatca tccagccaga agtgaggga    1860
gccacggttg atgagagctt tgttgtaggt ggaccagttg gtgattttga acttttgctt   1920
tgccacggaa cggtctgcgt tgtcgggaag atgcgtgatc tgatccttca actcagcaaa   1980
agttcgattt attcaacaaa gccgccgtcc cgtcaagtca gcgtaatgct ctgccagtgt   2040
tacaaccaat taaccaattc tgattagaaa aactcatcga gcatcaaatg aaactgcaat   2100
ttattcatat caggattatc aataccatat ttttgaaaaa gccgtttctg taatgaagga   2160
gaaaactcac cgaggcagtt ccataggatg caagatcct ggtatcggtc tgcgattccg     2220
actcgtccaa catcaataca acctattaat ttcccctcgt caaaaataag gttatcaagt   2280
gagaaatcac catgagtgac gactgaatcc ggtgagaatg gcaaaagctt atgcatttct   2340
ttccagactt gttcaacagg ccagccatta cgctcgtcat caaaatcact cgcatcaacc   2400
aaaccgttat tcattcgtga ttgcgcctga gcgagacgaa atacgcgatc gctgttaaaa   2460
ggacaattac aaacaggaat cgaatgcaac cggcgcagga acactgccag cgcatcaaca   2520
atatttcac ctgaatcagg atattcttct aatacctgga atgctgtttt cccggggatc     2580
gcagtggtga gtaaccatgc atcatcagga gtacggataa aatgcttgat ggtcggaaga   2640
ggcataaatt ccgtcagcca gtttagtctg accatctcat ctgtaacatc attggcaacg   2700
ctacctttgc catgtttcag aaacaactct ggcgcatcgg gcttcccata caatcgatag   2760
attgtcgcac ctgattgccc gacattatcg cgagcccatt tatacccata taatcagca    2820
tccatgttgg aatttaatcg cggcctcgag caagacgttt cccgttgaat atggctcata   2880
acaccccttg tattactgtt tatgtaagca gacagtttta ttgttcatga tgatatattt   2940
ttatcttgtg caatgtaaca tcagagattt tgagacacaa cgtggctttc ccccccccc    3000
cattattgaa gcatttatca gggttattgt ctcatgagcg gatacatatt tgaatgtatt   3060
tagaaaaata acaaataggg gttccgcgc acatttcccc gaaaagtgcc acctgacgtc    3120
taagaaacca ttattatcat gacattaacc tataaaaata ggcgtatcac gaggcccttt   3180
cgtc                                                               3184
```

<210> SEQ ID NO 18
<211> LENGTH: 54
<212> TYPE: DNA
<213> ORGANISM: Artificial Sequence
<220> FEATURE:
<223> OTHER INFORMATION: Synthetic: leader sequence

<400> SEQUENCE: 18

```
atgagggtcc ccgctcagct cctggggctc ctgctgctct ggctcccagg tgca        54
```

<210> SEQ ID NO 19
<211> LENGTH: 8
<212> TYPE: DNA
<213> ORGANISM: Artificial Sequence
<220> FEATURE:
<223> OTHER INFORMATION: Synthetic: DraIII restriction site

<400> SEQUENCE: 19

```
cacgatgt                                                            8
```

<210> SEQ ID NO 20
<211> LENGTH: 321
<212> TYPE: DNA
<213> ORGANISM: Artificial Sequence
<220> FEATURE:
<223> OTHER INFORMATION: Synthetic: 225 LC sequence

<400> SEQUENCE: 20

```
gacatcctgc tgacccagtc tccagtcatc ctgtctgtga gtccaggaga aagagtcagt   60
ttctcctgca gggccagtca gagtattggc acaaacatac actggtatca gcaaagaaca  120
aatggttctc caaggcttct cataaagtat gcttctgagt ctatctctgg catcccttcc  180
aggtttagtg gcagtggatc aggacagat tttactctta gcatcaacag tgtggagtct   240
gaagatattg cagattatta ctgtcaacaa ataataact ggccaaccac gttcggtgct    300
gggaccaagc tggagctcaa a                                            321
```

<210> SEQ ID NO 21
<211> LENGTH: 6
<212> TYPE: DNA
<213> ORGANISM: Artificial Sequence
<220> FEATURE:
<223> OTHER INFORMATION: Synthetic: BsiWI restriction site

<400> SEQUENCE: 21

```
cgtacg                                                              6
```

<210> SEQ ID NO 22
<211> LENGTH: 315
<212> TYPE: DNA
<213> ORGANISM: Artificial Sequence
<220> FEATURE:
<223> OTHER INFORMATION: Synthetic: Ckappa sequence

<400> SEQUENCE: 22

```
gtggctgcac catctgtctt catcttcccg ccatctgatg agcagttgaa atctggaact   60
gcctctgttg tgtgcctgct gaataacttc tatcccagag aggccaaagt acagtggaag  120
gtggataacg ccctccaatc gggtaactcc caggagagtg tcacagagca ggacagcaag  180
gacagcacct acagcctcag cagcaccctg acgctgagca agcagacta cgagaaacac   240 aaagtctacg cctgcgaagt cacccatcag ggcctgagct cgcccgtcac aaagagcttc  300
aacaggggag agtgt                                                   315
```

<210> SEQ ID NO 23
<211> LENGTH: 6
<212> TYPE: DNA
<213> ORGANISM: Artificial Sequence
<220> FEATURE:
<223> OTHER INFORMATION: Synthetic: stop sequence

<400> SEQUENCE: 23 taatag                                                                6

<210> SEQ ID NO 24
<211> LENGTH: 6
<212> TYPE: DNA
<213> ORGANISM: Artificial Sequence
<220> FEATURE:
<223> OTHER INFORMATION: Synthetic: GS spacer restriction site

<400> SEQUENCE: 24 ggatca                                                                6

<210> SEQ ID NO 25
<211> LENGTH: 30
<212> TYPE: DNA
<213> ORGANISM: Artificial Sequence
<220> FEATURE:
<223> OTHER INFORMATION: Synthetic: Cmyc Epitope Tag sequence

<400> SEQUENCE: 25
gaacaaaagc ttatttctga agaggacttg                                     30

<210> SEQ ID NO 26
<211> LENGTH: 15
<212> TYPE: PRT
<213> ORGANISM: Artificial Sequence
<220> FEATURE:
<223> OTHER INFORMATION: Synthetic: Linker Sequence

<400> SEQUENCE: 26

Gly Gly Gly Gly Ser Gly Gly Gly Gly Ser Gly Gly Gly Gly Ser
1               5                   10                  15

<210> SEQ ID NO 27
<211> LENGTH: 10
<212> TYPE: PRT
<213> ORGANISM: Artificial Sequence
<220> FEATURE:
<223> OTHER INFORMATION: Synthetic: Linker Sequence

<400> SEQUENCE: 27

Gly Gly Gly Gly Ser Gly Gly Gly Gly Ser
1               5                   10

<210> SEQ ID NO 28
<211> LENGTH: 5
<212> TYPE: PRT
<213> ORGANISM: Artificial Sequence
<220> FEATURE:
<223> OTHER INFORMATION: Synthetic: Linker Sequence

<400> SEQUENCE: 28

Gly Gly Gly Gly Ser
1               5

<210> SEQ ID NO 29
<211> LENGTH: 7223

```
<212> TYPE: DNA
<213> ORGANISM: Artificial Sequence
<220> FEATURE:
<223> OTHER INFORMATION: Synthetic construct: gWiz BS28-HN

<400> SEQUENCE: 29
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtt cggggctggc ttaactatgc ggcatcagag cagattgtac tgagagtgca     180
ccatatgcgg tgtgaaatac cgcacagatg cgtaaggaga aaataccgca tcagattggc     240
tattggccat tgcatacgtt gtatccatat cataatatgt acatttatat tggctcatgt     300
ccaacattac cgccatgttg acattgatta ttgactagtt attaatagta atcaattacg     360
gggtcattag ttcatagccc atatatggag ttccgcgtta cataacttac ggtaaatggc     420
ccgcctggct gaccgcccaa cgacccccgc ccattgacgt caataatgac gtatgttccc     480
atagtaacgc caatagggac tttccattga cgtcaatggg tggagtattt acggtaaact     540
gcccacttgg cagtacatca agtgtatcat atgccaagta cgccccctat tgacgtcaat     600
gacggtaaat ggcccgcctg gcattatgcc cagtacatga ccttatggga ctttcctact     660
tggcagtaca tctacgtatt agtcatcgct attaccatgg tgatgcggtt ttggcagtac     720
atcaatgggc gtggatagcg gtttgactca cggggatttc caagtctcca ccccattgac     780
gtcaatggga gtttgttttg gcaccaaaat caacgggact ttccaaaatg tcgtaacaac     840
tccgccccat tgacgcaaat gggcggtagg cgtgtacggt gggaggtcta tataagcaga     900
gctcgtttag tgaaccgtca gatcgcctgg agacgccatc cacgctgttt tgacctccat     960
agaagacacc gggaccgatc cagcctccgc ggccgggaac ggtgcattgg aacgcggatt    1020
ccccgtgcca agagtgacgt aagtaccgcc tatagactct ataggcacac ccctttggct    1080
cttatgcatg ctatactgtt tttggcttgg ggcctataca ccccccgcttc cttatgctat    1140
aggtgatggt atagcttagc ctataggtgt gggttattga ccattattga ccactcccct    1200
attggtgacg atactttcca ttactaatcc ataacatggc tctttgccac aactatctct    1260
attggctata tgccaatact ctgtccttca gagactgaca cggactctgt attttttacag    1320
gatggggtcc catttattat ttacaaattc acatatacaa caacgccgtc ccccgtgccc    1380
gcagttttta ttaaacatag cgtgggatct ccacgcgaat ctcgggtacg tgttccggac    1440
atgggctctt ctccggtagc ggcggagctt ccacatccga gccctggtcc catgcctcca    1500
gcggctcatg gtcgctcggc agctccttgc tcctaacagt ggaggccaga cttaggcaca    1560
gcacaatgcc caccaccacc agtgtgccgc acaaggccgt ggcggtaggg tatgtgtctg    1620
aaaatgagcg tggagattgg gctcgcacgg ctgacgcaga tggaagactt aaggcagcgg    1680
cagaagaaga tgcaggcagc tgagttgttg tattctgata agagtcagag gtaactcccg    1740
ttgcggtgct gttaacggtg agggcagtg tagtctgagc agtactcgtt gctgccgcgc    1800
gcgccaccag acataatagc tgacagacta acagactgtt cctttccatg ggtctttttct    1860
gcaggccgcc accatgggtt ggagcctcat cttgctcttc cttgtcgctg ttgctcatat    1920
ggctagccag cttcaggagt cgggacctag cctggtgaaa ccttctcagt ctctgtccct    1980
cacctgcact gtcactggct actcaatcac cagtgatttt gcctggaact ggatccggca    2040
gtttccagga aacaagctgg agtggatggg ctacataagt tatagtggta acactaggta    2100
caacccatct ctcaaaagtc gaatctctat cactcgagac acatccaaga accaattctt    2160
```

```
cctgcagttg aattctgtga ctattgagga cacagccaca tattactgtg taacggcggg    2220
acgcgggttt ccttattggg gccaagggac tctggtcact gtctctgcag gaggcggcgg    2280
atctggcggt ggaggttctg gcggcggcgg atctgacatc ctgatgaccc aatctccatc    2340
ctccatgtct gtatctctgg gagacacagt cagcatcact tgccattcaa gtcaggacat    2400
taacagtaat ataggtggt tgcagcagag accagggaaa tcatttaagg gcctgatcta    2460
tcatggaacc aacttggacg atgaagttcc atcaaggttc agtggcagtg gatctggagc    2520
cgattattct ctcaccatca gcagcctgga atctgaagat tttgcagact attactgtgt    2580
acagtatgct cagtttccgt ggacgttcgg tggaggcacc aagctggaaa tcaaacgtgg    2640
atccggaggt ggcggtagtg gcggaggtgg ttctacgcgt caggtacaac tgaagcagtc    2700
aggacctggc ctagtgcagc cctcacagag cctgtccatc acctgcacag tctctggttt    2760
ctcattaact aactatggtg tacactgggt tcgccagtct ccaggaaagg gtctggagtg    2820
gctgggagtg atatgagtg gtggaaacac agactataat acacctttca catccagact    2880
gagcatcaac aaggacaatt ccaagagcca agttttcttt aaaatgaaca gtctgcaatc    2940
taatgacaca gccatatatt actgtgccag agccctcacc tactatgatt acgagtttgc    3000
ttactggggc caagggaccc tggtcaccgt ttccgctgct agcaccaagg gcccatcggt    3060
cttccccctg gcaccctcct ccaagagcac ctctgggggc acagcggccc tgggctgcct    3120
ggtcaaggac tacttccccg aaccggtgac ggtgtcgtgg aactcaggcg ccctgaccag    3180
cggcgtgcac accttcccgg ctgtcctaca gtcctcagga ctctactccc tcagcagcgt    3240
ggtgaccgtg ccctccagca gcttgggcac ccagacctac atctgcaacg tgaatcacaa    3300
gcccagcaac accaaggtgg acaagaaagt tgagcccaaa tcttgtgaca aaactcacac    3360
atgcccaccg tgcccagcac ctgaactcct ggggggaccg tcagtcttcc tcttcccccc    3420
aaaacccaag gacaccctca tgatctcccg gacccctgag gtcacatgcg tggtggtgga    3480
cgtgagccac gaagaccctg aggtcaagtt caactggtac gtggacggcg tggaggtgca    3540
taatgccaag acaaagccgc gggaggagca gtacaacagc acgtaccgtg tggtcagcgt    3600
cctcaccgtc ctgcaccagg actggctgaa tggcaaggag tacaagtgca aggtctccaa    3660
caaagccctc ccagccccca tcgagaaaac catctccaaa gccaaagggc agccccgaga    3720
accacaggtg tacaccctgc ccccatcccg ggatgagctg accaagaacc aggtcagcct    3780
gacctgcctg gtcaaaggct tctatcccag cgacatcgcc gtggagtggg agagcaatgg    3840
gcagccggag aacaactaca agaccacgcc tcccgtgctg gactccgacg gctccttctt    3900
cctctacagc aagctcaccg tggacaagag caggtggcag caggggaacg tcttctcatg    3960
ctccgtgatg catgaggctc tgcacaacca ctacacgcag aagagcctct ccctgtctcc    4020
gggtaaatga taagtcgaca cgtgtgatca gatatcgcgg ccgctctaga ccaggcgcct    4080
ggatccagat cacttctggc taataaaaga tcagagctct agagatctgt gtgttggttt    4140
tttgtggatc tgctgtgcct tctagttgcc agccatctgt tgtttgcccc tccccgtgc    4200 cttccttgac cctggaaggt gccactccca ctgtcctttc ctaataaaat gaggaaattg    4260
catcgcattg tctgagtagg tgtcattcta ttctgggggg tggggtgggg cagcacagca    4320
agggggagga ttgggaagac aatagcaggc atgctgggga tgcggtgggc tctatgggta    4380
cctctctctc tctctctctc tctctctctc tctctctctc tcggtacctc tctctctctc    4440
tctctctctc tctctctctc tctctctcgg taccaggtgc tgaagaattg acccggttcc    4500
tcctgggcca gaaagaagca ggcacatccc cttctctgtg acacaccctg tccacgcccc    4560
```

```
tggttcttag ttccagcccc actcatagga cactcatagc tcaggagggc tccgccttca   4620
atcccacccg ctaaagtact tggagcggtc tctccctccc tcatcagccc accaaaccaa   4680
acctagcctc caagagtggg aagaaattaa agcaagatag gctattaagt gcagagggag   4740
agaaaatgcc tccaacatgt gaggaagtaa tgagagaaat catagaattt cttccgcttc   4800
ctcgctcact gactcgctgc gctcggtcgt tcggctgcgg cgagcggtat cagctcactc   4860
aaaggcggta atacggttat ccacagaatc aggggataac gcaggaaaga acatgtgagc   4920
aaaaggccag caaaaggcca ggaaccgtaa aaaggccgcg ttgctggcgt ttttccatag   4980
gctccgcccc cctgacgagc atcacaaaaa tcgacgctca agtcagaggt ggcgaaaccc   5040
gacaggacta taaagatacc aggcgtttcc ccctggaagc tccctcgtgc gctctcctgt   5100
tccgaccctg ccgcttaccg gatacctgtc cgcctttctc ccttcgggaa gcgtggcgct   5160
ttctcaatgc tcacgctgta ggtatctcag ttcggtgtag gtcgttcgct ccaagctggg   5220
ctgtgtgcac gaaccccccg ttcagcccga ccgctgcgcc ttatccggta actatcgtct   5280
tgagtccaac ccggtaagac acgacttatc gccactggca gcagccactg gtaacaggat   5340
tagcagagcg aggtatgtag gcggtgctac agagttcttg aagtggtggc ctaactacgg   5400
ctacactaga aggacagtat ttggtatctg cgctctgctg aagccagtta ccttcggaaa   5460
aagagttggt agctcttgat ccggcaaaca aaccaccgct ggtagcggtg gtttttttgt   5520
ttgcaagcag cagattacgc gcagaaaaaa aggatctcaa gaagatcctt tgatcttttc   5580
tacggggtct gacgctcagt ggaacgaaaa ctcacgttaa gggattttgg tcatgagatt   5640
atcaaaaagg atcttcacct agatcctttt aaattaaaaa tgaagtttta aatcaatcta   5700
aagtatatat gagtaaactt ggtctgacag ttaccaatgc ttaatcagtg aggcaccta   5760 ctcagcgatc tgtctatttc gttcatccat agttgcctga ctccgggggg gggggcgct   5820 gaggtctgcc tcgtgaagaa ggtgttgctg actcatacca ggcctgaatc gccccatcat   5880
ccagccagaa agtgagggag ccacggttga tgagagcttt gttgtaggtg gaccagttgg   5940
tgattttgaa cttttgcttt gccacggaac ggtctgcgtt gtcggaaga tgcgtgatct   6000 gatccttcaa ctcagcaaaa gttcgattta ttcaacaaag ccgccgtccc gtcaagtcag   6060
cgtaatgctc tgccagtgtt acaaccaatt aaccaattct gattagaaaa actcatcgag   6120
catcaaatga aactgcaatt tattcatatc aggattatca ataccatatt tttgaaaaag   6180
ccgtttctgt aatgaaggag aaaactcacc gaggcagttc cataggatgg caagatcctg   6240
gtatcggtct gcgattccga ctcgtccaac atcaatacaa cctattaatt tcccctcgtc   6300
aaaaataagg ttatcaagtg agaaatcacc atgagtgacg actgaatccg gtgagaatgg   6360
caaaagctta tgcatttctt tccagacttg ttcaacaggc cagccattac gctcgtcatc   6420
aaaatcactc gcatcaacca accgttatt cattcgtgat tgcgcctgag cgagacgaaa   6480
tacgcgatcg ctgttaaaag gacaattaca aacaggaatc gaatgcaacc ggcgcaggaa   6540
cactgccagc gcatcaacaa tattttcacc tgaatcagga tattcttcta atacctggaa   6600
tgctgttttc ccggggatcg cagtggtgag taaccatgca tcatcaggag tacggataaa   6660
atgcttgatg gtcggaagag gcataaattc cgtcagccag tttagtctga ccatctcatc   6720
tgtaacatca ttggcaacgc tacctttgcc atgtttcaga aacaactctg gcgcatcggg   6780
cttcccatac aatcgataga ttgtcgcacc tgattgcccg acattatcgc gagcccattt   6840
atacccatat aaatcagcat ccatgttgga atttaatcgc ggcctcgagc aagacgtttc   6900
```

-continued

```
ccgttgaata tggctcataa caccccttgt attactgttt atgtaagcag acagttttat    6960
tgttcatgat gatatatttt tatcttgtgc aatgtaacat cagagatttt gagacacaac    7020
gtggctttcc cccccccccc attattgaag catttatcag ggttattgtc tcatgagcgg    7080
atacatattt gaatgtattt agaaaaataa acaaataggg gttccgcgca catttccccg    7140
aaaagtgcca cctgacgtct aagaaaccat tattatcatg acattaacct ataaaaatag    7200
gcgtatcacg aggccctttc gtc                                            7223
```

<210> SEQ ID NO 30
<211> LENGTH: 7205
<212> TYPE: DNA
<213> ORGANISM: Artificial Sequence
<220> FEATURE:
<223> OTHER INFORMATION: Synthetic construct: gWiz BS28-HC

<400> SEQUENCE: 30

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtt cggggctggc ttaactatgc ggcatcagag cagattgtac tgagagtgca     180
ccatatgcgg tgtgaaatac cgcacagatg cgtaaggaga aaataccgca tcagattggc     240
tattggccat tgcatacgtt gtatccatat cataatatgt acatttatat tggctcatgt     300
ccaacattac cgccatgttg acattgatta ttgactagtt attaatagta atcaattacg     360
gggtcattag ttcatagccc atatatggag ttccgcgtta cataacttac ggtaaatggc     420
ccgcctggct gaccgcccaa cgaccccgc ccattgacgt caataatgac gtatgttccc      480
atagtaacgc caatagggac tttccattga cgtcaatggg tggagtattt acggtaaact     540
gcccacttgg cagtacatca agtgtatcat atgccaagta cgccccctat tgacgtcaat     600
gacggtaaat ggcccgcctg gcattatgcc cagtacatga ccttatggga ctttcctact     660
tggcagtaca tctacgtatt agtcatcgct attaccatgg tgatgcggtt ttggcagtac     720
atcaatgggc gtggatagcg gtttgactca cggggatttc caagtctcca ccccattgac     780
gtcaatggga gtttgttttg gcaccaaaat caacgggact ttccaaaatg tcgtaacaac     840
tccgccccat tgacgcaaat gggcggtagg cgtgtacggt gggaggtcta tataagcaga     900
gctcgtttag tgaaccgtca gatcgcctgg agacgccatc cacgctgttt tgacctccat     960
agaagacacc gggaccgatc cagcctccgc ggccgggaac ggtgcattgg aacgcggatt    1020
ccccgtgcca agagtgacgt aagtaccgcc tatagactct ataggcacac ccctttggct    1080
cttatgcatg ctatactgtt tttggcttgg ggcctataca ccccgcttc cttatgctat     1140 aggtgatggt atagcttagc ctataggtgt gggttattga ccattattga ccactcccct    1200
attggtgacg atactttcca ttactaatcc ataacatggc tctttgccac aactatctct    1260
attggctata tgccaatact ctgtccttca gagactgaca cggactctgt atttttacag    1320 gatgggtcc catttattat ttacaaattc acatatacaa caacgccgtc ccccgtgccc     1380
gcagttttta ttaaacatag cgtgggatct ccacgcgaat ctcgggtacg tgttccggac    1440
atgggctctt ctccggtagc ggcggagctt ccacatccga gccctggtcc catgcctcca    1500
gcggctcatg gtcgctcggc agctccttgc tcctaacagt ggaggccaga cttaggcaca    1560
gcacaatgcc caccaccacc agtgtgccgc acaaggccgt ggcggtaggg tatgtgtctg    1620
aaaatgagcg tggagattgg gctcgcacgg ctgacgcaga tggaagactt aaggcagcgg    1680
cagaagaaga tgcaggcagc tgagttgttg tattctgata agagtcagag gtaactcccg    1740
```

```
ttgcggtgct gttaacggtg gagggcagtg tagtctgagc agtactcgtt gctgccgcgc   1800
gcgccaccag acataatagc tgacagacta acagactgtt cctttccatg ggtcttttct   1860
gcaggccgcc accatgggtt ggagcctcat cttgctcttc cttgtcgctg ttgctacgcg   1920
tcaggtacaa ctgaagcagt caggacctgg cctagtgcag ccctcacaga gcctgtccat   1980
cacctgcaca gtctctggtt tctcattaac taactatggt gtacactggg ttcgccagtc   2040
tccaggaaag ggtctggagt ggctgggagt gatatggagt ggtggaaaca cagactataa   2100
tacacctttc acatccagac tgagcatcaa caaggacaat tccaagagcc aagttttctt   2160
taaaatgaac agtctgcaat ctaatgacac agccatatat tactgtgcca gagccctcac   2220
ctactatgat tacgagtttg cttactgggg ccaagggacc ctggtcaccg tttccgctgc   2280
tagcaccaag ggcccatcgg tcttccccct ggcaccctcc tccaagagca cctctggggg   2340
cacagcggcc ctgggctgcc tggtcaagga ctacttcccc gaaccggtga cggtgtcgtg   2400
gaactcaggc gccctgacca gcggcgtgca caccttcccg gctgtcctac agtcctcagg   2460
actctactcc ctcagcagcg tggtgaccgt gccctccagc agcttgggca cccagaccta   2520
catctgcaac gtgaatcaca agcccagcaa caccaaggtg gacaagaaag ttgagcccaa   2580
atcttgtgac aaaactcaca catgcccacc gtgcccagca cctgaactcc tggggggacc   2640
gtcagtcttc ctcttccccc caaaacccaa ggacaccctc atgatctccc ggacccctga   2700
ggtcacatgc gtggtggtgg acgtgagcca cgaagaccct gaggtcaagt tcaactggta   2760
cgtggacggc gtggaggtgc ataatgccaa gacaaagccg cgggaggagc agtacaacag   2820
cacgtaccgt gtggtcagcg tcctcaccgt cctgcaccag gactggctga atggcaagga   2880
gtacaagtgc aaggtctcca acaaagccct cccagccccc atcgagaaaa ccatctccaa   2940
agccaaaggg cagccccgag aaccacaggt gtacaccctg cccccatccc gggatgagct   3000
gaccaagaac caggtcagcc tgacctgcct ggtcaaaggc ttctatccca gcgacatcgc   3060
cgtggagtgg gagagcaatg ggcagccgga gaacaactac aagaccacgc ctcccgtgct   3120
ggactccgac ggctccttct tcctctacag caagctcacc gtggacaaga gcaggtggca   3180
gcaggggaac gtcttctcat gctccgtgat gcatgaggct ctgcacaacc actacacgca   3240
gaagagcctc tccctgtctc cgggtaaagg aggtggcggt agtggcggag gtggttctca   3300
gcttcaggag tcgggaccta gcctggtgaa accttctcag tctctgtccc tcacctgcac   3360
tgtcactggc tactcaatca ccagtgattt tgcctggaac tggatccggc agtttccagg   3420
aaacaagctg gagtggatgg gctacataag ttatagtggt aacactaggt acaacccatc   3480
tctcaaaagt cgaatctcta tcactcgaga cacatccaag aaccaattct tcctgcagtt   3540
gaattctgtg actattgagg acacagccac atattactgt gtaacggcgg acgcgggtt   3600 tccttattgg ggccaaggga ctctggtcac tgtctctgca ggaggcggcg gatctggcgg   3660
tggaggttct ggcggcggcg gatctgacat cctgatgacc caatctccat cctccatgtc   3720
tgtatctctg ggagacacag tcagcatcac ttgccattca agtcaggaca ttaacagtaa   3780 tataggtgg ttgcagcaga gaccagggaa atcatttaag gcctgatct atcatggaac   3840 caacttggac gatgaagttc catcaaggtt cagtggcagt ggatctggag ccgattattc   3900
tctcaccatc agcagcctgg aatctgaaga ttttgcagac tattactgtg tacagtatgc   3960
tcagtttccg tggacgttcg gtggaggcac caagctggaa atcaaacgtt gataagtcga   4020
cacgtgtgat cagatatcgc ggccgctcta gaccaggcgc ctggatccag atcacttctg   4080
```

-continued

```
gctaataaaa gatcagagct ctagagatct gtgtgttggt tttttgtgga tctgctgtgc    4140
cttctagttg ccagccatct gttgtttgcc cctcccccgt gccttccttg accctggaag    4200
gtgccactcc cactgtcctt tcctaataaa atgaggaaat tgcatcgcat tgtctgagta    4260
ggtgtcattc tattctgggg ggtggggtgg ggcagcacag caaggggag gattgggaag     4320 acaatagcag gcatgctggg gatgcggtgg gctctatggg tacctctctc tctctctctc    4380
tctctctctc tctctctctc tctcggtacc tctctctctc tctctctctc tctctctctc    4440
tctctctctc ggtaccaggt gctgaagaat tgacccggtt cctcctgggc cagaaagaag    4500
caggcacatc cccttctctg tgacacaccc tgtccacgcc cctggttctt agttccagcc    4560
ccactcatag gacactcata gctcaggagg gctccgcctt caatcccacc cgctaaagta    4620
cttggagcgg tctctccctc cctcatcagc ccaccaaacc aaacctagcc tccaagagtg    4680
ggaagaaatt aaagcaagat aggctattaa gtgcagaggg agagaaaatg cctccaacat    4740
gtgaggaagt aatgagagaa atcatagaat ttcttccgct tcctcgctca ctgactcgct    4800
gcgctcggtc gttcggctgc ggcgagcggt atcagctcac tcaaaggcgg taatacggtt    4860
atccacagaa tcaggggata acgcaggaaa gaacatgtga gcaaaaggcc agcaaaaggc    4920
caggaaccgt aaaaaggccg cgttgctggc gtttttccat aggctccgcc ccctgacga    4980 gcatcacaaa aatcgacgct caagtcagag gtggcgaaac ccgacaggac tataaagata    5040
ccaggcgttt ccccctggaa gctccctcgt gcgctctcct gttccgaccc tgccgcttac    5100
cggatacctg tccgcctttc tcccttcggg aagcgtggcg ctttctcaat gctcacgctg    5160
taggtatctc agttcggtgt aggtcgttcg ctccaagctg ggctgtgtgc acgaaccccc    5220
cgttcagccc gaccgctgcg ccttatccgg taactatcgt cttgagtcca acccggtaag    5280
acacgactta tcgccactgg cagcagccac tggtaacagg attagcagag cgaggtatgt    5340
aggcggtgct acagagttct tgaagtggtg gcctaactac ggctacacta aggacagt     5400 atttggtatc tgcgctctgc tgaagccagt taccttcgga aaaagagttg gtagctcttg    5460
atccggcaaa caaaccaccg ctggtagcgg tggtttttt gtttgcaagc agcagattac     5520
gcgcagaaaa aaaggatctc aagaagatcc tttgatcttt tctacggggt ctgacgctca    5580
gtggaacgaa aactcacgtt aagggatttt ggtcatgaga ttatcaaaaa ggatcttcac    5640
ctagatcctt ttaaattaaa aatgaagttt taaatcaatc taaagtatat atgagtaaac    5700
ttggtctgac agttaccaat gcttaatcag tgaggcacct atctcagcga tctgtctatt    5760
tcgttcatcc atagttgcct gactccgggg ggggggggcg ctgaggtctg cctcgtgaag    5820
aaggtgttgc tgactcatac caggcctgaa tcgccccatc atccagccag aaagtgaggg    5880
agccacggtt gatgagagct tgttgtagg tggaccagtt ggtgattttg aacttttgct    5940
ttgccacgga acggtctgcg ttgtcgggaa gatgcgtgat ctgatccttc aactcagcaa    6000
aagttcgatt tattcaacaa agccgccgtc ccgtcaagtc agcgtaatgc tctgccagtg    6060
ttacaaccaa ttaaccaatt ctgattagaa aaactcatcg agcatcaaat gaaactgcaa    6120
tttattcata tcaggattat caataccata ttttgaaaa agccgtttct gtaatgaagg    6180
agaaaactca ccgaggcagt tccataggat ggcaagatcc tggtatcggt ctgcgattcc    6240
gactcgtcca acatcaatac aacctattaa tttcccctcg tcaaaataa ggttatcaag     6300 tgagaaatca ccatgagtga cgactgaatc cggtgagaat ggcaaaagct tatgcatttc    6360
tttccagact tgttcaacag gccagccatt acgctcgtca tcaaaatcac tcgcatcaac    6420
caaaccgtta ttcattcgtg attgcgcctg agcgagacga atacgcgat cgctgttaaa     6480
```

```
aggacaatta caaacaggaa tcgaatgcaa ccggcgcagg aacactgcca gcgcatcaac    6540
aatattttca cctgaatcag gatattcttc taatacctgg aatgctgttt tcccggggat    6600
cgcagtggtg agtaaccatg catcatcagg agtacggata aaatgcttga tggtcggaag    6660
aggcataaat tccgtcagcc agtttagtct gaccatctca tctgtaacat cattggcaac    6720
gctacctttg ccatgtttca gaaacaactc tggcgcatcg ggcttcccat acaatcgata    6780
gattgtcgca cctgattgcc cgacattatc gcgagcccat ttatacccat ataaatcagc    6840
atccatgttg gaatttaatc gcggcctcga gcaagacgtt tcccgttgaa tatggctcat    6900 aacaccccctt gtattactgt ttatgtaagc agacagtttt attgttcatg atgatatatt    6960
tttatcttgt gcaatgtaac atcagagatt ttgagacaca acgtggcttt ccccccccc    7020 ccattattga agcatttatc agggttattg tctcatgagc ggatacatat ttgaatgtat    7080
ttagaaaaat aaacaaatag gggttccgcg cacatttccc cgaaaagtgc cacctgacgt    7140
ctaagaaacc attattatca tgacattaac ctataaaaat aggcgtatca cgaggccctt    7200
tcgtc                                                                7205

<210> SEQ ID NO 31
<211> LENGTH: 6533
<212> TYPE: DNA
<213> ORGANISM: Artificial Sequence
<220> FEATURE:
<223> OTHER INFORMATION: Synthetic construct: gWiz BS28-LN

<400> SEQUENCE: 31
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtt cggggctggc ttaactatgc ggcatcagag cagattgtac tgagagtgca     180
ccatatgcgg tgtgaaatac cgcacagatg cgtaaggaga aaataccgca tcagattggc     240
tattggccat tgcatacgtt gtatccatat cataatatgt acatttatat ggctcatgt      300 ccaacattac cgccatgttg acattgatta ttgactagtt attaatagta atcaattacg     360
gggtcattag ttcatagccc atatatggag ttccgcgtta cataacttac ggtaaatggc     420
ccgcctggct gaccgcccaa cgaccccccgc ccattgacgt caataatgac gtatgttccc     480
atagtaacgc caatagggac tttccattga cgtcaatggg tggagtattt acggtaaact     540
gcccacttgg cagtacatca agtgtatcat atgccaagta cgccccctat tgacgtcaat     600
gacggtaaat ggcccgcctg gcattatgcc cagtacatga ccttatggga ctttcctact     660
tggcagtaca tctacgtatt agtcatcgct attaccatgg tgatgcggtt ttggcagtac     720
atcaatgggc gtggatagcg gtttgactca cggggatttc caagtctcca ccccattgac     780
gtcaatggga gtttgttttg gcaccaaaat caacgggact ttccaaaatg tcgtaacaac     840
tccgccccat tgacgcaaat gggcggtagg cgtgtacggt gggaggtcta taagcagga     900 gctcgtttag tgaaccgtca gatcgcctgg agacgccatc cacgctgttt tgacctccat     960
agaagacacc gggaccgatc cagcctccgg ggcgggaac ggtgcattgg aacgcggatt    1020
ccccgtgcca agagtgacgt aagtaccgcc tatagactct ataggcacac ccctttggct    1080
cttatgcatg ctatactgtt tttggcttgg ggcctataca cccccgcttc cttatgctat    1140
aggtgatggt atagcttagc ctataggtgt gggttattga ccattattga ccactcccct    1200
attggtgacg atactttcca ttactaatcc ataacatggc tctttgccac aactatctct    1260
```

```
attggctata tgccaatact ctgtccttca gagactgaca cggactctgt attttttacag    1320 gatggggtcc catttattat ttacaaattc acatatacaa caacgccgtc ccccgtgccc    1380
gcagttttta ttaaacatag cgtgggatct ccacgcgaat ctcgggtacg tgttccggac    1440
atgggctctt ctccggtagc ggcggagctt ccacatccga gccctggtcc catgcctcca    1500
gcggctcatg gtcgctcggc agctccttgc tcctaacagt ggaggccaga cttaggcaca    1560
gcacaatgcc caccaccacc agtgtgccgc acaaggccgt ggcggtaggg tatgtgtctg    1620
aaaatgagcg tggagattgg gctcgcacgg ctgacgcaga tggaagactt aaggcagcgg    1680
cagaagaaga tgcaggcagc tgagttgttg tattctgata agagtcagag gtaactcccg    1740
ttgcggtgct gttaacggtg gagggcagtg tagtctgagc agtactcgtt gctgccgcgc    1800
gcgccaccag acataatagc tgacagacta acagactgtt cctttccatg ggtcttttct    1860
gcaggccgcc accatgaggg tccccgctca gctcctgggg ctcctgctgc tctggctccc    1920
aggtgcacat atggctagcc agcttcagga gtcgggacct agcctggtga aaccttctca    1980
gtctctgtcc ctcacctgca ctgtcactgg ctactcaatc accagtgatt ttgcctggaa    2040
ctggatccgg cagtttccag gaaacaagct ggagtggatg ggctacataa gttatagtgg    2100
taacactagg tacaacccat ctctcaaaag tcgaatctct atcactcgag acacatccaa    2160
gaaccaattc ttcctgcagt tgaattctgt gactattgag acacagccca catattactg    2220
tgtaacggcg ggacgcgggt ttccttattg gggccaaggg actctggtca ctgtctctgc    2280
aggaggcggc ggatctggcg gtggaggttc tggcggcggc ggatctgaca tcctgatgac    2340
ccaatctcca tcctccatgt ctgtatctct gggagacaca gtcagcatca cttgccattc    2400
aagtcaggac attaacagta atataggggtg gttgcagcag agaccaggga aatcatttaa    2460
gggcctgatc tatcatggaa ccaacttgga cgatgaagtt ccatcaaggt tcagtggcag    2520
tggatctgga gccgattatt ctctcaccat cagcagcctg gaatctgaag attttgcaga    2580
ctattactgt gtacagtatg ctcagttttcc gtggacgttc ggtggaggca ccaagctgga    2640
aatcaaacgt ggatccggag gtggcggtag tggcggaggt ggttcttcac gatgtgacat    2700
cctgctgacc cagtctccag tcatcctgtc tgtgagtcca ggagaaagag tcagtttctc    2760
ctgcagggcc agtcagagta ttggcacaaa catacactgg tatcagcaaa gaacaaatgg    2820
ttctccaagg cttctcataa agtatgcttc tgagtctatc tctggcatcc cttccaggtt    2880
tagtggcagt ggatcaggga cagattttac tcttagcatc aacagtgtgg agtctgaaga    2940
tattgcagat tattactgtc aacaaaataa taactggcca accacgttcg gtgctgggac    3000
caagctggag ctcaaacgta cggtggctgc accatctgtc ttcatcttcc cgccatctga    3060
tgagcagttg aaatctggaa ctgcctctgt tgtgtgcctg ctgaataact tctatcccag    3120
agaggccaaa gtacagtgga aggtggataa cgccctccaa tcgggtaact cccaggagag    3180
tgtcacagag caggacagca aggacagcac ctacagcctc agcagcaccc tgacgctgag    3240
caaagcagac tacgagaaac acaaagtcta cgcctgcgaa gtcacccatc agggcctgag    3300
ctcgcccgtc acaaagagct tcaacagggg agagtgttaa taggtcgaca cgtgtgatca    3360
gatatcgcgg ccgctctaga ccaggcgcct ggatccagat cacttctggc taataaaaga    3420
tcagagctct agagatctgt gtgttggttt tttgtggatc tgctgtgcct tctagttgcc    3480
agccatctgt tgtttgcccc tccccgtgcc cttccttgac cctggaaggt gccactccca    3540
ctgtcctttc ctaataaaat gaggaaattg catcgcattg tctgagtagg tgtcattcta    3600
ttctgggggg tggggtgggg cagcacagca aggggagga ttgggaagac aatagcaggc    3660
```

```
atgctgggga tgcggtgggc tctatgggta cctctctctc tctctctctc tctctctctc  3720
tctctctctc tcggtacctc tctctctctc tctctctctc tctctctctc tctctctcgg  3780
taccaggtgc tgaagaattg acccggttcc tcctgggcca gaaagaagca ggcacatccc  3840
cttctctgtg acacaccctg tccacgcccc tggttcttag ttccagcccc actcatagga  3900
cactcatagc tcaggagggc tccgccttca atcccacccg ctaaagtact tggagcggtc  3960
tctccctccc tcatcagccc accaaaccaa acctagcctc caagagtggg aagaaattaa  4020
agcaagatag gctattaagt gcagagggag agaaaatgcc tccaacatgt gaggaagtaa  4080
tgagagaaat catagaattt cttccgcttc ctcgctcact gactcgctgc gctcggtcgt  4140
tcggctgcgg cgagcggtat cagctcactc aaaggcggta atacggttat ccacagaatc  4200
aggggataac gcaggaaaga acatgtgagc aaaaggccag caaaaggcca ggaaccgtaa  4260
aaaggccgcg ttgctggcgt ttttccatag gctccgcccc cctgacgagc atcacaaaaa  4320
tcgacgctca agtcagaggt ggcgaaaccc gacaggacta taaagatacc aggcgtttcc  4380
ccctggaagc tccctcgtgc gctctcctgt tccgaccctg ccgcttaccg gatacctgtc  4440
cgcctttctc ccttcgggaa gcgtggcgct ttctcaatgc tcacgctgta ggtatctcag  4500
ttcggtgtag gtcgttcgct ccaagctggg ctgtgtgcac gaaccccccg ttcagcccga  4560
ccgctgcgcc ttatccggta actatcgtct tgagtccaac ccggtaagac acgacttatc  4620
gccactggca gcagccactg gtaacaggat tagcagagcg aggtatgtag gcggtgctac  4680
agagttcttg aagtggtggc ctaactacgg ctacactaga aggacagtat ttggtatctg  4740
cgctctgctg aagccagtta ccttcggaaa aagagttggt agctcttgat ccggcaaaca  4800
aaccaccgct ggtagcggtg gtttttttgt ttgcaagcag cagattacgc gcagaaaaaa  4860
aggatctcaa gaagatcctt tgatcttttc tacggggtct gacgctcagt ggaacgaaaa  4920
ctcacgttaa gggattttgg tcatgagatt atcaaaaagg atcttcacct agatcctttt  4980
aaattaaaaa tgaagtttta atcaatcta aagtatatat gagtaaactt ggtctgacag  5040
ttaccaatgc ttaatcagtg aggcacctat ctcagcgatc tgtctatttc gttcatccat  5100
agttgcctga ctccggggg gggggcgct gaggtctgcc tcgtgaagaa ggtgttgctg  5160
actcatacca ggcctgaatc gccccatcat ccagccagaa agtgagggag ccacggttga  5220
tgagagcttt gttgtaggtg gaccagttgg tgattttgaa cttttgcttt gccacggaac  5280
ggtctgcgtt gtcgggaaga tgcgtgatct gatccttcaa ctcagcaaaa gttcgattta  5340
ttcaacaaag ccgccgtccc gtcaagtcag cgtaatgctc tgccagtgtt acaaccaatt  5400
aaccaattct gattagaaaa actcatcgag catcaaatga aactgcaatt tattcatatc  5460
aggattatca ataccatatt tttgaaaaag ccgtttctgt aatgaaggag aaaactcacc  5520
gaggcagttc cataggatgg caagatcctg gtatcggtct gcgattccga ctcgtccaac  5580
atcaatacaa cctattaatt tcccctcgtc aaaaataagg ttatcaagtg agaaatcacc  5640
atgagtgacg actgaatccg gtgagaatgg caaaagctta tgcatttctt tccagacttg  5700
ttcaacaggc cagccattac gctcgtcatc aaaatcactc gcatcaacca aaccgttatt  5760
cattcgtgat tgcgcctgag cgagacgaaa tacgcgatcg ctgttaaaag gacaattaca  5820
aacaggaatc gaatgcaacc ggcgcaggaa cactgccagc gcatcaacaa tattttcacc  5880
tgaatcagga tattcttcta atacctggaa tgctgttttc ccggggatcg cagtggtgag  5940
taaccatgca tcatcaggag tacggataaa atgcttgatg gtcggaagag gcataaattc  6000
```

```
cgtcagccag tttagtctga ccatctcatc tgtaacatca ttggcaacgc tacctttgcc    6060
atgtttcaga aacaactctg gcgcatcggg cttcccatac aatcgataga ttgtcgcacc    6120
tgattgcccg acattatcgc gagcccattt atacccatat aaatcagcat ccatgttgga    6180
atttaatcgc ggcctcgagc aagacgtttc ccgttgaata tggctcataa cacccccttgt   6240 attactgttt atgtaagcag acagttttat tgttcatgat gatatatttt tatcttgtgc    6300
aatgtaacat cagagatttt gagacacaac gtggctttcc ccccccccc attattgaag     6360 catttatcag ggttattgtc tcatgagcgg atacatattt gaatgtattt agaaaaataa    6420
acaaataggg gttccgcgca catttccccg aaaagtgcca cctgacgtct aagaaaccat    6480
tattatcatg acattaacct ataaaaatag gcgtatcacg aggccctttc gtc           6533

<210> SEQ ID NO 32
<211> LENGTH: 6550
<212> TYPE: DNA
<213> ORGANISM: Artificial Sequence
<220> FEATURE:
<223> OTHER INFORMATION: Synthetic construct: gWiz BS28-LC

<400> SEQUENCE: 32
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtt cggggctggc ttaactatgc ggcatcagag cagattgtac tgagagtgca     180
ccatatgcgg tgtgaaatac cgcacagatg cgtaaggaga aaataccgca tcagattggc     240
tattggccat tgcatacgtt gtatccatat cataatatgt acatttatat tggctcatgt     300
ccaacattac cgccatgttg acattgatta ttgactagtt attaatagta atcaattacg     360
gggtcattag ttcatagccc atatatggag ttccgcgtta caacttacg gtaaatggc      420 ccgcctggct gaccgcccaa cgacccccgc ccattgacgt caataatgac gtatgttccc     480
atagtaacgc caatagggac tttccattga cgtcaatggg tggagtattt acggtaaact     540
gcccacttgg cagtacatca agtgtatcat atgccaagta cgccccctat tgacgtcaat     600
gacggtaaat ggcccgcctg gcattatgcc cagtacatga ccttatggga ctttcctact     660
tggcagtaca tctacgtatt agtcatcgct attaccatgg tgatgcggtt ttggcagtac     720
atcaatgggc gtggatagcg gtttgactca cggggatttc caagtctcca ccccattgac     780
gtcaatggga gtttgttttg gcaccaaaat caacgggact ttccaaaatg tcgtaacaac     840
tccgccccat tgacgcaaat gggcggtagg cgtgtacggt gggaggtcta taagcaga     900 gctcgtttag tgaaccgtca gatcgcctgg agacgccatc cacgctgttt tgacctccat     960
agaagacacc gggaccgatc cagcctccgc ggccgggaac ggtgcattgg aacgcggatt    1020
ccccgtgcca agagtgacgt aagtaccgcc tatagactct ataggcacac ccctttggct    1080
cttatgcatg ctatactgtt tttggcttgg ggcctataca ccccgcttc cttatgctat    1140 aggtgatggt atagcttagc ctataggtgt gggttattga ccattattga ccactcccct    1200
attggtgacg atactttcca ttactaatcc ataacatggc tctttgccac aactatctct    1260
attggctata tgccaatact ctgtccttca gagactgaca cggactctgt atttttacag    1320 gatgggtcc catttattat ttacaaattc acatatacaa caacgccgtc cccgtgccc    1380 gcagttttta ttaaacatag cgtgggatct ccacgcgaat ctcgggtacg tgttccggac    1440
atgggctctt ctccggtagc ggcggagctt ccacatccga ccctggtcc catgcctcca    1500 gcggctcatg gtcgctcggc agctccttgc tcctaacagt ggaggccaga cttaggcaca    1560
```

```
gcacaatgcc caccaccacc agtgtgccgc acaaggccgt ggcggtaggg tatgtgtctg    1620
aaaatgagcg tggagattgg gctcgcacgg ctgacgcaga tggaagactt aaggcagcgg    1680
cagaagaaga tgcaggcagc tgagttgttg tattctgata agagtcagag gtaactcccg    1740
ttgcggtgct gttaacggtg gagggcagtg tagtctgagc agtactcgtt gctgccgcgc    1800
gcgccaccag acataatagc tgacagacta acagactgtt cctttccatg ggtcttttct    1860
gcaggccgcc accatgaggg tccccgctca gctcctgggg ctcctgctgc tctggctccc    1920
aggtgcacac gatgtgacat cctgctgacc cagtctccag tcatcctgtc tgtgagtcca    1980 ggagaaaagag tcagtttctc ctgcagggcc agtcagagta ttggcacaaa catacactgg    2040
tatcagcaaa gaacaaatgg ttctccaagg cttctcataa agtatgcttc tgagtctatc    2100
tctggcatcc cttccaggtt tagtggcagt ggatcaggga cagattttac tcttagcatc    2160
aacagtgtgg agtctgaaga tattgcagat tattactgtc aacaaaataa taactggcca    2220
accacgttcg gtgctgggac caagctggag ctcaaacgta cggtggctgc accatctgtc    2280
ttcatcttcc cgccatctga tgagcagttg aaatctggaa ctgcctctgt tgtgtgcctg    2340
ctgaataact tctatcccag agaggccaaa gtacagtgga aggtggataa cgccctccaa    2400
tcgggtaact cccaggagag tgtcacagag caggacagca aggacagcac ctacagcctc    2460
agcagcaccc tgacgctgag caaagcagac tacgagaaac acaaagtcta cgcctgcgaa    2520
gtcacccatc agggcctgag ctcgcccgtc acaaagagct tcaacagggg agagtgtgga    2580
ggtggcggta gtggcggagg tggttctcag cttcaggagt cgggacctag cctggtgaaa    2640
ccttctcagt ctctgtccct cacctgcact gtcactggct actcaatcac cagtgatttt    2700
gcctggaact ggatccggca gtttccagga aacaagctgg agtggatggg ctacataagt    2760
tatagtggta cactaggta caacccatct ctcaaaagtc gaatctctat cactcgagac    2820
acatccaaga accaattctt cctgcagttg aattctgtga ctattgagga cacagccaca    2880
tattactgtg taacggcggg acgcgggttt ccttattggg gccaagggac tctggtcact    2940
gtctctgcag gaggcggcgg atctggcggt ggaggttctg gcggcggcgg atctgacatc    3000
ctgatgaccc aatctccatc ctccatgtct gtatctctgg gagacacagt cagcatcact    3060
tgccattcaa gtcaggacat taacagtaat ataggtgtgt tgcagcagag accagggaaa    3120
tcatttaagg gcctgatcta tcatggaacc aacttggacg atgaagttcc atcaaggttc    3180
agtggcagtg gatctggagc cgattattct ctcaccatca gcagcctgga atctgaagat    3240
tttgcagact attactgtgt acagtatgct cagtttccgt ggacgttcgg tggaggcacc    3300
aagctggaaa tcaaacgtgg atcagaacaa aagcttatt ctgaagagga cttgtaatag    3360
gtcgacacgt gtgatcagat atcgcggccg ctctagacca ggcgcctgga tccagatcac    3420
ttctggctaa taaagatca gagctctaga gatctgtgtg ttggtttttt gtggatctgc    3480
tgtgccttct agttgccagc catctgttgt ttgcccctcc ccgtgccttc cttgaccct     3540 ggaaggtgcc actcccactg tcctttccta ataaaatgag gaaattgcat cgcattgtct    3600
gagtaggtgt cattctattc tggggggtgg ggtggggcag cacagcaagg gggaggattg    3660
ggaagacaat agcaggcatg ctggggatgc ggtgggctct atgggtacct ctctctctct    3720
ctctctctct ctctctctct ctctctctcg gtacctctct ctctctctct ctctctctct    3780
ctctctctct ctctcggtac caggtgctga agaattgacc cggttcctcc tgggccagaa    3840
agaagcaggc acatcccctt ctctgtgaca caccctgtcc acgcccctgg ttcttagttc    3900
```

```
cagccccact cataggacac tcatagctca ggagggctcc gccttcaatc ccacccgcta    3960
aagtacttgg agcggtctct ccctccctca tcagcccacc aaaccaaacc tagcctccaa    4020
gagtgggaag aaattaaagc aagataggct attaagtgca gagggagaga aaatgcctcc    4080
aacatgtgag gaagtaatga gagaaatcat agaatttctt ccgcttcctc gctcactgac    4140
tcgctgcgct cggtcgttcg gctgcggcga gcggtatcag ctcactcaaa ggcggtaata    4200
cggttatcca cagaatcagg ggataacgca ggaaagaaca tgtgagcaaa aggccagcaa    4260
aaggccagga accgtaaaaa ggccgcgttg ctggcgtttt tccataggct ccgcccccct    4320
gacgagcatc acaaaaatcg acgctcaagt cagaggtggc gaaacccgac aggactataa    4380
agataccagg cgtttccccc tggaagctcc ctcgtgcgct ctcctgttcc gaccctgccg    4440
cttaccggat acctgtccgc ctttctccct tcgggaagcg tggcgctttc tcaatgctca    4500
cgctgtaggt atctcagttc ggtgtaggtc gttcgctcca agctgggctg tgtgcacgaa    4560
ccccccgttc agcccgaccg ctgcgcctta tccggtaact atcgtcttga gtccaacccg    4620
gtaagacacg acttatcgcc actggcagca gccactggta acaggattag cagagcgagg    4680
tatgtaggcg gtgctacaga gttcttgaag tggtggccta actacggcta cactagaagg    4740
acagtatttg gtatctgcgc tctgctgaag ccagttacct tcggaaaaag agttggtagc    4800
tcttgatccg gcaaacaaac caccgctggt agcggtggtt ttttttgtttg caagcagcag    4860 attacgcgca gaaaaaaagg atctcaagaa gatcctttga tcttttctac ggggtctgac    4920
gctcagtgga acgaaaactc acgttaaggg attttggtca tgagattatc aaaaaggatc    4980
ttcacctaga tccttttaaa ttaaaaatga agttttaaat caatctaaag tatatatgag    5040
taaacttggt ctgacagtta ccaatgctta atcagtgagg cacctatctc agcgatctgt    5100
ctatttcgtt catccatagt tgcctgactc cggggggggg gggcgctgag gtctgcctcg    5160
tgaagaaggt gttgctgact cataccaggc ctgaatcgcc ccatcatcca gccagaaagt    5220
gagggagcca cggttgatga gagctttgtt gtaggtggac cagttggtga ttttgaactt    5280
ttgctttgcc acggaacggt ctgcgttgtc gggaagatgc gtgatctgat ccttcaactc    5340
agcaaaagtt cgatttattc aacaaagccg ccgtcccgtc aagtcagcgt aatgctctgc    5400
cagtgttaca accaattaac caattctgat tagaaaaact catcgagcat caaatgaaac    5460 tgcaattat tcatatcagg attatcaata ccatattttt gaaaaagccg tttctgtaat    5520
gaaggagaaa actcaccgag gcagttccat aggatggcaa gatcctggta tcggtctgcg    5580
attccgactc gtccaacatc aatacaacct attaatttcc cctcgtcaaa ataaggtta    5640 tcaagtgaga atcaccatg agtgacgact gaatccggtg agaatggcaa aagcttatgc    5700
atttctttcc agacttgttc aacaggccag ccattacgct cgtcatcaaa atcactcgca    5760
tcaaccaaac cgttattcat tcgtgattgc gcctgagcga gacgaaatac gcgatcgctg    5820
ttaaaaggac aattacaaac aggaatcgaa tgcaaccggc gcaggaacac tgccagcgca    5880
tcaacaatat tttcacctga atcaggatat tcttctaata cctggaatgc tgttttcccg    5940
gggatcgcag tggtgagtaa ccatgcatca tcaggagtac ggataaaatg cttgatggtc    6000
ggaagaggca taaattccgt cagccagttt agtctgacca tctcatctgt aacatcattg    6060
gcaacgctac ctttgccatg tttcagaaac aactctggcg catcgggctt cccatacaat    6120
cgatagattg tcgcacctga ttgcccgaca ttatcgcgag cccatttata cccatataaa    6180
tcagcatcca tgttggaatt taatcgcggc ctcgagcaag acgtttcccg ttgaatatgg    6240
ctcataacac cccttgtatt actgtttatg taagcagaca gttttattgt tcatgatgat    6300
```

```
atatttttat cttgtgcaat gtaacatcag agattttgag acacaacgtg gctttccccc    6360
cccccccatt attgaagcat ttatcagggt tattgtctca tgagcggata catatttgaa    6420
tgtatttaga aaataaaca aataggggtt ccgcgcacat ttccccgaaa agtgccacct     6480
gacgtctaag aaaccattat tatcatgaca ttaacctata aaaataggcg tatcacgagg    6540
ccctttcgtc                                                          6550
```

ANTIBODY-BASED CONSTRUCTS DIRECTED AGAINST TYROSINE KINASE RECEPTORS

CROSS-REFERENCE TO RELATED APPLICATIONS

This application claims the benefit of the filing date of U.S. application Ser. No. 61/375,765, which was filed Aug. 20, 2010. For the purpose of any U.S. application that may claim the benefit of U.S. Application No. 61/375,765, the contents of that earlier filed application are hereby incorporated by reference in their entirety.

GOVERNMENT RIGHTS STATEMENT

This invention was made with Government support under Grant No. R01 CA096504 awarded by the National Institutes of Health. The Government has certain rights in the invention.

TECHNICAL FIELD

This invention relates to antibody-based constructs and, more particularly, to constructs that include, for example, at least one tetrameric immunoglobulin and at least one single chain antibody (scFv). The antibodies can specifically bind a receptor tyrosine kinase, such as an EGF receptor (EGFR), and thereby affect cellular physiology (e.g., receptor clustering, cellular proliferation, differentiation, and/or migration). The compositions described herein have various diagnostic and therapeutic uses, particularly with respect to cancer.

BACKGROUND

Epidermal growth factor receptor (EGFR, also ErbB1) is a single-pass transmembrane receptor tyrosine kinase (RTK) whose signaling is essential for key physiological processes, including cellular growth, migration, adhesion, and apoptosis (Yarden, Nat, Rev. Mol. Cell. Biol., 2:127-137, 2001). As is true for most RTKs, the activation of EGFR is tightly regulated by the availability of ligand, often epidermal growth factor (EGF) or transforming growth factor-α (TGF-α). Consequently, the dysregulation of EGFR expression and signaling has been implicated in numerous forms of cancer and is correlated with poor clinical outcome. Over the last 25 years, a great deal of research has been focused on targeting EGFR and attenuating its activity. One class of targeted therapeutics against EGFR is that of monoclonal antibodies (mAbs), which specifically recognize EGFR and obstruct its activation. The first antibody-based EGFR therapeutic to be clinically approved was cetuximab, the chimeric human immunoglobulin G1 (IgG1) form of the murine mAb 225 (Martinelli et al., Clin. Exp. Immunol., 158:1-9, 2009). With a 100-fold greater affinity for EGFR than the native EGF ligand, mAb 225 directly competes with ligand binding to domain III, blocking dimerization and, consequently, receptor activation (Grunwald et al., J. Natl. Cancer Inst., 95:851-867, 2003; Le et al., Cancer Cell, 7:301-311, 2005). Cetuximab (Erbitux®) can also exert effects via alternative mechanisms, including antibody-dependent cellular cytotoxicity (de Bono et al., Br. Med. Bull., 64:227-254, 2002), induction of receptor internalization and degradation (Ennis et al., Cancer Invest., 9:553-562, 1991), induction of G1-phase cell-cycle arrest, enhanced apoptosis (Prewett et al., Clin. Cancer Res., 8:994-1003, 2002; Ciardiello et al., Clin. Cancer Res., 5:909-916, 1999), and inhibition of vascular endothelial growth factor (VEGF), although these effects vary between cell lines. Other monoclonal antibodies targeting the EGFR ligand-binding domain include the FDA-approved panitumumab and several compounds undergoing clinical trials, including matuzumab and hR-3 (Mateo et al., Immunotechnology, 3:71-81, 1997; Sebastian et al., Biochim. Biophys, Acta, 1766:120-139, 2006).

Unfortunately, the approved mAbs have not lived up to their promise in the clinic. The monotherapy objective response rates of cetuximab and panitumumab are just 11% and 8%, respectively, in the treatment of metastatic colorectal cancer (Cunningham et al., N Engl. J. Med., 351:337-345, 2004; Cohenuram, Anticancer Drugs, 18:7-15, 2007; Van Cutsem, et al., J. Clin. Oncol., 25:1658-1664, 2007). These response rates approximately double when the drugs are used in combination with chemotherapeutics, but there is still much opportunity for the improvement of EGFR-targeted antibody therapeutics. The tepid clinical response of cetuximab and panitumumab can be attributed to delivery limitations, acquired resistance, and receptor mutation (Martinelli, Clin. Exp. Immunol., 158:1-9, 2009). Specifically, antibody penetration into solid tumors is limited by transport and catabolism. Also, tumors may develop resistance to mAbs, often through genetic mutation of EGFR. Heterozygous somatic mutations including deletions, insertions, and point mutations have been observed in the EGFR kinase domain in some lung cancer patients (Lynch et al., N. Engl. J. Med., 350:2129-2139, 2004; Paez et al., Science, 304:1497-1500, 2004; Pao et al., Proc. Natl. Acad. Sci. USA, 101:13306-13311, 2004). These mutations strengthen receptor interactions with ATP, amplifying autophosphorylation and boosting cell survival (Tracy et al., Cancer Res., 64:7241-7244, 2004; Sordella et al., Science, 305:1163-1167, 2004). Furthermore, rearrangements within the ErbB1 gene such as large deletions, point mutants, and insertions are also common, particularly in gliomas (Ekstrand et al., Proc. Natl. Acad. Sci. USA, 89:4309-4313, 1992). As many as 20% of glioblastomas express EGFR variants (Ekstrand et al., Cancer Res., 51:2164-2172, 1991; Liu et al., J Mol. Med., 83:917-926, 2005), the most common of which is EGFRvIII, a constituitively active truncation mutant that removes all of domain I and the majority of domain II of the EGFR extracellular domain to lock the receptor in the active conformation (Wong et al., Proc. Natl. Acad. Sci. USA, 89:2965-2969, 1992). Tumors may also exhibit antibody resistance through abnormal expression of the ligand, for instance through autocrine production or through increased spatial accessibility as a result of aberrant colocalization of the receptor and ligand (Tateishi et al., Cancer Res, 50:7077-7080, 1990; Hirai et at, Dis. Esophagus, 11:221-225, 1998). Due to their reliance on ligand competition for efficacy, the current clinically approved antibodies targeting EGFR are ineffective against mutants such as EGFRvIII and tumor cells that dysregulate EGFR ligands. Consequently, there is a dire need for effective EGFR-targeted mAbs that operate through complementary mechanisms to inhibit receptor signaling.

SUMMARY OF THE INVENTION

The present invention is based, in part, on our discovery of bispecific antibodies that include a tetrameric immunoglobulin and a single chain antibody (scFv). The tetrameric immunoglobuin can specifically bind a first epitope on a molecular target, such as a tyrosine kinase receptor, and the scFv can specifically bind a second epitope, which may be different from the first (e.g., a non-overlapping epitope), on the tyrosine kinase receptor. Because of the nature of the component parts of the present constructs (e.g., tetrameric immunoglobulins and scFvs), we may refer to the compositions of the invention generally as "antibody-based constructs" or "immunoglobulin-based constructs."

We tend to illustrate the invention with constructs including tetrameric immunoglobulins and single chain antibodies, but the constructs can also include other immunoglobulin-based moieties that specifically bind a molecular target. Thus, the invention features antibody-based constructs that include a combination of two or more of a tetrameric antibody, a single chain antibody, a diabody, a triabody, or biologically active variants thereof. For the sake of added clarity, the compositions of the present invention are not conventional monoclonal antibodies, standard diabodies, or standard triabodies, but may include such moieties.

The tetrameric immunoglobulin included in the present constructs can be an IgG of any subtype (e.g., an IgG1, IgG2, IgG3, or IgG4) and can be a chimeric, mammalian (e.g., human or murine) or humanized immunoglobulin. The variable domains of the heavy and light chains in the scFvs or other immunoglobulin-based moieties (e.g., the diabody or triabody) can also be those of a chimeric, mammalian (e.g., human or murine) or humanized immunoglobulin. More specifically, the tetrameric immunoglobulin can be cetuximab, panitumumab, trastuzumab, matuzumab (formerly EMD7000), h-R3 (TheraCIM® hR3; *J Clin. Oncol., May* 2004) or the monoclonal antibody 806. These and other tetrameric antibodies that specifically bind a molecular target as described herein can be incorporated essentially in their entirety. Similarly, the heavy and light chains of the scFvs, diabodies, and triabodies can be the heavy and light chains of these commercially developed antibodies or of any antibody that specifically binds a molecular target as described herein.

In other embodiments, one or more of the component parts of the present constructs (e.g., a tetrameric antibody, scFv, diabody, and/or triabody) can be a biologically active fragment or other variant of a commercially developed antibody or any antibody that specifically binds a molecular target as described herein (e.g., an EGFR). For example, the present constructs can include a tetrameric antibody that constitutes a significant fragment or other variant (e.g., a substitution mutant) of a tetrameric, anti-EGFR antibody. Biologically active fragments and variants of an antibody are those having the ability to specifically bind the molecular target bound by the corresponding unmodified antibody. The affinity or precise binding kinetics may or may not be identical to that of the corresponding unmodified antibody and, in some instances, the affinity of the fragment or other variant may be better than that of the corresponding unmodified antibody.

In other embodiments, one or more of the component parts of the present constructs (e.g., a tetrameric antibody, scFv, diabody, and/or triabody) can include one or more of the CDRs, framework regions, or paratopes of a commercially developed antibody or any antibody that specifically binds a molecular target as described herein. The other regions of the construct can vary so long as it retains the ability to bind the desired molecular target. For example, the present compositions can include a tetrameric antibody having (a) one or more (e.g., 1-6) of the CDRs of a tetrameric antibody that binds a receptor tyrosine kinase (e.g., EGFR); (b) one or more of the CDRs and the surrounding framework regions of such an antibody; or (c) the variable domains of the heavy and/or light chains of such an antibody. Thus, the compositions of the present invention encompass antibody-based constructs that have the same CDRs or the same paratopes as contained in cetuximab, panitumumab, trastuzumab, matuzumab, h-R3, or mAb 806.

In other embodiments, one or more of the component parts of the present constructs (e.g., a tetrameric antibody, scFv, diabody, and/or triabody) can bind the same epitope as a commercially developed antibody or any antibody that specifically binds a molecular target as described herein. For example, the compositions of the present invention encompass antibody-based constructs that bind to the same epitopes as cetuximab, panitumumab, trastuzumab, matuzumab, h-R3, or mAb 806. More generally, the antibody-based construct can bind one epitope that is present in one form of a receptor target and a second epitope that is present in another form of the same receptor (e.g., a truncated or otherwise mutant form of the receptor). For example, the tetrameric immunoglobulin can specifically bind an epitope of a full-length, wild-type EGFR, and the scFv, diabody, or triabody can specifically bind an epitope of a mutant (e.g., a truncation mutant) of the EGFR (e.g., EGFRvIII). The same is true for other receptor tyrosine kinases; the epitopes can differ by virtue of being present in a wild-type form of the molecular target and absent in a mutant form. Alternatively, the tetrameric immunoglobulin can specifically bind an epitope present in the truncation mutant (or other type mutant) and the scFv can specifically bind an epitope of the full-length, wild-type molecular target (e.g., an EGFR). The tetrameric immunoglobulin and/or the scFv, diabody, or triabody can include a variable domain that recognizes and specifically binds a cryptic epitope on the target receptor that is not exposed under native folding conditions.

We may describe the epitope as an "alternative" epitope when it is exposed only in some circumstances (e.g., only in the case of a mutant or activated receptor). For example, an antibody-based construct (e.g., a bi- or trispecific antibody) can bind to a cysteine loop at the end of the EGFR extracellular domain II, including to a conformational epitope that is exposed only when the receptor transitions into the open conformation upon dimerization.

As noted above, the present constructs can include a component part (e.g., a tetrameric immunoglobulin) that differs in its sequence from that of a commercially developed antibody (e.g., cetuximab) but retains the ability to specifically bind the same molecular target as the commercially developed antibody. The variability between any two sequences can be expressed as the percentage of one sequence that is identical to the other. For example, the amino acid sequence of a tetrameric immunoglobulin (or a heavy or light chain thereof) that is present within an antibody-based construct of the invention may be at least or about 70%, 80%, 85%, 90%, 95%, or 98% identical to that of a previously developed immunoglobulin against a receptor tyrosine kinase (or a heavy or light chain thereof). Thus, fragments or other variants of currently available antibodies, including those listed above, can be incorporated into the antibody-based constructs of the present invention and are useful in the present methods so long as they retain biological activity (e.g., sufficient and selective binding to the molecular target). Where a tetrameric immunoglobulin differs from a previously developed immunoglobulin, the differences may lie outside the CDRs and framework regions; in other words, the CDRs and framework regions in the variant immunoglobulin may be identical to those in the previously developed immunoglobulin or highly similar (e.g., at least 95%, 96%, 97%, or 98% identical).

With respect to the configuration, the antibody-based constructs of the invention can be arranged such that an scFv, diabody, or triabody is fused, directly or indirectly (e.g., via a linker), to one or both of the heavy chains of the tetrameric immunoglobulin. For example, an scFv, diabody, triabody, or any combination of such immunoglobulin-like moieties can be fused to the amino termini and/or the carboxy termini of the heavy chain(s) of the tetrameric immunoglobulin. Alternatively, or in addition, the scFv, diabody, or triabody can be fused to the amino termini and/or the carboxy termini of the light chain(s) of the tetrameric immunoglobulin. For example, in one embodiment, the antibody-based constructs comprise a tetrameric immunoglobulin, scFvs fused to the amino termini of the heavy chains, and scFvs fused to the carboxy termini of the light chains. One, two, three, or four of these scFvs can be, instead, a diabody or triabody. At any position where an scFv can be included, one or more diabodies, triabodies, or other immunoglobulin-based binding moieties can be included. In other embodiments, the antibody-based constructs include a plurality of just one type of the immunoglobuin-based binding moieties. For example, the antibody-based constructs can include two, three, four, or more tetrameric immunoglobulins fused to one another (with the proviso that the antibody-based construct is not a naturally occurring immunoglobulin, such as an immunoglobulin of the M class). Similarly, two, three, four or more diabodies or triabodies can be joined to one another (e.g., via linkers).

In addition to the sequences described above that participate in receptor binding, the antibody-based constructs of the invention can further include one or more accessory proteins. The accessory proteins include an amino acid sequence that: prolongs the circulating half-life of the construct; facilitates isolation or purification of the construct; serves as a linker between one part of the construct and another or between the construct and another moiety (e.g., a therapeutic compound or imaging agent); is detectable and thereby serves as a label, marker, or tag; or is a cell disruption agent such as a toxin or a nucleic acid that mediates RNAi (e.g., an siRNA or shRNA. By forming pools of clustered EGFR in the cytoplasm, tagged constructs can generate high local concentrations of toxic agents that selectively destroy transformed cells. Furthermore, by conjugating the antibody-based constructs to fusogenic peptides, one could achieve high concentrations of receptors within endosomes, which could facilitate disruption of the endosomal membrane and allow for diffusion of the toxic compound into the cytosol, enhancing therapeutic efficacy.

The molecular target can be a tyrosine kinase receptor, including a receptor in the ErbB, insulin, PDGF, FGF, VEGF, HGF, Trk, Eph, AXL, LTK, TIE, ROR, DDR, RET, KLG, RYK, or MuSK receptor family. For example, the receptor can be one in the ErbB family, such as an EGFR (also known as ErbB1) or HER2/neu (also known as ErbB2). The FGF receptor can be FGFR2, FGFR3, or FGFR4.

With respect to binding of the EGFR, the tetrameric immunoglobulin, the scFv or an antibody-based construct of which they are a part can compete with ligand binding to domain III, inhibit dimerization and, consequently, receptor activation. The same is true of antibody-based constructs that include a diabody or triabody (e.g., constructs including a tetrameric antibody and one or more diabodies or triabodies). While the compositions of the invention are not limited to those that achieve their utility by any particular mechanism, we further note that the tetrameric immunoglobulin, the scFv, the diabody portion, the triabody portion, or the construct as a whole can be one that achieves one or more of the following outcomes: antibody-dependent cellular cytotoxicity, induction of receptor internalization and degradation, induction of G1-phase cell-cycle arrest, enhanced apoptosis, and modulation of receptor trafficking patterns, thus altering the steady state level of a tyrosine kinase receptor (e.g., an EGFR) available for signal activation. The targeted receptor may be downregulated without activating downstream signaling pathways.

Also within the scope of the invention are nucleic acid molecules that include a nucleic acid sequence encoding an antibody-based construct as described herein or a portion thereof (e.g., an scFv or a heavy or light chain of a tetrameric immunoglobulin). These nucleic acids can be incorporated into expression vectors known in the art using routine molecular biology techniques. For example, a sequence identified in FIGS. 10-13 (in whole or a demarcated part) can be incorporated into a plasmid, a cosmid, a viral vector, or other vector known in the art. The vectors can also include nucleic acid sequences that exhibit a certain degree of identity to those set out in FIGS. 10-13 (in whole or in a demarcated part). For example, vectors within the scope of the present invention can include nucleic acid sequences that are at least or about 70%, 80%, 85%, 90%, 95%, or 98% identical to one or more of the sequences shown in FIGS. 10-13. The sequences can encode immunoglobulin sequences that selectively bind a molecular target as described herein.

The vectors can, in turn, be incorporated into a cell ex vivo, in which proteins useful in bispecific antibodies and other antibody-based constructs will be expressed and from which the proteins can be purified and assembled (as necessary). Such cells are within the scope of the present invention. In addition to ex vivo uses, the nucleic acids and vectors including them can be administered to patients in which they will be expressed.

The antibody-based constructs can be formulated as pharmaceutically acceptable compositions and used in therapeutic and diagnostic methods. Accordingly, the invention features methods of treating a patient who has cancer by administering to the patient a therapeutically effective amount of a pharmaceutically acceptable composition comprising an antibody-based construct as described herein. The antibody will be one that specifically binds at least one epitope on a receptor tyrosine kinase whose expression or activity is associated with the cancer. For example, the antibody can specifically bind an EGFR, including a truncated or other mutant form, or HER2/neu, and the cancer can be breast cancer, bladder cancer, non-small-cell lung cancer, colorectal cancer, squamous-cell carcinoma of the head and neck, ovarian cancer, cervical cancer, lung cancer, esophageal cancer, salivary gland cancer, a glioblastoma, or pancreatic cancer. Any of the therapeutic methods can include a step of identifying a patient in need of treatment. For example, one can use the antibodies described herein or others that recognize the desired target to identify aberrant receptor expression in a biopsy sample. Alternatively or in addition, any of the therapeutic methods can include a step in which the patient is also treated with a conventional therapeutic agent (e.g., a conventional small molecule chemotherapeutic agent).

In another aspect, the antibody-based constructs can be used in the treatment of autoimmune disease, including psoriasis. Accordingly, the invention features methods of treating a patient who has an autoimmune disease by administering to the patient a therapeutically effective amount of a pharmaceutically acceptable composition comprising an antibody-based construct as described herein. The antibody will be one that specifically binds at least one epitope on a receptor tyrosine kinase whose expression or activity is associated with the autoimmune disease.

In addition to their promise as therapeutic agents, the present antibody-based constructs can be used to deliver contrast agents or other moieties useful in imaging (e.g., imaging a tumor before, during, or after treatment). Further, with sub-nanomolar affinity for a receptor tyrosine kinase, such as EGFR, the antibodies can selectively and tightly bind the receptor, providing accurate detection for tumor diagnosis applications.

The modular format of the constructs we have developed is advantageous because it allows for the insertion of any immunoglobulin-like moieties (e.g., antibody variable domains) with engineered specificity for multiple non-overlapping sites on the antigen of interest. This provides a generalized scaffold for eliciting clustering of receptor tyrosine kinases, including those in the ErbB family and any other whose overexpression or aberrant expression is associated with cancer, autoimmunity or another disease condition (e.g., polycystic kidney disease). The size of immunoglobulins (e.g., an IgG backbone) allows for superior retention in the bloodstream and FcRn recycling, and we expect the molecular specificity of the variable domains to minimize off-target toxicity.

In summary, various aspects of the invention include the antibody-based constructs described herein, compositions containing them (e.g., pharmaceutically acceptable preparations, stock solutions, kits, and the like), nucleic acids encoding them, and cells in which they are expressed (e.g., cells in tissue culture). Methods of making and methods of isolating or purifying the antibodies are also within the scope of the present invention. For example, a vector described herein can be used to express an immunoglobulin as described herein in a biological cell using routine methods known in the art of protein production. The resulting protein can then be readily isolated, perhaps with the assistance of an encoded tag. We may refer to an antibody-based construct (or a portion thereof) as "isolated" or "purified" when it has been substantially separated from materials with which it was previously associated. For example, an antibody-based construct (or a portion thereof) can be isolated or purified following chemical synthesis or expression in cell culture as described above. Methods of using the antibody-based constructs to assess cells in vitro and to treat patients are also within the scope of the present invention. Production, isolation, formulation, screening, diagnostic and treatment methods are discussed further below.

The method of treatment claims included herein may be expressed in terms of "use." For example, the present invention features the use of the antibody-based constructs described herein in the preparation of a medicament or in the manufacture of a medicament for the treatment of cancer, including the specific cancers described herein.

One of ordinary skill in the art can consult numerous publications concerning the commercially developed antibodies described herein, including U.S. Pat. Nos. 4,943,533, 5,558,864, 6,165,464, 6,217,866, 6,235,883, and 7,767,792 and U.S. Patent Application Publication 2009/0010840. These publications disclose immunoglobulin sequences useful in the present antibody-based constructs, and are hereby incorporated by reference in their entireties.

The details of one or more embodiments of the invention are set forth in the accompanying drawings, the description below, and/or the claims. Other features, objects, and advantages of the invention will be apparent from the drawings, descriptions, and claims.

BRIEF DESCRIPTION OF THE DRAWINGS

Figure 10:
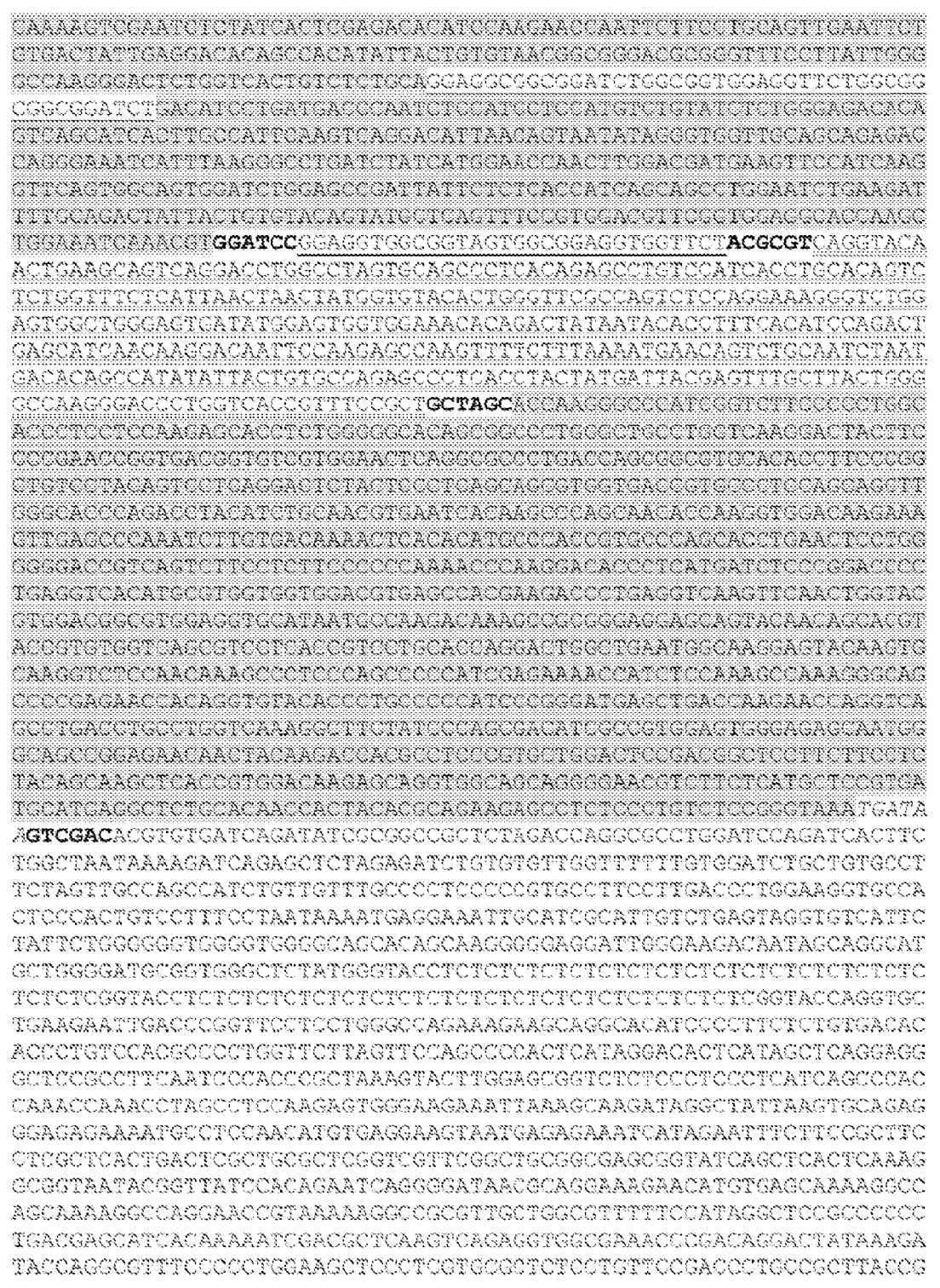

FIG. 10 is a representation of the sequence of gWiz BS28-HN (SEQ ID NO: 29). Vector sequences beginning at TCGCGC . . . and ending with the PstI restriction site CTGCAG are represented by SEQ ID NO:2. The Kozak Sequence GCCGCCACC is represented by SEQ ID NO:3. The leader sequence beginning with ATGGGT . . . and ending with . . . GTTGCT is represented by SEQ ID NO:4. The NdeI restriction site CATATG is represented by SEQ ID NO:5. The NheI restriction site GCTAGC is represented by SEQ ID NO:6. The 806 VH sequence beginning with CAGCTT . . . and ending with . . . TCTGCA is represented by SEQ ID NO:7. The (Gly$_4$Ser)$_3$ (SEQ ID NO: 26) linker sequence beginning with GGAGGC . . . and ending with . . . GGATCT is represented by SEQ ID NO:8. The 806 VL sequence beginning with GACATC . . . and ending with . . . AAACGT is represented by SEQ ID NO:9. The BamHI restriction site GGATCC is represented by SEQ ID NO: 10. The (Gly$_4$Ser)$_2$ (SEQ ID NO: 27) linker sequence beginning with GGAGGT . . . and ending with . . . GGTTCT is represented by SEQ ID NO: 11. The MluI restriction site ACGCGT is represented by SEQ ID NO: 12. The 225 HC sequence beginning with CAGGTA . . . and ending with . . . TCCGCT is represented by SEQ ID NO: 13. The NheI restriction site GCTAGC is represented by SEQ ID NO:6. The CH 1,2,3 sequence beginning with ACCAAG . . . and ending with . . . GGTAAA is represented by SEQ ID NO: 14. The stop sequence TGATAA is represented by SEQ ID NO: 15. The SalI sequence GTCGAC is represented by SEQ ID NO: 16. Vector sequences beginning at ACGTGT . . . and ending with . . . TTCGTC are represented by SEQ ID NO: 17.

Figure 11:
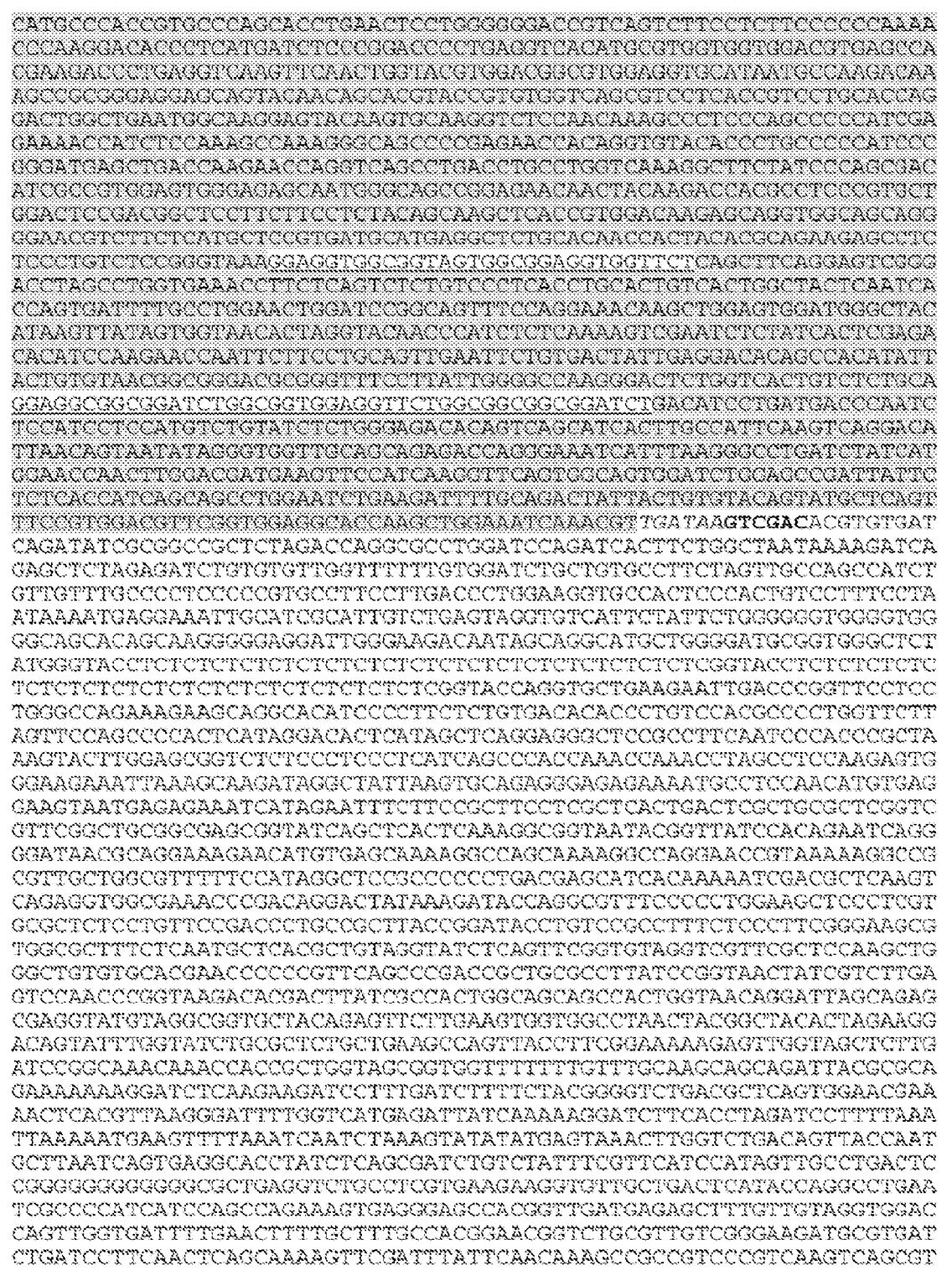

FIG. 11 is a representation of the sequence of gWiz BS28-HC (SEQ ID NO: 30), Vector sequences beginning at TCGCGC . . . and ending with the PstI restriction site CTGCAG are represented by SEQ ID NO:2. The Kozak Sequence GCCGCCACC is represented by SEQ ID NO:3. The leader sequence beginning with ATGGGT . . . and ending with . . . GTTGCT is represented by SEQ ID NO:4. The MluI restriction site ACGCGT is represented by SEQ ID NO: 12. The 225 HC sequence beginning with CAGGTA . . . and ending with . . . TCCGCT is represented by SEQ ID NO: 13. The NheI restriction site GCTAGC is represented by SEQ ID NO: 6. The CH 1,2,3 sequence beginning with ACCAAG . . . and ending with . . . GGTAAA is represented by SEQ ID NO: 14. The (Gly$_4$Ser)$_2$ (SEQ ID NO: 27) linker sequences beginning with GGAGGT . . . and ending with . . . GGTTCT is represented by the SEQ ID NO: 11. The 806 VH sequence beginning with CAGCTT . . . and ending with . . . TCTGCA is represented by SEQ ID NO: 7. The (Gly$_4$Ser)$_3$ (SEQ ID NO: 26) linker sequence beginning with GGAGGC . . . and ending with . . . GGATCT is represented by SEQ ID NO:8. The 806 VL sequence beginning with GACATC . . . and ending with . . . AAACGT is represented by SEQ ID NO:9. The stop sequence TGATAA is represented by SEQ ID NO: 15. The SalI sequence GTCGAC is represented by SEQ ID NO: 16. Vector sequences beginning at ACGTGT . . . and ending with . . . TTCGTC are represented by SEQ ID NO:17.

FIG. 12 is a representation of the sequence of gWiz BS28-LN (SEQ ID NO: 31). Vector sequence beginning at TCGCGC . . . and ending with the PstI restriction site CTGCAG is represented by SEQ ID NO:2. The Kozak Sequence GCCGCCACC is represented by SEQ ID NO:3. The leader sequence beginning with ATGAGG . . . and ending with . . . GGTGCA is represented by SEQ ID NO: 18.

Figure 1:
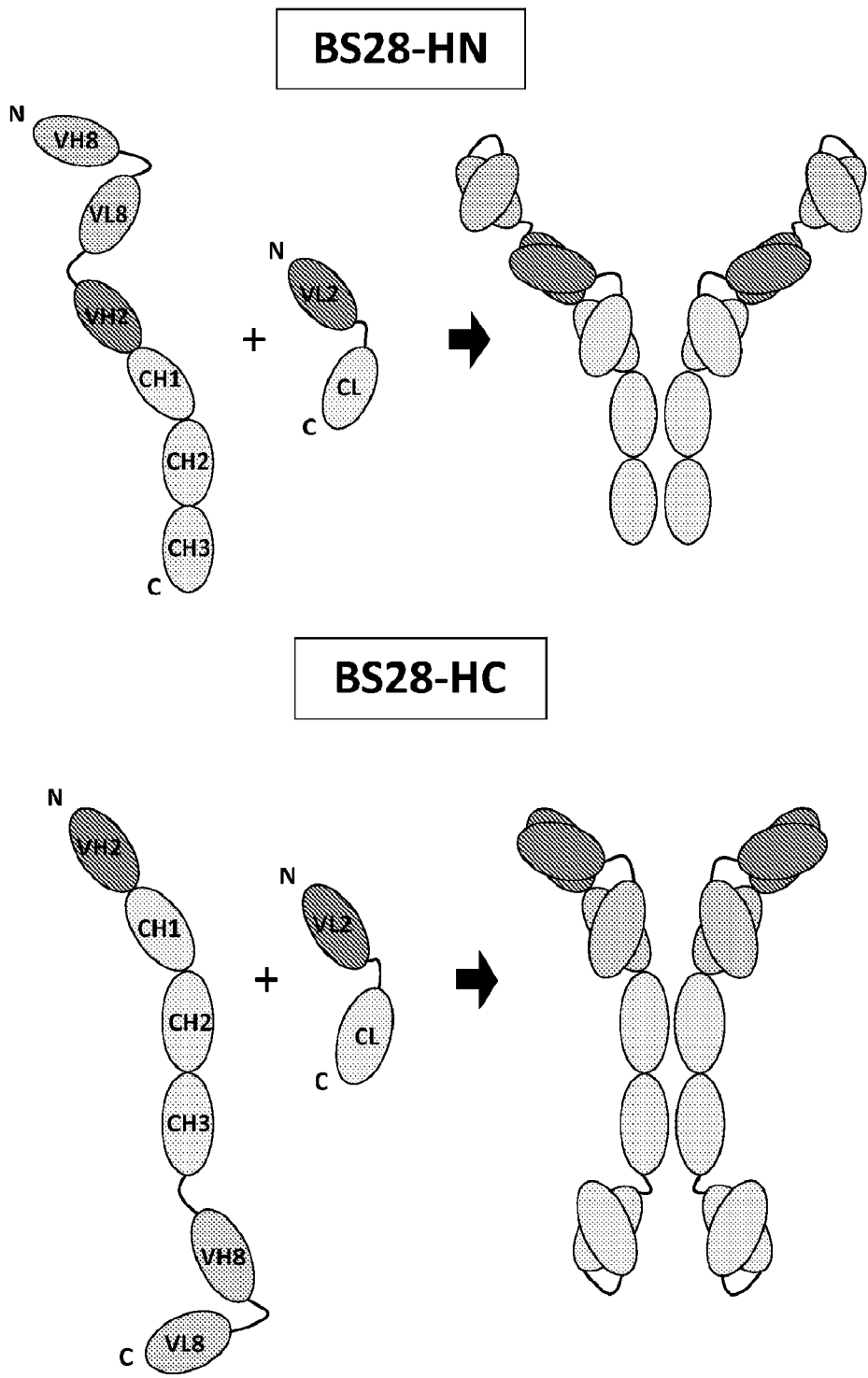
FIG. 1 is a schematic illustrating the structure of bispecific antibodies within the present invention. A human IgG1 isotype backbone is used as a scaffold for engineering BS28 constructs. In accordance with convention, the heavy chain is shown to include three constant domains (CH1, CH2, and CH3) and one variable domain (VH), whereas the light chain has one constant domain (CL) and one variable domain (VL). The amino (N) and carboxy (C) termini of the heavy and light chains are indicated. Antibodies are assembled in vitro in 2:2 complexes of heavy and light chain moieties, linked by three disulfide bonds. The 806 scFv is fused to the heavy or light chain at the N or C terminus with a flexible linker and the fusion constructs are named as indicated. Note that the variable domains are labeled according to the antibody with which they are associated (2=225; 8=806). The full sequences of the four BS28 constructs that were designed are provided in Appendix A.

The NdeI restriction site CATATG is represented by SEQ ID NO:5. The NheI restriction site GCTAGC is represented by SEQ ID NO:6. The 806 VH sequence beginning with CAGCTT . . . and ending with . . . TCTGCA is represented by SEQ ID NO:7. The (Gly$_4$Ser)$_3$ (SEQ ID NO: 26) linker sequence beginning with GGAGGC . . . and ending with . . . GGATCT is represented by SEQ ID NO:8. The 806 VL sequence beginning with GACATC . . . and ending with . . . AAACGT is represented by SEQ ID NO:9. The BamHI restriction site GGATCC is represented by SEQ ID NO: 10. The (Gly$_4$Ser)$_2$ (SEQ ID NO: 27) linker sequence beginning with GGAGGT . . . and ending with . . . GGTTCT is represented by SEQ ID NO: 11. The DraIII restriction site CACGATGT is represented by SEQ ID NO: 19. The 225 LC sequence beginning with GACATC . . . and ending with . . . CTCAAA is represented by SEQ ID NO:20. The BsiWI restriction site CGTACG is represented by SEQ ID NO:21. The Ckappa sequence beginning with GTGGCT . . . and ending with . . . GAGTGT is represented by SEQ ID NO: 22. The stop sequence TAATAG is represented by SEQ ID NO:23. The SalI sequence GTCGAC is represented by SEQ ID NO: 16. Vector sequence beginning at ACGTGT . . . and ending with . . . TTCGTC are represented by SEQ ID NO: 17.

Figure 13:
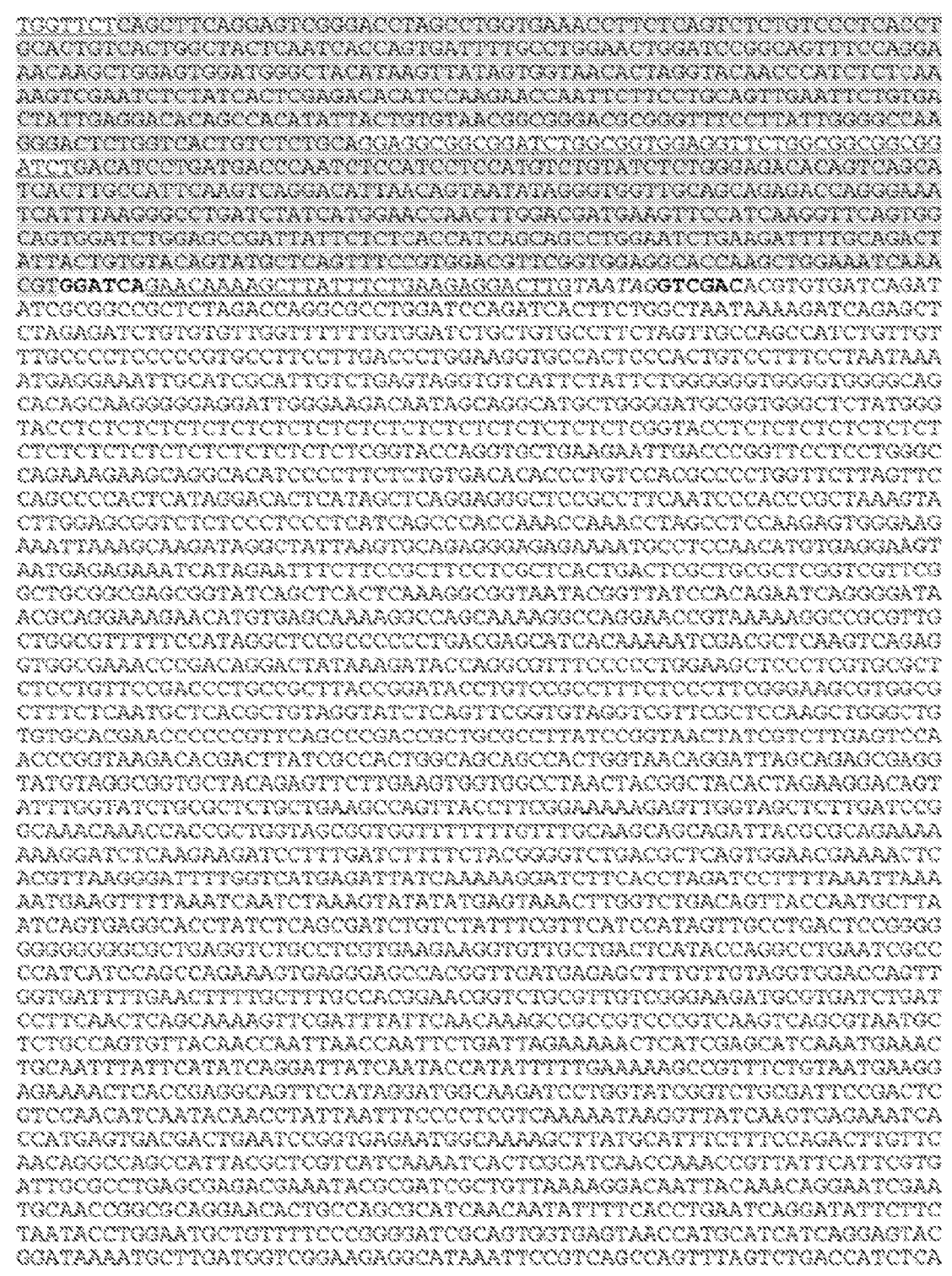

FIG. 13 is a representation of the sequence of gWiz BS28-LC (SEQ ID NO: 32). Vector sequences beginning at TCGCGC . . . and ending with the PstI restriction site CTGCAG are represented by SEQ ID NO:2. The Kozak Sequence GCCGCCACC is represented by SEQ ID NO:3. The leader sequence beginning with ATGAGG . . . and ending with . . . GGTGCA is represented by SEQ ID NO: 18. The DraIII restriction site CACGATGT is represented by SEQ ID NO: 19. The 225 LC sequence beginning with GACATC, and ending with . . . CTCAAA is represented by SEQ ID NO:20. The BsiWI restriction site CGTACG is represented by SEQ ID NO:21. The Ckappa sequence beginning with GTGGCT . . . and ending with . . . GAGTGT is represented by SEQ ID NO:22. The (Gly$_4$Ser)$_2$ (SEQ ID NO: 27) linker sequence beginning with GGAGGT . . . and ending With . . . GGTTCT is represented by SEQ ID NO: 11. The 806 VH sequence beginning with CAGCTT . . . and ending with . . . TCTGCA is represented by SEQ ID NO:7. The (Gly$_4$Ser)$_3$ (SEQ ID NO: 26) linker sequence beginning with GGAGGC . . . and ending with . . . GGATCT is represented by SEQ ID NO:8. The 806 VL sequence beginning with GACATC . . . and ending with . . . AAACGT is represented by SEQ ID NO: 9. The GS spacer restriction site GGATCA is represented by SEQ ID NO: 24. The Cmyc Epitope Tag sequence beginning with GAACAA . . . and ending with . . . GACTTG is represented by SEQ ID NO:25. The stop sequence TAATAG is represented by SEQ ID NO:23. The SalI sequence GTCGAC is represented by SEQ ID NO: 16. Vector sequences beginning at ACGTGT . . . and ending with . . . TTCGTC are represented by SEQ ID NO: 17.

DETAILED DESCRIPTION

In an effort to attain and potentially enhance mAb-induced downregulation and enhance targeting of mutant or activated molecular targets, including tyrosine kinsase receptors, we have created immunoglobulin-based constructs that incorporate multiple variable domains (e.g., one or more (e.g., 2-8 copies) of the variable domains of either or both of the monoclonal antibodies 225 and 806). In addition to promoting crosslinking to complement endogenous mAb effects, the polyspecific (e.g., bi- or trispecific) format could enhance clustering by bringing two or more binding sites (e.g., two EGFR epitopes) into proximity with one another and other receptors, increasing the local concentration of any antibody-based construct(s) bound thereto and augmenting the likelihood of epitope presentation. This enhanced clustering capacity renders polyspecific constructs superior to existing therapeutic compounds or mAbs that are simply combined. Additionally, where a variable region such as that of the mAb 806 is present, it renders the treatment effective on both wild-type and mutant versions of the receptor.

We are using the modular structure and design of antibodies, whether in the form of a naturally produced immunoglobulin or an engineered binder such as an scFv, diabody, or triabody as the basis for a new generation of antibody-based therapeutics against EGFR and other receptor tyrosine kinases. As described further below, the present compositions can also be used as antibody-based diagnostics (e.g., they may be tagged with an imaging agent). While the compositions and methods of the invention are not limited to those that function by any particular mechanism, our studies to date indicate that the compositions described herein operate through a distinct receptor clustering mechanism. Preliminary work has shown significant and reproducible receptor downregulation by compositions over a panel of eleven cell lines expressing both wild-type and mutant EGFR. This in vitro downregulation has also translated into in vivo tumor growth inhibition in an A431 human epidermoid carcinoma mouse xenograft model.

Recently, a monoclonal antibody that specifically targets the truncation mutant EGFRvIII, mAb 806, was developed (Johns et al., *Int. J Cancer,* 98:398-408, 2002; see also U.S. Pat. No. 7,767,792). mAb 806 binds to a cysteine loop at the end of EGFR extracellular domain II, a conformational epitope that is exposed only when the receptor transitions into the open conformation upon dimerization. Since this antibody is not competitive with compounds targeting the ligand-binding domain, it is undergoing clinical testing both as a monotherapy and as a combination therapy with cetuximab or chemotherapeutics. A recent phase I clinical trial of mAb 806 demonstrated specific targeting of the mutant receptor and no significant toxicity.

Antibody-based Constructs: As noted, we may refer to the compositions of the invention that include high molecular weight proteins that specifically bind to molecular targets, as "antibody-based constructs" or "immunoglobulin-based constructs." The binding is "specific" or "selective" when the antibody-based construct or a portion thereof binds an epitope on a molecular target to the substantial exclusion of other molecular targets or other epitopes within the same target. We may refer to the antibody-based constructs described herein as "including" certain sequences. For example, we describe antibody-based constructs including various combinations of a tetrameric immunoglobulin, an scFv, a diabody, and a triabody. Further, an accessory sequence may be included. In all events, however, the antibody-based constructs of the invention can include, consist of, or consist essentially of the recited sequences or component parts.

The antibody-based constructs can differ with respect to the total number of binding sites they include (their valency), the number of different epitopes they bind (their specificity), and the number of different paratopes they include. A conventional monoclonal antibody is bivalent, monospecific, and monoparatopic. All of the constructs of the invention are multivalent. When the present constructs include two binding sites, they are bivalent; when they include four binding sites, they are tetravalent; when they include six binding sites, they are hexavalent; when they include eight binding sites, they are octavalent, and so forth. With respect to the bindable epitope(s), constructs that will bind a single epitope are "monospecific"; those that specifically bind two epitopes are "bispecific"; those that bind three epitopes are "trispecific"; those that bind four epitopes are "tetraspecific"; and so forth. Constructs that include one paratope are "monoparatopic"; constructs having two paratopes are "biparatopic"; constructs having three paratopes are "triparatopic"; and so forth. For example, a construct that consists of a tetrameric antibody that binds epitope "a" and two scFvs that bind epitope "b" is tetravalent, bispecific, and biparatopic. A construct that consists of a tetrameric antibody that binds epitope "a", and four scFvs that bind epitope "b" is hexavalent, bispecific, and biparatopic. A construct that consists of a tetrameric antibody that binds epitope "a", two scFvs that bind epitope "b", and two scFvs that bind epitope "c" is hexavalent, trispecific, and triparatopic. The invention encompasses but is not limited to constructs having these attributes.

Antibody-based constructs commonly include an even number of binding sites, but the constructs of the invention are not so limited; they may be bivalent, trivalent, tetravalent, pentavalent, hexavalent, septavalent, octavalent, nonavalent, or decavalent, or they may have even more binding sites (e.g., 12 binding sites).

Where two or more epitopes are bound, the epitopes may be within the same molecular target (e.g., they may both be located in a wild-type EGFR) or they may be located in different molecular targets (e.g., one may be located in a wild-type EGFR and one may be located in a mutant EGFR).

While the bispecific antibodies can contain naturally occurring amino acid residues (and may consist of only naturally occurring amino acid residues), the invention is not so limited. The constructs can also include non-naturally occurring residues (e.g., selenocysteine or norleucine). Any of the antibody-based constructs may also vary (e.g., from a wild-type protein from which they were derived) due to post-translational modification(s). For example, the glycosylation pattern may vary or there may be differences in amidation or phosphorylation.

It is to be understood that the antibody-based constructs of the present invention are not naturally occurring proteins in their entirety, but may include sequences or component parts that are naturally occurring (e.g., that are naturally produced by biological cells). Accordingly, we may refer to the constructs generally or to a portion thereof (e.g., the scFv, diabody, or triabody) as "genetically modified" to indicate that the protein is non-naturally occurring (e.g., having a configuration that is not found in nature or comprising a mutant of a wild-type sequence).

As noted above, the compositions of the present invention encompass antibody-based constructs that bind to the same epitopes as commercially developed antibodies or the constructs exemplified herein. The compositions of the present invention also encompass antibody-based constructs that have one or more of the same paratopes as a commercially developed antibody, including one or more of the same paratopes of a construct exemplified herein. Residues important in defining various paratopes and epitopes are known in the art, and methods known in the art can be used to make these determinations where the sites are not already defined. For example, in cetuximab, the variable domain interacting residues are W52, D58, Y101, Y102, Y104, and D103 of the heavy chain and Q27, Y50, and W94 of the light chain (see Li et al., *Cancer Cell* 7:301-311, 2005). Accordingly, the constructs of the present invention include those having the same interacting residues as those defined for cetuximab.

Another way the antibody-based constructs of the present invention can be characterized is by their affinity for the molecular target they were designed to specifically bind. For example, an antibody-based construct (or a component part thereof) may bind a molecular target with an affinity in the pM to nM range (e.g., an affinity of less than or about 1 pM, 10 pM, 25 pM, 50 pM, 100 pM, 250 pM, 500 pM, 1 nM, 5 nM, 10 nM, 15 nM, 20 nM, 25 nM, 30 nM, 40 nM or 50 nM).

In addition to these characteristics, any given antibody-based construct can be characterized in terms of its ability to modify cell behavior (e.g., cellular proliferation or migration) or to positively impact a symptom of a disease, disorder, condition, syndrome, or the like, associated with the expression or activity of the molecular target. In vitro assays for assessing binding to a molecular target, cellular proliferation, and cellular migration are known in the art. For example, where the molecular target is an EGFR, binding, proliferation, and migration assays can be carried out using A431 epidermoid carcinoma cells, HeLa cervical carcinoma cells, and/or HT29 colorectal carcinoma cells. Other useful cells and cell lines will be known to those of ordinary skill in the art. For example, an antibody-based construct can be analyzed using U87 glioblastoma cells, hMEC cells (human mammary epithelial cells), or Chinese hamster ovary (CHO) cells. The molecular target can be expressed as a fluorescently tagged protein to facilitate analysis of an engineered protein's effect on the target. For example, the assays of the present invention can be carried out using a cell type as described above transfected with a construct expressing an EGFR-green fluorescent protein fusion. An antibody-based construct may inhibit cellular proliferation or migration by at least or about 30% (e.g., by at least or about 30%, 40%, 50%, 65%, 75%, 85%, 90%, 95% or more) relative to a control (e.g., relative to proliferation or migration in the absence of the antibody or a scrambled engineered protein).

The affinity of an antibody-based construct for its target may be greater than the affinity of either the tetrameric immunoglobulin or the scFv therein. For example, the affinity of an antibody-based construct for its molecular target may be at least or about an order of magnitude greater than the affinity of the tetrameric immunoglobulin alone at either endosomal pH (6.0), physiological pH (7.4), or both.

One can also subject an immunoglobulin, scFv, diabody, or triabody (whether currently known or newly discovered) to directed evolution in order to generate a modified variant with improved specificity and affinity for a given molecular target.

In addition to, or in place of, one or more of the components described above, the antibody-based constructs can include one or more of: (i) an Fab fragment, a monovalent fragment consisting of the VLC, VHC, CL and CH1 domains; (ii) a F(ab')$_2$ fragment, a bivalent fragment comprising two Fab fragments linked by a disulfide bridge at the hinge region; (iii) a Fd fragment consisting of the VHC and CH1 domains; (iv) a Fv fragment consisting of the VLC and VHC domains of a single arm of an antibody, (v) a dAb fragment (Ward et al., *Nature* 341:544-546, 1989), which consists of a VHC domain; and (vi) an isolated complementarity determining region (CDR) having sufficient framework to specifically bind, e.g., an antigen binding portion of a variable region. An antigen-binding portion of a light chain variable region and an antigen binding portion of a heavy chain variable region, e.g., the two domains of the Fv fragment, VLC and VHC, can be joined, using recombinant methods, by a synthetic linker that enables them to be made as a single protein chain in which the VLC and VHC regions pair to form monovalent molecules (known as single chain Fv (scFv); see e.g., Bird et al., *Science* 242:423-426, 1988; and Huston et al., *Proc. Natl. Acad. Sci. USA* 85:5879-5883, 1988). Such single chain antibodies are also intended to be encompassed within the term "antigen-binding portion" of an antibody or as "a variant" of an antibody.

As is recognized in the art, diabodies are bivalent or bispecific molecules generated by dimerization of two VH-VL fragments. Dimerization is driven by a limited length linker joining the VH and the VL domains (e.g., GGGGS) (SEQ ID NO: 28); the linkers are too short to allow intrachain assembly of the VH and VL domains. Thus, two fragments assemble into a dimeric molecule. Further reduction of the linker length to 0-2 amino acids results in the generation of trimeric triabodies or tetrameric tetrabodies. Bispecific diabodies can be formed by expressing two fragments of the structure VHA-VLB and VHB-VLA in the same cells. This leads to formation of heterodimers with two different binding sites. Methods for constructing bispecific diabodies are described in Kontermann et al. "Enzyme immunoassays using bispecific diabodies", *Immunotechnology* 3:137-144, 1997). If necessary, one of ordinary skill in the art could also consult U.S. Pat. No. 7,122,646.

The component part of the present antibody-based constructs can be obtained using conventional techniques known to those of ordinary skill in the art, and the portions can be screened for utility in the same manner as are intact antibodies. For example, an Fab fragment can result from cleavage of a tetrameric antibody with papain; Fab' and F(ab')2 fragments can be generated by cleavage with pepsin.

The present constructs can include sequences or component parts from a single species or more than one species. As noted, one or more of the immunoglobulin sequences within the present constructs can be human or murine. The proteins can also be porcine, ovine, bovine, equine, feline, canine, or of a non-human primate. As noted, the invention encompasses biologically active variants of antibody-based constructs, and these variants can be derived from any mammal, including those listed here.

The various components of the antibody-based constructs can be joined together chemically by conventional techniques, can be expressed and allowed to dimerize, and/or can be prepared as contiguous polypeptides using genetic engineering techniques. For example, nucleic acids encoding a chimeric or humanized chain can be expressed to produce a contiguous polypeptide. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman et al., *BioTechnology*, 10:1455-1460,1992, regarding CDR-graft antibody, and Ladner et al., U.S. Pat. No. 4,946,778 and Bird, R. E. et al., *Science* 242:423-426,1988 regarding single chain antibodies.

An advantage of the present invention is that the antibody-based constructs can include known tetrameric antibodies and/or biologically active variants thereof. The configuration of the present constructs, including those comprising tetrameric immunoglobulins, can vary as described above. For example, any combination of an scFv, diabody, or triabody can be fused or conjugated, directly or indirectly (e.g., via a linker), to one or both of the heavy chains of the tetrameric immunoglobulin, an Fab fragment, or an F(ab')2 fragment. For example, an scFv, diabody, triabody, or any combination of such immunoglobulin-like moieties can be fused to the amino termini of the heavy chain(s) of a tetrameric immunoglobulin, an Fab fragment, or an F(ab')2 fragment. Alternatively, or in addition, the scFv, diabody, or triabody can be fused to the carboxy termini of the light chain(s) of the tetrameric immunoglobulin, Fab fragment, or F(ab')2 fragment. For example, in one embodiment, the antibody-based constructs comprise a tetrameric immunoglobulin, scFvs fused to the amino termini of the heavy chains, and scFvs fused to the carboxy termini of the light chains. One, two, three, or four of these scFvs can be, instead, a diabody or triabody. For example, the antibody-based construct can include a tetrameric immunoglobulin, diabodies fused to the amino termini of the heavy chains, and diabodies fused to the carboxy termini of the light chains. For example, the antibody-based construct can include a tetrameric immunoglobulin, triabodies fused to the amino termini of the heavy chains, and triabodies fused to the carboxy termini of the light chains. Instead of a tetrameric immunoglobulin, the present constructs can include a diabody or triabody as the "backbone" of the construct, to which two or more scFvs can be been linked. As noted, while different types of immunoglobulin-like moieties can be used, the present constructs can also include a plurality of just one type of immunoglobuin-based moiety. For example, the antibody-based constructs can include two, three, four, or more tetrameric immunoglobulins fused to one another (or conjugated) (with the provisio that the antibody-based construct is not a naturally occurring immunoglobulin, such as an immunoglobulin of the M class). Similarly, two, three, four or more diabodies or triabodies can be joined to one another (e.g., via linkers) or conjugated.

As noted, immunoglobulin sequences incorporated into the present compositions include those of the G class of immunoglobulins, and all subtypes, including IgG1, IgG2, IgG3, and IgG4, can be used. The compositions of the invention can also include immunoglobulin sequences constituting an IgM, IgA, IgD, or IgE or a subtype thereof (e.g., IgA1 or IgA2). Fragments of these immunoglobulins or other variants thereof that are biologically active in the context of the present compositions can also be used.

The accessory sequence can be one that prolongs the circulating half-life of the antibody-based construct, a polypeptide that facilitates isolation or purification of the engineered protein, an amino acid sequence that facilitates the bond (e.g., fusion or conjugation) between one part of the antibody-based construct and another or between the antibody-based construct and another moiety (e.g., a therapeutic compound), an amino acid sequence that serves as a label, marker, or tag (including imaging agents), or an amino acid sequence that is toxic.

The amino acid sequence that increases the circulating half-life can be an Fc region of an immunoglobulin, including an immunoglobulin that has a reduced binding affinity for an Fc receptor (such as those described in U.S. Patent Application No. 20090088561, the content of which is hereby incorporated by reference in its entirety). As the antibody-based constructs of the present invention can include tetrameric immunoglobulins, and as the Fc regions of tetrameric immunoglobulins can increase circulating half-life, where the constructs include a tetrameric immunoglobulin, the Fc region of the immunoglobulin can also serve to increase the construct's circulating half-life; the accessory sequence can be a part of the heterologous amino acid sequence.

Half-life can also be increased by the inclusion of an albumin (or a portion or other variant thereof that is large enough to have a desired effect on half-life). The albumin can be a serum albumin, such as a human or bovine serum albumin.

The antibody-based constructs or a portion thereof can also be "pegylated" using standard procedures with poly (ethylene glycol). Constructs that are pegylated may have an improved circulating half-life.

Where the antibody-based constructs include an accessory protein that facilitates isolation or purification, that protein can be a tag sequence designed to facilitate subsequent manipulations of the expressed nucleic acid sequence (e.g., purification or localization). Tag sequences, such as green fluorescent protein (GFP), glutathione S-transferase (GST), c-myc, hemagglutinin, β galactosidase, or Flag™ tag (Kodak) sequences are typically expressed as a fusion with the polypeptide encoded by the nucleic acid sequence. Such tags can be inserted in a nucleic acid sequence such that they are expressed anywhere along an encoded polypeptide including, for example, at either the carboxyl or amino termini. The type and combination of regulatory and tag sequences can vary with each particular host, cloning or expression system, and desired outcome.

As noted, the antibody-based constructs can include linkers at various positions (e.g., between the tetrameric immunoglobulin and an scFv). As is recognized in the art, the linker typically included between the immunoglobulin chains in an scFv (typically about 15 amino acids long) is longer than the linker used to configure diabodies or triabodies (which is typically about 5 amino acids long). The linker can be an amino acid sequence that is joined by standard peptide bonds to the engineered protein. The length of the linker can vary including an essentially absent linker in which the proteins are directly fused and, where it is an amino acid sequence, can be at least three and up to about 300 amino acids long (e.g., about 4, 8, 12, 15, 20, 25, 50, 75, 80, 85, 90, 95, 100, 125, 150, 175, 200, 250 or 300 amino acids long). Moreover, a non-peptide linker such as polyethylene glycol or an alternative polymer could be used. As with all other domains in the antibody-based constructs, the amino acid residues of the linker may be naturally occurring or non-naturally occurring. We have used a polypeptide linker having the sequence GSGGGSGGGKGGGGT (SEQ ID NO:1), and linkers comprising this sequence or functional variants thereof can be used to join tetrameric antibodies to scFvs or another immunoglobulin-like moiety. The linkers can be glycine-rich (e.g., more than 50% of the residues in the linker can be glycine residues).

The amino acid sequence that serves as a label, marker, or tag can be essentially any detectable protein. It may be detectable by virtue of an intrinsic property, such as fluorescence, or because it mediates an enzymatic reaction that gives rise to a detectable product. The detectable protein may be one that is recognized by an antibody or other binding protein.

The antibody-based constructs can also be configured to carry imaging or contrast agents, many of which are known in the art and can be connected to a construct using standard techniques.

Once identified, whether through phage display, mRNA display, yeast surface display, or by any other mechanism, a protein can be incorporated into the antibody-based constructs described herein using standard recombinant techniques. These techniques are well known in the art.

Molecular Targets: A wide variety of molecular targets can be specifically bound and these include molecules expressed on the cell surface, such as receptors for growth factors, neurotransmitters, and the like. The receptor can be a tyrosine kinase receptor, and much of the work with the constructs described in the Examples has focused on the epidermal growth factor (EGF) receptor (EGFR). This receptor is a receptor tyrosine kinase in the ErbB family that comprises three regions: an extracellular region, a transmembrane domain, and an intracellular region that includes a juxtamembrane domain, kinase domain, and a C-terminal tail containing phosphorylation sites. These domains and sites are understood in the art. The extracellular region consists of four domains of which domains I and III are leucine rich repeat folds and domains II and IV are cysteine-rich domains. The receptor is predominantly present in a tethered conformation on the cell surface. Binding of ligand, including epidermal growth factor, transforming growth factor a, epiregulin, amphiregulin, β-cellulin, and heparin-binding epidermal growth factor, stabilizes an open conformation of the receptor. Resultant dimerization enables kinase activation and phosphorylation of the intracellular domain. Phosphorylation sites enable docking of adaptor proteins that initiate signaling cascades such as the mitogen-activated protein kinase pathway activated by Ras and Shc, the Akt pathway activated by phosphatidylinositol-3-OH kinase, and the protein kinase C pathway activated by phospholipase Cγ. These pathways form a complex signaling network that impacts multiple cellular processes including differentiation, migration, and growth (Yarden and Sliwkowski, *Nat. Rev. Mol, Cell. Biol.*, 2:127-137, 2001). Activated EGFR is endocytosed within several minutes and a fraction undergoes fast recycling from the early endosome. The alternate fraction persists to the late endosome resulting in slower recycling or degradation (Sorkin and Goh, *Experimental Cell Research.*, 315:683-696, 2009).

Dysregulation of EGFR-mediated signalling is observed in breast, bladder, head and neck, and non-small cell lung cancers (Yarden and Sliwkowski, *Nat. Rev. Mol. Cell. Biol.*, 2:127-137, 2001). Accordingly, the present antibody-based constructs, including bi- and trispecific antibodies that target the EGFR, can be used to treat these cancers.

An analysis of 15 years of published literature on EGFR expression and cancer prognosis revealed that receptor overexpression is associated with reduced survival in 70% of head and neck, ovarian, cervical, bladder, and esophageal cancers (Nicholson et al., *Eur. J. Cancer*, 37 Suppl. 4, S9-15, 2001). Autocrine production of transforming growth factor a and epidermal growth factor (EGF) correlate with reduced survival in lung cancer (Tateishi et al., *Cancer Research*, 50:7077-7080, 1990). Receptor mutation is also implicated in cancer. EGFRvIII, which lacks amino acids 6-273, is observed in glioblastoma, non-small cell lung cancer, and cancers of the breast and ovary (Pedersen et al., *Ann. Oncol.*, 12:745-760, 2001). This mutant is unable to bind ligand yet is constitutively active, posing a unique therapeutic challenge, particularly for ligand blocking agents. Ectodomain point mutants in glioblastoma yield tumorigenicity (Lee et al., *PLoS. Med.*, 3:e485, 2006). Kinase domain mutations observed in non-small cell lung cancer hyperactivate kinase (Sharma et al., *Nat. Rev. Cancer*, 7:169-181, 2007).

As a result of the involvement of EGFR in cancer, there has been substantial effort spent developing receptor inhibitors as therapeutics. The U.S. Food and Drug Administration has approved two monoclonal antibodies and two tyrosine kinase inhibitors targeting EGFR. Cetuximab (Erbitux®, Bristol-Myers Squibb), approved for colorectal and head and neck cancer, and panitumumab (Vectibix®, Amgen), approved for colorectal cancer, are antibodies that compete with EGF for receptor binding. However, the relative impact of ligand competition, receptor downregulation, and antibody-dependent cellular cytotoxicity is unknown (note that panitumumab is an immunoglobulin G (IgG) 2a molecule and thus incapable of triggering cellular cytotoxicity). Both antibodies exhibit modest efficacy. In treatment of metastatic colorectal cancer refractory to irinotecan tyrosine kinase inhibitor, only 11% of patients respond to cetuximab alone and only 23% respond to cetuximab and irinotecan in combination (Cunningham et al., *N. Engl. J. Med.*, 351:337-345, 2004). In the treatment of head and neck cancer, the addition of cetuximab to radiation extends median survival from 29 to 49 months yet only increases responsiveness from 45% to 55% and improvement is only evident for oropharyngeal cancer but not hypopharyngeal or laryngeal cancers. Moreover, metastases were present at comparable amounts with and without antibody (Bonner et al., *N. Engl. J. Med.*, 354:567-578, 2006). In metastatic colorectal cancer, panitumumab extends progression-free survival from 64 days to 90 days; yet the overall response rate was only 8% and there was no improvement in overall survival (Messersmith and Hidalgo, *Clinical Cancer Research*, 13:664-4666, 2007).

While this efficacy validates EGFR as a useful therapeutic target, it begs the search for improved understanding of receptor biology and the development of improved therapy. Potential causes of the modest efficacy include inability to effectively compete with ligand, especially in the presence of autocrine signaling; insufficient downregulation of receptor; lack of inhibition of constitutively active EGFRvIII; and mutational escape. Thus, novel binders capable of downregulation and/or inhibition via different modes of action would be beneficial. Small, monovalent binders would enable improved biophysical studies via specific inhibition or Forster resonance energy transfer. Such small binders could also be useful for in vivo imaging to study receptor localization and trafficking.

In addition to the EGFR (e.g., a human EGFR) and HER2/neu as cancer targets, the antibody-based constructs can be directed to A33 (e.g., human A33 or mouse A33), and mouse CD276.

Other cancer-specific or receptor tyrosine kinases as molecular targets: Other targets include receptors of the ErbB, insulin, PDGF, FGF, VEGF, HGF, Trk, Eph, AXL, LTK, TIE, ROR, DDR, RET, KLG, RYK, and MuSK receptor families. For example, the antibody-based constructs described herein that target a VEGF receptor (e.g., VEGF-R2) can be used in the treatment of multiple myeloma. As is known in the art, receptor tyrosine kinases are also associated with psoriasis and hyperimmune responses and can therefore be targeted and treated with the present bispecific antibodies.

Nucleic acids: Nucleic acid (e.g., DNA) sequences coding for any of the polypeptides within the present antibody-based constructs are also within the scope of the present invention as are methods of making the constructs. For example, variable regions can be constructed using PCR mutagenesis methods to alter DNA sequences encoding an immunoglobulin chain, e.g., using methods employed to generate humanized immunoglobulins (see e.g., Kanunan, et al., *Nucl. Acids Res,* 17:5404,1989; Sato, et al., *Cancer Research* 53:851-856, 1993; Daugherty, et al., *Nucleic Acids Res.* 19(9):2471-2476,1991; and Lewis and Crowe, *Gene* 101:297-302, 1991). Using these or other suitable methods, variants can also be readily produced. In one embodiment, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

The methods of generating antibody-based constructs can be carried out using standard techniques known in the art. For example, one can use standard methods of protein expression (e.g., expression in cell culture with recombinant vectors) followed by purification from the expression system. In some circumstances (e.g., to produce a given domain, linker, or tag), chemical synthesis can also be used. These methods can be used alone or in combination to produce constructs having one or more of the sequences described in detail herein (e.g., one or more of the functional sequences delineated in the constructs of FIGS. 10-13) as well as constructs including sequences that differ from those proteins but that retain one or more functions (e.g., the ability to specifically bind a molecular target such as a tyrosine kinase receptor).

More specifically, to produce a heavy or light chain of a tetrameric immunoglobulin or an scFv, an accessory sequence, a linker, or any other component of the constructs described herein, nucleic acid sequences encoding the desired polypeptide can be ligated into an expression vector and used to transform a prokaryotic cell (e.g., bacteria) or transfect a eukaryotic (e.g., insect, yeast, or mammal) host cell. In general, nucleic acid constructs can include a regulatory sequence operably linked to a nucleic acid encoding the immunoglobulin chains or a portion thereof. Regulatory sequences (e.g., promoters, enhancers, polyadenylation signals, or terminators) can be included as needed or desired to affect the expression of a nucleic acid sequence. The transformed or transfected cells can then be used, for example, for large or small scale production of the engineered protein by methods well known in the art. In essence, such methods involve culturing the cells under conditions suitable for production of the engineered protein and isolating the protein from the cells or from the culture medium. Additional guidance can be obtained from the Examples presented below.

The antibody-based constructs described herein can be administered directly to a mammal. Generally, the constructs can be suspended in a pharmaceutically acceptable carrier (e.g., physiological saline or a buffered saline solution) to facilitate their delivery. Encapsulation of the polypeptides in a suitable delivery vehicle (e.g., polymeric microparticles or implantable devices) may increase the efficiency of delivery. Compositions can be made by combining any of the antibody-based constructs provided herein with a pharmaceutically acceptable carrier. Such carriers can include, without limitation, sterile aqueous or non-aqueous solutions, suspensions, and emulsions. Examples of non-aqueous solvents include mineral oil, propylene glycol, polyethylene glycol, vegetable oils, and injectable organic esters. Aqueous carriers include, without limitation, water, alcohol, saline, and buffered solutions. Preservatives, flavorings, and other additives such as, for example, antimicrobials, anti-oxidants (e.g., propyl gallate), chelating agents, inert gases, and the like may also be present. It will be appreciated that any material described herein that is to be administered to a mammal can contain one or more pharmaceutically acceptable carriers. In particular embodiments, the antibody-based constructs of the invention are formulated in the same manner as a commercially developed antibody, including cetuximab and others described above.

The pharmaceutical formulations described herein can be administered to any part of the host's body for subsequent delivery to a target cell. A composition can be delivered to, without limitation, the brain, the cerebrospinal fluid, joints, nasal mucosa, blood, lungs, intestines, muscle tissues, skin, or the peritoneal cavity of a mammal. In terms of routes of delivery, a composition can be administered by intravenous, intracranial, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinician. Suitable dosages are in the range of 0.01-1,000 µg/kg. Wide variations in the needed dosage are to be expected in view of the variety of cellular targets and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the antibody-based constructs in a suitable delivery vehicle (e.g., polymeric microparticles or implantable devices) may increase the efficiency of delivery.

As is known in the art, dosage may vary based on the condition to be treated. One of ordinary skill in the art wishing to use an antibody-based construct (e.g., a bi- or trispecific antibody) of the present invention can obtain information and guidance regarding dosage from currently available antibody therapeutics. For example, cetuximab, when used for the treatment of colorectal cancer in adults is delivered IV at 400 mg/m$^2$ as an initital loading dose administered as a 120-min infusion (max rate of infusion, 10 mg/min). The weekly maintenance dose is 250 mg/m² infused over 60 min (max rate of infusion, 10 mg/min) until disease progression or unacceptable toxicity. For treatment of squamous cell carcinoma of the head and neck, in adults, the recommended delivery for cetuximab is IV in combination with radiation therapy. The recommended dose is 400 mg/m² as a loading dose given as a 120-min infusion (max rate of infusion, 10 mg/min) 1 wk prior to initiation of a course of radiation therapy. The recommended weekly maintenance dose is 250 mg/m² infused over 60 min (max rate of infusion, 10 mg/min) weekly for the duration of radiation therapy (6 to 7 wk). Ideally, administration should be complete 1 hour prior to radiation therapy. As a single agent, the recommended initial dose is 400 mg/m² follwed by 250 mg/m² weekly (max infusion rate, 10 mg/min) until disease progression or unacceptable toxicity.

With respect to therapeutic indications, we envision the antibody-based compositions of the invention, including the constructs such as the BS28 constructs described in the Examples, in use as targeted therapeutics in multiple forms of cancer. Although 806 specifically targets EGFRvIII, our in vitro data suggests that BS28 will be effective on a wide range of cancer cell lines with varied wild-type and mutant receptor densities. Also, the efficacy observed at a low dose of bispecific antibody in mouse models indicates that we may improve upon the 400 mg/m² standard intravenous dose of cetuximab (cetuximab dosing information). Accordingly, methods of treatment using doses less than those recommended for cetuximab are within the scope of the present invention. The patient treated may have, or the medicament prepared may be useful in, breast cancer, bladder cancer, lung cancer, including non-small-cell lung cancer, colorectal cancer, squamous-cell carcinoma of the head and neck, ovarian cancer, cervical cancer, esophageal cancer, salivary gland cancer, gastric cancer, a B cell cancer, multiple myeloma, thyroid cancer, a glioblastoma, or pancreatic cancer.

The duration of treatment with any composition provided herein can be any length of time from as short as one day to as long as the life span of the host (e.g., many years). For example, an engineered protein can be administered once a week (for, for example, 4 weeks to many months or years); once a month (for, for example, three to twelve months or for many years); or once a year for a period of five years, ten years, or longer. It is also noted that the frequency of treatment can be variable. For example, the present bispecific antibodies can be administered once (or twice, three times, etc.) daily, weekly, monthly, or yearly.

An effective amount of any composition provided herein can be administered to an individual in need of treatment. The term "effective" as used herein refers to any amount that induces a desired response while not inducing significant toxicity in the patient. Such an amount can be determined by assessing a patient's response after administration of a known amount of a particular composition. In addition, the level of toxicity, if any, can be determined by assessing a patient's clinical symptoms before and after administering a known amount of a particular composition. It is noted that the effective amount of a particular composition administered to a patient can be adjusted according to a desired outcome as well as the patient's response and level of toxicity. Significant toxicity can vary for each particular patient and depends on multiple factors including, without limitation, the patient's disease state, age, and tolerance to side effects.

In any of the methods of treatment, the subject can be a human and the method can include a step of identifying a patient for treatment (e.g., by performing a diagnostic assay for a cancer). Further, one may obtain a biological sample from a patient and expose cancerous cells within the sample to one or more bispecific antibodies ex vivo to determine whether or to what extent the antibodies downregulate a target expressed by the cells or inhibit their proliferation or capacity for metastasis. Similarly, one may obtain a biological sample from a patient and expose cancerous cells within the sample to one or more of the bispecific antibodies that have been engineered to carry toxic cargo. Evaluating cell survival or other parameters (e.g., cellular proliferation or migration) can yield information that reflects how well a patient's cancer may respond to in vivo treatment with the engineered protein tested in culture. The patient identified as a candidate for treatment with the present antibodies may be one who is resistant to treatment with a conventional tetrameric immunoglobulin (e.g., cetuximab).

Any method known to those in the art can be used to determine if a particular response is induced. Clinical methods that can assess the degree of a particular disease state can be used to determine if a response is induced. The particular methods used to evaluate a response will depend upon the nature of the patient's disorder, the patient's age, and sex, other drugs being administered, and the judgment of the attending clinician.

As noted above, the antibody-based constructs can also be used as delivery agents to deliver cargo (e.g., a therapeutic or imaging agent) to a particular cell type. The cargo can be internalized by virtue of internalization of the engineered protein and its target molecule. The cargo can be a cytotoxic agent, which refers to a substance that inhibits or prevents the function of cells and/or causes destruction of cells. Cytotoxic agents include radioactive isotopes (e.g., $^{131}$I, $^{125}$I, $^{90}$Y and $^{186}$Re), chemotherapeutic agents, and toxins such as enzymatically active toxins of bacterial, fungal, plant or animal origin or synthetic toxins, or fragments thereof. The agents can also be non-cytotoxic, in which case they will not inhibit or prevent the function of cells and/or will not cause destruction of cells. A non-cytotoxic agent may include an agent that can be activated to be cytotoxic. A non-cytotoxic agent may include a bead, liposome, matrix or particle (see, e.g., U.S. Patent Publications 2003/0028071 and 2003/0032995 which are hereby incorporated by reference herein in their entireties). Such agents may be conjugated, coupled, linked or otherwise associated with an engineered protein disclosed herein.

Kits: The polyspecific antibodies (e.g., bispecific and trispecific antibodies) described herein, domains thereof, nucleic acids, including vector constructs that can be used to produce them, and any of the other compositions of the invention can be packaged in various combinations as a kit, together with instructions for use.

The studies described in the examples below illustrate the compositions and methods of the invention without limitation.

EXAMPLES

In the studies described below, bispecific antibodies were designed using a modular format that fused the full 225 mAb with the 806 single chain variable fragment (scFv). These bispecific compounds were designated BS28 followed by their conformational specificity, as depicted in FIG. 1. The constructs include a full human IgG1 backbone with the 225 variable domains with an 806 scFv conjugated to either the light chain or heavy chain at the N or C terminal ends. As shown in FIG. 1, BS28 constructs are bispecific and tetravalent.

The bispecific antibodies were secreted from HEK 293F cells (Invitrogen) co-transfected with the appropriate heavy and light chain expression plasmids derived from the gWiz vector (Genlantis). The sequences for the four bispecific plasmids illustrated in FIG. 1 are provided in Appendix A. All constructs include a Kozak consensus sequence immediately upstream of the leader sequence to enhance yield (Kozak, Nature, 269:391-394, 1977). Although not essential, our modular bispecific format allows for the insertion of an epitope tag (such as cmyc in the case of BS28-LC) to facilitate labeling and/or purification.

For the preparation of each bispecific construct, one transfected chain was conjugated to an scFv of the 806 antibody and the other transfected chain was identical to the unmodified 225 antibody. Cells were grown in Freestyle medium (Invitrogen) and transfection was performed in the presence of 2 μg/mL polyethylinimine (Sigma-Aldrich) and 4% OptiPro® medium (Invitrogen). Following transfection, cells were incubated for 7 days at 37° C. and 5% $CO_2$. Secretions were then harvested, purified via protein A affinity chromatography (Pierce), and reconstituted in phosphate buffered saline (PBS). Yields ranged from 2-1383 μg/L depending on antibody format and the fibronectin clone used; HN secretes best (1383 μg/L), followed by LC (305 μg/L), HC (125 μg/L), and LN (4 μg/L).

The secreted constructs were analyzed by sodium dodecyl sulfate polyacrylamide gel electrophoresis (SDS-PAGE) to ensure that all bispecific antibodies were fully assembled and free of contaminants, The preparations were pure; all antibodies were fully assembled under non-reducing conditions and reduced to heavy and light chains of the expected molecular weights under reducing conditions. BS28-LN was not secreted in sufficient quantities to visualize via SDS-PAGE. The molecular weights of all four constructs are presented in the Table below. Note that the bispecific antibodies are approximately 1.3 times the size of the 225 mAb,

| Antibody Construct | Heavy Chain MW (g/mol) | Light Chain MW (g/mol) | Full Antibody MW (g/mol) |
|---|---|---|---|
| 225 | 51082 | 25629 | 153422 |
| BS28-HN | 77218 | 25629 | 205640 |
| BS28-HC | 77634 | 25629 | 206471 |
| BS28-LN | 51082 | 52423 | 206955 |
| BS28-LC | 51082 | 53510 | 209129 |

Figure 2:
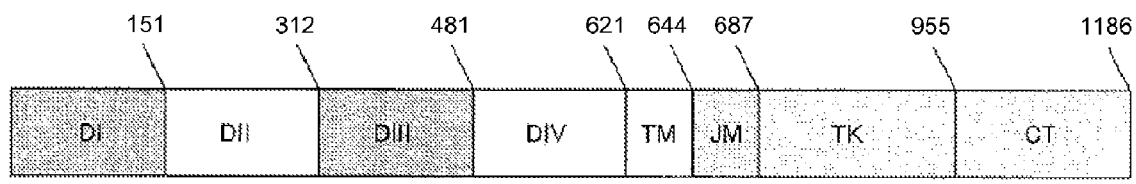
FIG. 2 is a schematic of the extracellular, transmembrane, and intracellular domains of EGFR.

The crystal structures of the EGFR extracellular domain in both the tethered monomeric and active dimeric conformations have been solved (Li et al., Cancer Cell, 7:301-311, 2005); (Ogiso et al., Cell, 110:775-787, 2002) and reveal that domains 1 and 3 are involved in maintaining the tethered conformation while domain 2 mediates dimerization. Domain 4 is disordered and cannot be crystallized, but may also play a role in receptor dimerization. Native ligands such as EGF and TGF-α bind to domain 3 of the ectodomain. The 225 antibody binds to domain 3 of the EGFR extracellular domain and obstructs ligand binding (Li et al., Cancer Cell, 7:301-311, 2005). The 806 antibody was raised against the junctional peptide at the tail end of EGFR extracellular domain 2 and is noncompetitive with both ligand and 225. This epitope is only exposed in the wild type receptor when it is in the activated state but which is constitutively exposed in the truncation mutant of EGFR known as EGFRvIII, which deletes all of domain 1 and the majority of domain 2 of the EGFR ectodomain (Garrett et al., Proc. Natl. Acad. Sci. USA, 106:5082-5087, 2009). A schematic of EGFR is provided in FIG. 2. Domains 1 and 3 are involved in ligand binding and domains 2 and 4 facilitate dimerization. Crystal structures of EGFR in its tethered and activated states are available in the art (Burgess et al., Mol. Cell, 12:541-552, 2003). EGF (or another native ligand) gates the transition between the tethered and the active conformation. The epitopes of 225 and 806 identified from crystal structures of EGFR bound to the respective Fabs are known, and residues implicated in the epitopes of EGF, 225, and 806 are identified in the Table below. Note that the epitopes are non-overlapping and 225 is competitive with ligand, while 806 is not.

| Protein | EGFR Binding Domain | Epitope |
|---|---|---|
| mAb 225 | III | Q384, Q408, H409, K443, K465, I467, N473 |
| mAb 806 | II | C287, E293, D297, G298, V299, R300, K301, C302 |

Figure 3:
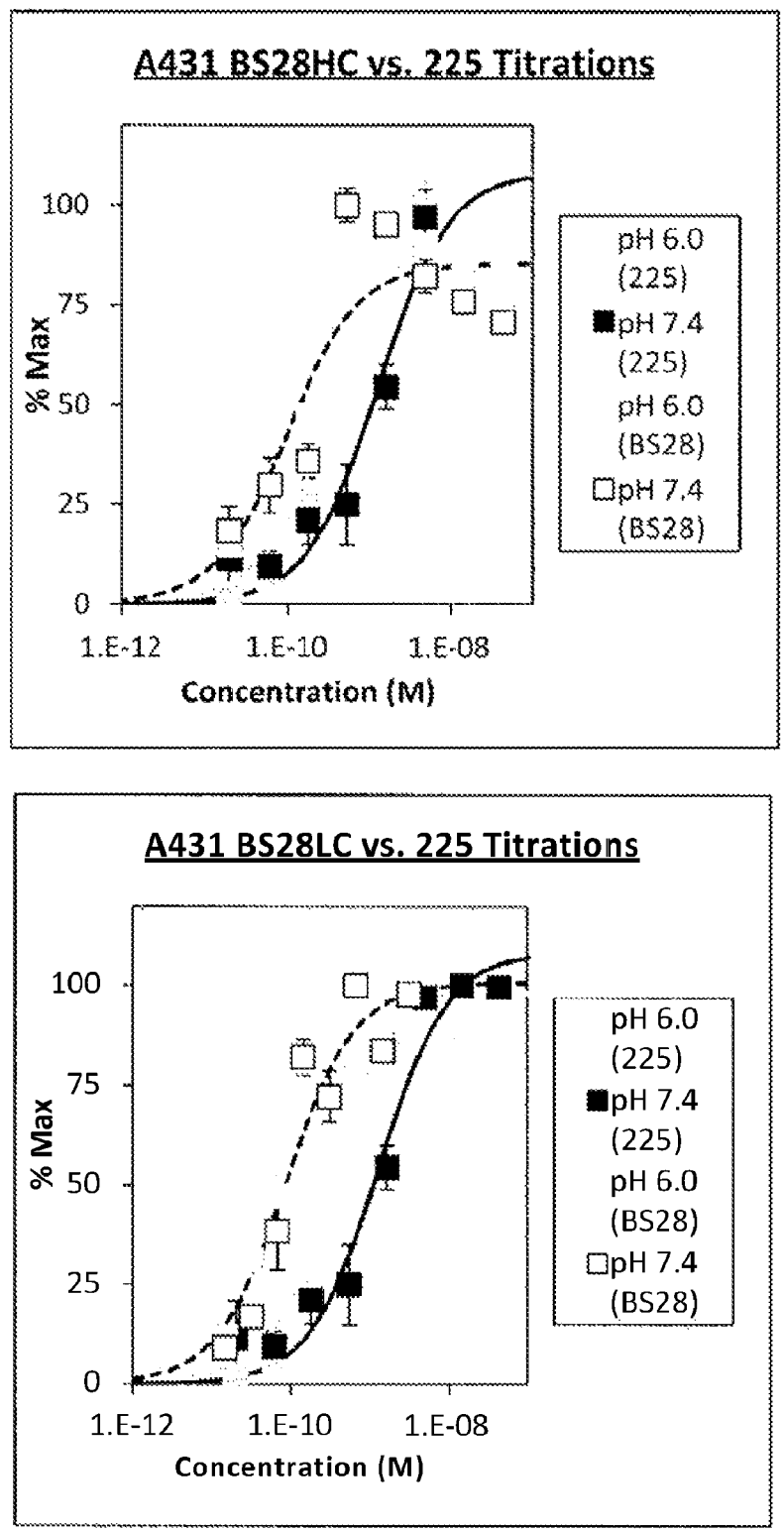
FIG. 3 is a pair of graphs illustrating BS28 binding kinetics. Due to avidity effects that emanate from the bispecificity of BS28 constructs, both BS28-HC and BS28-LC have a higher affinity for their target antigen, EGFR, than the unmodified 225 antibody. The unconjugated 225 antibody (closed symbols) and the BS28 constructs (open symbols) were titrated on the surface of A431 epidermoid carcinoma cells at pH 6.0 (gray) and pH 7.4 (black). Nonlinear least squares regression fits' are shown for 225 (solid lines) and BS28 constructs (dashed lines) at pH 6.0 (gray) and pH 7.4 (black). Using nonlinear least squares regression, the titration curves were fitted to binding isotherms (% bound=[L]/([L]+$K_d$ where [L] is antibody concentration and $K_d$ is the equilibrium dissociation constant) and the equilibrium dissociation constants were determined. Compared to unmodified 225 mAb, the bispecific constructs have four-to-six-fold tighter interactions with EGFR at pH 6.0 and greater than tenfold tighter interactions with EGFR at pH 7.4.

The interaction between two of the bispecific constructs (BS28-HC and BS28-LC) and their target antigen, EGFR, was characterized on the surface of A431 cells. As shown in FIG. 3 and the Table below, the affinity of the Ab-Fn3 fusion is 4-6 times greater than that of the unmodified 225 antibody at endosomal pH (6.0) and more than ten times greater than that of the unmodified 225 antibody at physiological pH (7.4). This is a direct consequence of avidity effects resulting from the bispecificity of the BS28 construct. The insensitivity of binding to pH reduction indicates that the compound will remain bound to EGFR following internalization.

| Construct | $K_d$ (pH 6.0, pM) | $K_d$ (pH 7.4, pM) |
|---|---|---|
| 225 | 370 | 1284 |
| BS28-HC | 97 | 100 |
| BS28-LC | 59 | 86 |

The bispecific construct we have developed may offer numerous therapeutic advantages over current clinically available treatments. The strategy of using a bispecific antibody with two variable domains targeting non-overlapping epitopes on a single receptor tyrosine kinase can also be generalized as a robust therapeutic option. At least one of the epitopes can be exposed when the receptor is in an activated state and/or it can be present in a mutant form that increases a patient's risk for disease or facilitates the disease process. This targeting strategy has the potential to complement existing therapeutic mechanisms (namely ligand competition, immune recruitment, and angiogenesis inhibition) to enhance drug efficacy via clustering, receptor downregulation, increased binding affinity, and selective targeting of mutant or activated receptors. The therapeutic promise of our bispecific antibodies has been confirmed both in vitro through surface EGFR downregulation assays on human cells and in vivo via mouse xenograft studies.

Figure 4:
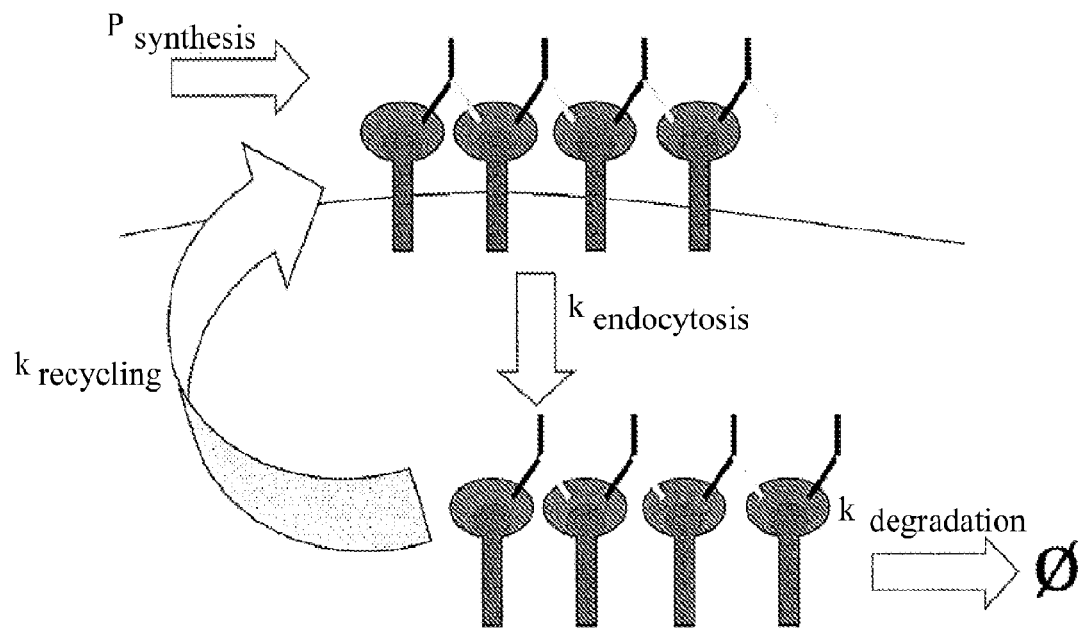
FIG. 4 is a schematic representation of bispecific antibody-induced clustering. EGFR trafficking following incubation with a bispecific antibody is depicted with the relevant kinetic parameters labeled. Treatment with a bispecific antibody that binds two non-competitive epitopes of its target receptor may induce linear or circular chains of crosslinked receptor on the cell surface. This has been shown to inhibit receptor recycling, thus reducing the amount of surface receptor available for signal transduction.

As shown in FIG. 4, the presence of two non-competitive EGFR binding moieties on the same molecular species enables receptor crosslinking and clustering. Clustering has been shown to abrogate EGFR recycling, thereby decreasing surface receptor expression and activation of downstream signaling pathways (Spangler et al., Proc. Natl. Acad. Sci. USA, 107:13252-13257, 2010). By altering the trafficking of EGFR using the endogenous endocytic machinery, clustering reduces the steady state surface levels of EGFR, thus reducing the number of receptors available for signal activation. Importantly, receptor clustering is not agonistic, achieving downregulation without activating downstream pathways (Spangler et al., *Proc. Natl. Acad. Sci. USA,* 107:13252-13257, 2010).

Figure 5:
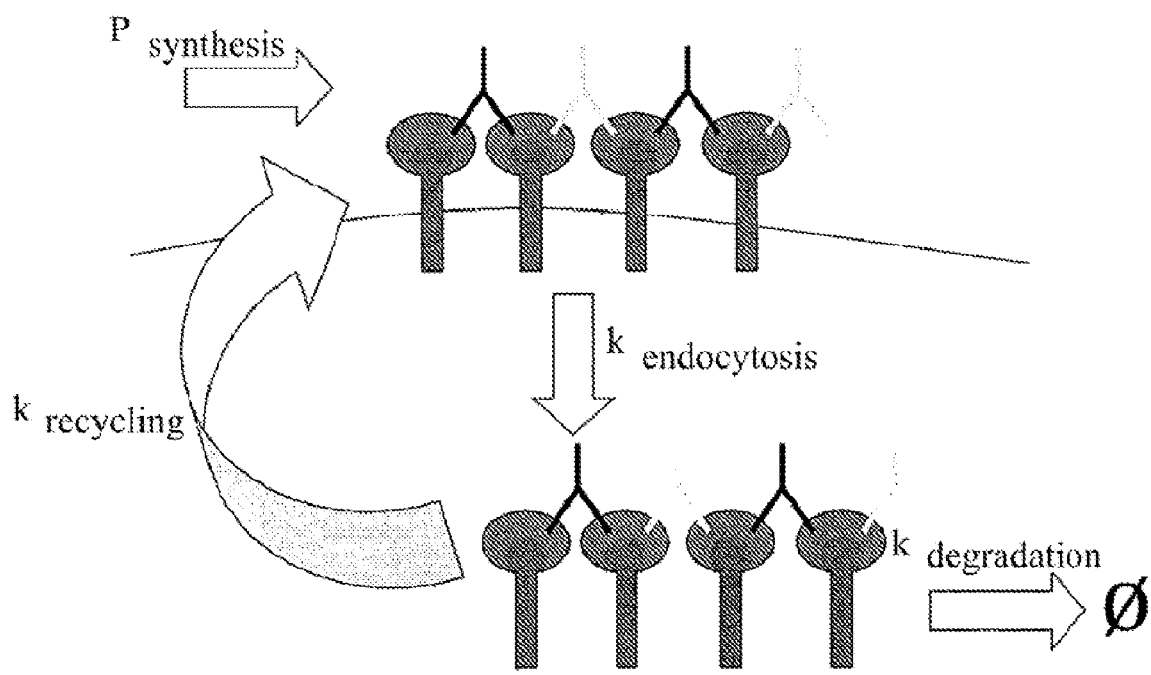
FIG. 5 is a schematic representation of combination antibody-induced clustering. EGFR trafficking following incubation with two noncompetitive antibodies (shown in black and gray) is depicted with the relevant kinetic parameters labeled. Treatment with antibodies that bind to distinct epitopes on the target receptor may induce linear or circular chains of crosslinked receptor on the cell surface. This has been shown to inhibit receptor recycling, thus reducing the amount of surface receptor available for signal transduction.

Receptor clustering can be induced by using a combination of antibodies with non-overlapping epitopes. However, this requires alternating receptor binding, as shown in FIG. 5. The advantage of the bispecific antibody is that every molecule displays both paratopes, reducing transport limitations and facilitating receptor crosslinking, since every antibody molecule is capable of extending the growing receptor-antibody chain.

Bispecific constructs also have enhanced binding compared to monoclonal antibodies, as shown in FIG. 3. This is the result of a phenomenon known as avidity, which describes the cooperativity of binding. The presence of multiple antibody interactions increases the probability of binding and reduces the probability of dissociation since the likelihood of multiple interactions terminating simultaneously is low. Furthermore, if one paratope of the tetravalent antibody dissociates from the receptor, three other paratopes may remain bound to receptor, thus tethering the antibody and increasing the local concentration of the free paratope in the vicinity of surface-bound receptor. In all likelihood, the dissociated paratope will rebind, strengthening the apparent affinity of the antibody for its target receptor. In the specific case of the 225-806 bispecific construct, binding is not only enhanced, but enabled through avidity effects. Recall that the 806 epitope is only exposed when EGFR is in its active conformation. However, due to random fluctuations of the receptor, the 806 epitope is exposed at times. If the 225 paratope is already bound to EGFR, the range of the 806 paratope is constrained, increasing the apparent concentration of 806 paratope to which the receptor is exposed and increasing the likelihood that 806 will bind when its epitope is exposed. Thus, the 806 paratope on the bispecific antibody is much more likely to capture its epitope in the 225-bound constrained state compared to the unconstrained state in free solution. Improved 806 binding in the bispecific state is evidenced by the affinity enhancement of BS28 constructs compared to mAb 225 in A431 cells at pH 7.4 (physiological pH). The 806 monoclonal antibody only binds to approximately 10% of EGFR in A431 cells (the activated fraction), yet in a bispecific construct with 225, it improves the affinity of the monoclonal 225 antibody by more than an order of magnitude. This improved 806 scFv binding also facilitates crosslinking, thus enhancing receptor clustering.

Improved receptor clustering manifests itself through enhanced surface EGFR downregulation. We therefore performed downregulation assays on a variety of EGFR-expressing cell lines with diverse cancerous and non-cancerous origins. The cell lines that were studied are listed in order of total EGFR expression level (measured by quantitative flow cytometry) in the Table below. Note that the U87-SH line expresses both wild type and EGFRvIII receptors.

| Cell Line | Origin | EGFR per Cell |
|---|---|---|
| HT-29 | Colorectal adenocarcinoma | $1.0 \times 10^5$ |
| Hela | Cervical adenocarcinoma | $1.7 \times 10^5$ |
| U87 | Glioblastoma | $1.9 \times 10^5$ |
| HMEC | Human mammary epithelial tissue | $4.5 \times 10^5$ |
| CHO-EG | Chinese hamster ovary (EGFR-GFP transfected) | $1.6 \times 10^6$ |
| U87-SH | Glioblastoma (mutant EGFRvIII transfected) | $1.7 \times 10^6$ |
| A431 | Epidermoid carcinoma | $2.8 \times 10^6$ |

Surface EGFR densities as measured by quantitative flow cytometry are indicated. Note that these cell lines span wide range of normal and transformed mammalian origins.

Figure 6:
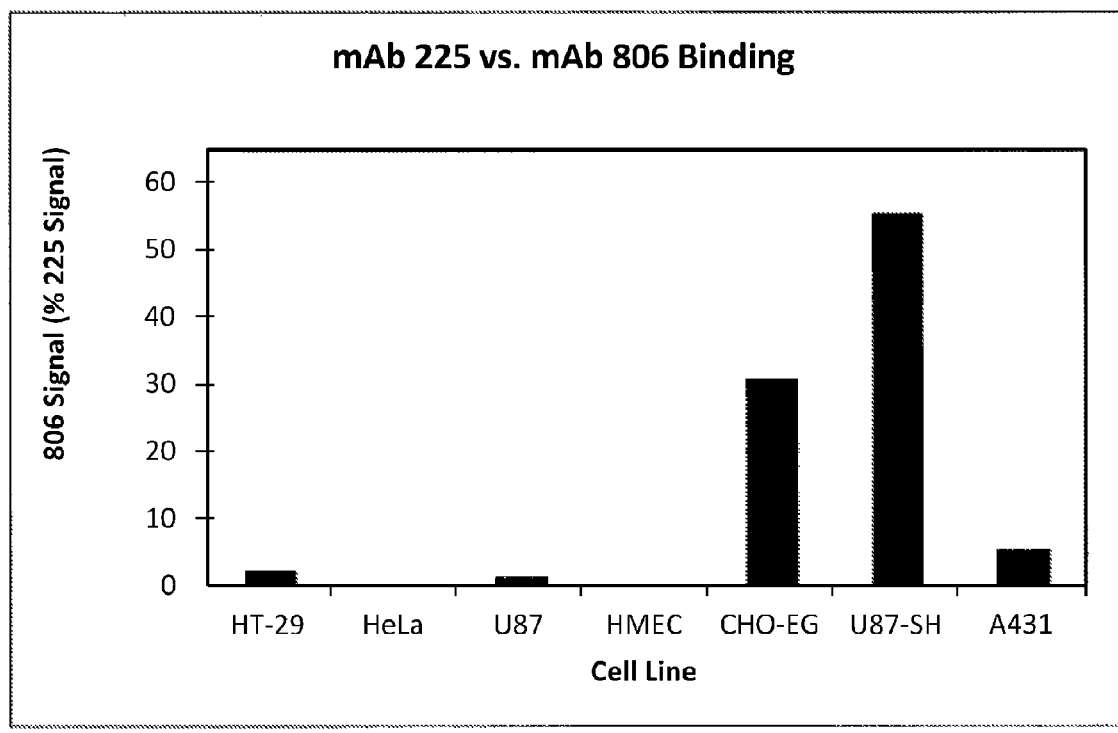
FIG. 6 is a bar graph illustrating relative binding of mAb 225 and mAb 806 as determined by flow cytometry in the seven EGFR-expressing cell lines tested for BS28-induced downregulation. Saturating concentrations (20 nM) were added of both mAbs. Note that 806 binding is weak in all cell lines with the exception of the EGFR-transfected CHO-EG line (in which the EGFR may be differentially folded) and the EGFRvIII-transfected U87-SH cell line.

Since the 806 epitope is only exposed in the mutant or activated form of EGFR, mAb 806 binding is negligible in all cell lines that were examined with the exception of CHO-EG (in which the receptor may be folded differently than in cell lines that natively express EGFR) and U87-SH, which stably expresses tenfold more mutant EGFRvIII receptors than wild type EGFR receptors. mAb 806 binding relative to that of mAb 225 is depicted in FIG. 6.

Figure 7:
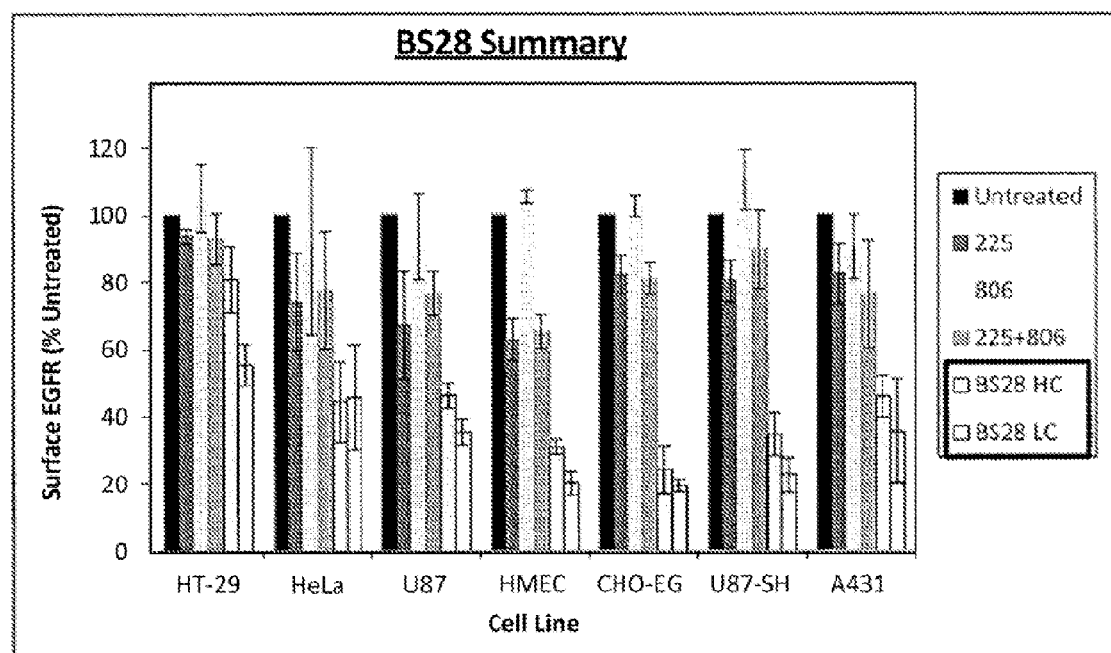
FIG. 7 is a bar graph illustrating surface EGFR downregulation following BS28 treatment. The seven EGFR expressing cell lines listed (shown in increasing order of EGFR expression) were treated with the indicated antibodies (20 nM) for 13 hours at 37° C. They were then acid stripped, labeled with an anti-EGFR antibody and a fluorophore-conjugated secondary antibody, and analyzed via flow cytometry to quantify remaining surface receptor relative to that of untreated cells. Note that mAb 225, mAb 806, and the combination thereof do not significantly affect steady-state EGFR surface levels, whereas BS28-HC and BS28-LC (boxed) decrease surface EGFR expression by 60-80% in all tested cell lines.

To determine whether BS28 constructs induce EGFR downregulation, cells were treated with 20 mM mAb 225, mAb 806, mAbs 225 and 806 combined, BS28-HC, or BS28-LC for 13 hours at 37° C. This allowed the receptors to achieve a new steady state in the presence of antibody. Cells were then acid stripped to remove surface antibody, relabeled with an anti-EGFR antibody followed by a fluorophore-conjugated secondary antibody, and quantified via flow cytometry. For each of the seven cell lines tested, single or combination mAbs had minimal effects, whereas BS28-HC and BS28-LC reduced surface receptors 60-80% (FIG. 7). While both BS28 constructs reproducibly effected downregulation, BS28-LC was slightly more potent than BS28-HC. The downregulation results are suggestive of greatly enhanced receptor clustering in the presence of the bispecific antibody compared to mAb 225, mAb 806, or a combination thereof.

To demonstrate the advantage of using a bispecific construct that includes mAb 806 to target mutant receptors, we measured surface EGFR downregulation in a series of cell lines derived from the U87 glioblastoma line that are transfected with various numbers of EGFRvIII (Huang et al., *Proc. Natl. Acad. Sci. USA,* 104:12867-12872, 2007; Huang et al., *J Biol. Chem.,* 272:2927-2935, 1997). The wild type EGFR and EGFRvIII densities of each cell lines are provided in the Table below. Note that the U87-DK (dead kinase) cell line is transfected with EGFRvIII possessing the K721M mutation, which is known to inactivate the tyrosine kinase domain (Huang et al., *J Biol Chem,* 272:2927-2935, 1997), and the U87-wt (wild type) line is transfected with wild type EGFR (Huang et al., *Proc. Natl. Acad. Sci. USA,* 104:12867-12872, 2007).

| Cell Line | wtEGFR/cell | EGFRvIII/cell | Total EGFR/cell |
|---|---|---|---|
| U87 | $1.9 \times 10^5$ | — | $1.9 \times 10^5$ |
| U87-M | $1.9 \times 10^5$ | $5.0 \times 10^5$ | $6.9 \times 10^5$ |
| U87-DK | $1.9 \times 10^5$ | $8.1 \times 10^5$ | $1.0 \times 10^6$ |
| U87-H | $1.9 \times 10^5$ | $1.1 \times 10^6$ | $1.3 \times 10^6$ |
| U87-SH | $1.9 \times 10^5$ | $1.4 \times 10^6$ | $1.6 \times 10^6$ |
| U87-wt | $1.9 \times 10^6$ | — | $1.7 \times 10^6$ |

The six U87-derived cell lines listed were used in surface EGFR downregulation assays. Wild type and mutant EGFR surface densities as measured by quantitative flow cytometry are indicated. M=medium, H=high, SH=super high, wt=wild type, DK=dead kinase (Huang et al., *Proc. Natl.*

*Acad. Sci. USA*, 104:12867-12872, 2007); (Huang et al., *J. Biol. Chem.*, 272:2927-2935, 1997).

Figure 8:
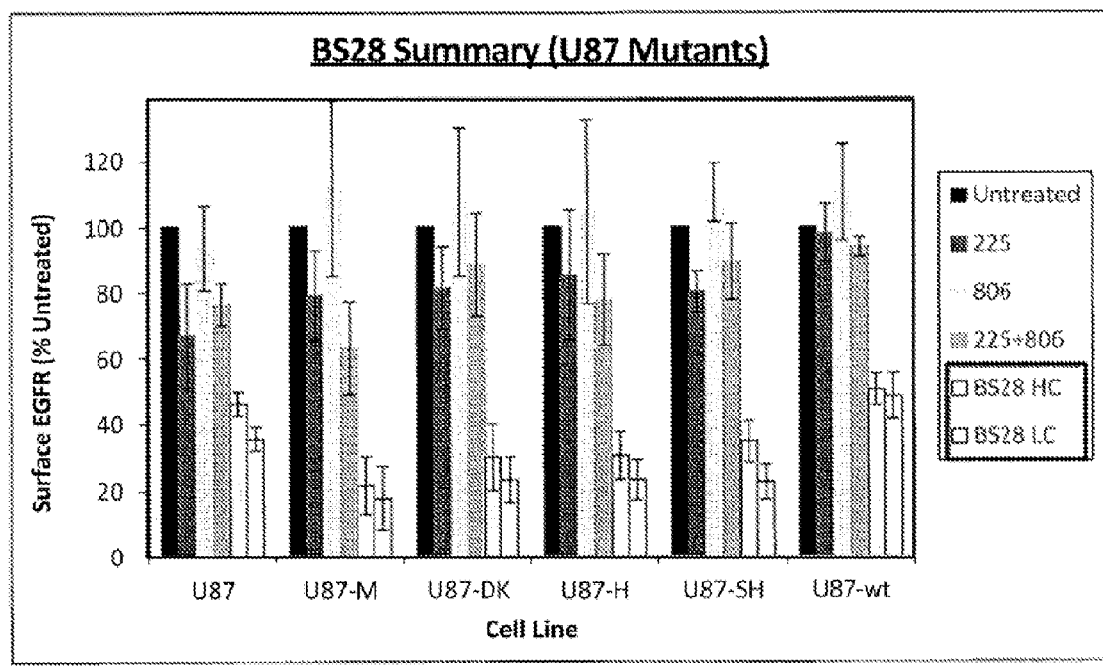
FIG. 8 is a bar graph illustrating surface EGFR downregulation in U87-derived cells following BS28 treatment. The six U87-derived cell lines listed (shown in increasing order of EGFR expression) were treated with the indicated antibodies (20 nM) for 13 hours at 37° C. They were then acid stripped, labeled with an anti-EGFR antibody and a fluorescent secondary antibody, and analyzed via flow cytometry to quantify remaining surface receptor relative to that of untreated cells. As shown, mAb 225, mAb 806, and the combination thereof do not significantly impact steady-state EGFR surface levels, whereas BS28-HC and BS28-LC (boxed) reduce surface EGFR expression by 60-80% in all examined cell lines.

As was the case for wild type EGFR-expressing cell lines, the U87-derived EGFRvIII-expressing cell lines were virtually unaffected by mAb 225, mAb 806, and the combination thereof, but profoundly impacted by both BS28-HC and BS28-LC. BS28 constructs elicited 60-80% downregulation of total (wild type plus mutant) surface EGFR on all six cell lines that were assessed (FIG. 8). Once again, BS28-LC was slightly more potent than BS28-HC.

The U87 series downregulation results suggest that receptor clustering occurs in the case of bispecific antibody treatment but not in the case of single or combination mAb treatment. We also find that the ability to downregulate EGFRvIII is independent of kinase activity since the kinase defective U87-DK is downregulated to the same extent as other U87-derived cell lines. This is consistent with the observation that combination antibody-induced downregulation is kinase domain independent (Friedman et al., *Proc. Natl. Acad, Sci. USA*, 102:1915-1920, 2005; Spangler et al., *Proc. Natl. Acad. Sci. USA*, 107:13252-13257, 2010).

The ability of BS28 constructs to downregulate both EGFR and EGFRvIII is significant since the two FDA-approved antibody drugs that target EGFR are ineffective against this mutant, as they rely significantly on ligand competition for therapeutic efficacy. Our results imply that BS28 would also have a therapeutic advantage in cases where EGFR ligands are overexpressed or otherwise dysregulated. Clearly, BS28 constructs have the potential to complement the effects and overcome the limitations of currently approved antibodies targeting EGFR.

Encouraged by the performance of BS28 constructs in vitro, we sought to test their therapeutic efficacy in a U87-SH mouse xenograft model. Two million U87-SH glioblastoma cells (stably expressing EGFRvIII) were injected subcutaneously into the right flanks of three cohorts of Ncr nude mice. After one week, tumors had grown to a volume of approximately 70 mm$^3$, at which point a twice weekly retro-orbital injection regimen of PBS, mAb 225 plus mAb 806, or BS28-LC was commenced. Mice were dosed at a total of 5 mg/kg with the exception of the first dose (day 8), which was 10 mg/kg. Treatments continued for 1.5 weeks and tumor volume was monitored daily with a digital caliper using the formula:

Volume=0.5×(Length)×(Width)$^2$

Figure 9:
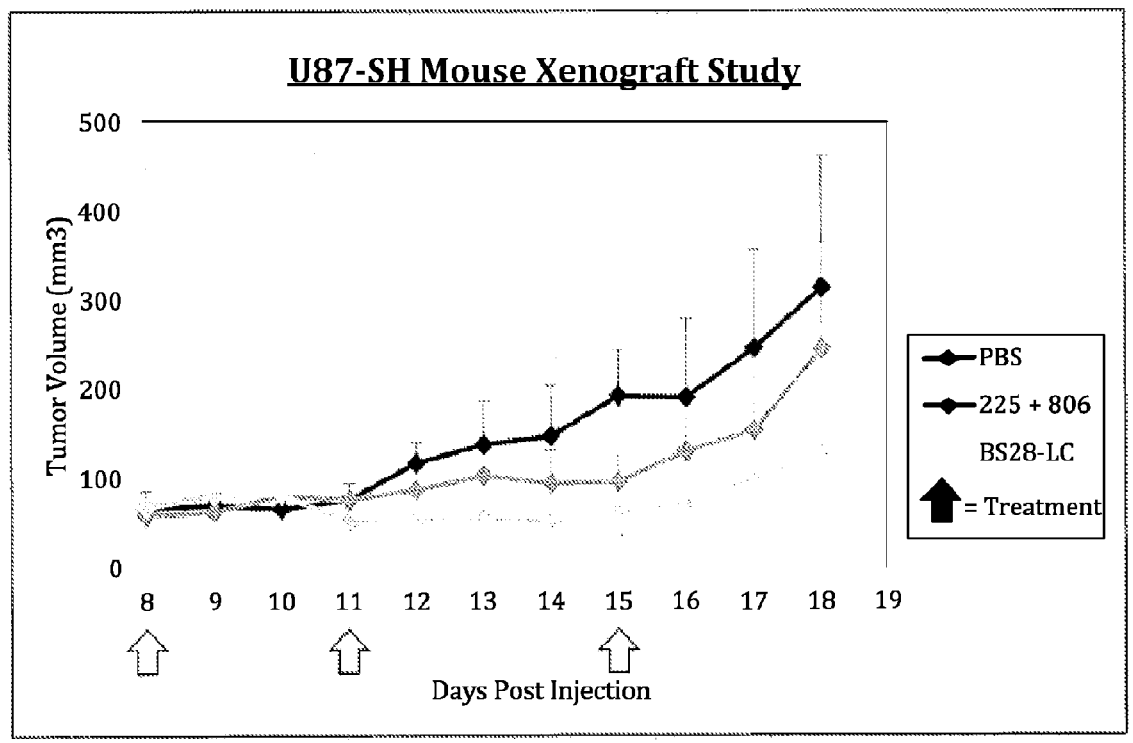
FIG. 9 is a line graph illustrating tumor inhibition in a U87-SH tumor xenograft model. Ncr nude mice were injected with 2×10$^6$U87-SH glioblastoma cells. After one week of tumor growth, mice were treated via retro-orbital injection twice weekly with PBS (black), mAbs 225 and 806 (gray), or BS28-LC (light gray). Antibodies were dosed at a total of 5 mg/kg with the exception of the initial dose, which was 10 mg/kg.

As shown in FIG. 9, the 225 and 806 mAb combination slowed tumor growth slightly compared to the saline control, whereas BS28-LC halted tumor growth through day 15 and retarded growth thereafter. Note that 5 mg/kg is a rather meager antibody dose since mAb 225 is controlling only at 50 mg/kg or greater, so the tumor response is quite impressive. The in vivo results indicate a strong therapeutic effect of BS28-LC and suggest an advantage for the bispecific antibody compared to combination treatment with its two component antibodies. The consistency with our in vitro results also hints at therapeutic efficacy of BS28 constructs on a range of cancer cell lines expressing wild type or mutant EGFR.

In addition to the therapeutic advantages of using a bispecific antibody as opposed to a single antibody or a drug cocktail, we anticipate further advantages to the development of the multispecific constructs described herein. From a logistical standpoint, combining two therapeutics into a single compound facilitates preparation and administration. Also, clinical testing of a bispecific compound may be expedited compared to a drug cocktail since one would only be required to characterize the properties of a single compound as opposed to multiple compounds. Finally, the presence of multiple antibody variable domains and the recruitment of multiple therapeutic mechanisms with a single compound along with the binding and clustering advantages of a bispecific antibody combine to make multispecific antibodies more potent than their monoclonal counterparts. As a result, drug dosage is reduced for bispecific compounds and, consequently, so are off-target effects.

Additional materials and methods used in the studies described above are presented in the following paragraphs.

Cell lines and antibodies. The transfected CHO-EG (Haugh et al., *J. Cell Sci.*, 115:303-310, 2002) and U87-derived (Johns et al., *Int. J Cancer*, 98:398-408, 2002) cell lines were established as described previously and all other lines were obtained from the American Type Culture Collection (ATCC; Manassas, Va.). Cells were maintained in their respective growth media (from the ATCC unless otherwise indicated): DMEM for A431, U87-MG, transfected U87-MG, and CHO-EG cells, McCoy's Modified 5A media for HT-29 cells, EMEM for HeLa cells, and HuMEC Ready Medium (Invitrogen, Carlsbad, Calif.) for HMEC cells. U87-MG, transfected U87-MG, and CHO-EG media were supplemented with 1 mM sodium pyruvate (Invitrogen) and 0.1 mM non-essential amino acids (Invitrogen) and transfected U87-MG lines and CHO-EG were selected with 0.3 mM Geneticin (Invitrogen). ATCC media was supplemented with 10% fetal bovine serum (FBS). 225 was secreted from the hybridoma cell line (ATCC). Unless otherwise noted, all washes were conducted in PBS containing 0.1% BSA and all mAbs were used at a concentration of 40 nM for single treatment and 20 nM each for combination treatment. EGF (Sigma, St. Louis, Mo.) was dosed at 20 nM. Trypsin-EDTA (Invitrogen) contains 0.05% trypsin and 0.5 mM EDTA.

Production of BS28 constructs via HEK cell transfection: The human IgG1 heavy and light chains of each BS28 construct were inserted into the gWiz mammalian expression vector (Genlantis). Constructs were verified by sequence analysis. HEK 293F cells (Invitrogen) were grown to 1.2 million cells per mL and diluted to one million per mL. Miniprepped DNA and polyethyleneimine (Sigma) were independently diluted to 0.05 and 0.1 mg/mL in OptiPro medium and incubated at 22° C. for 15 minutes. Equal volumes of DNA and polyethyleneimine were mixed and incubated at 22° C. for 15 minutes. 500 mL of cells and 20 mL of DNA/polyethyleneimine mixture were added to a 2 L roller bottle and incubated at 37° C., 5% CO$_2$ on a roller bottle adapter for seven days. The cell secretions were then centrifuged for 30 minutes at 15,000×g and the supernatant was filtered through a 0.22 µm bottle-top filter and purified via affinity column chromatography using protein A resin (Thermo Fisher Scientific, Waltham, Mass.). The eluted bispecific antibodies were concentrated and transferred to PBS and then characterized by sodium dodecyl sulfate polyacrylamide gel electrophoresis (SDS-PAGE) analysis.

Affinity titrations. To characterize bispecific construct binding affinities, A431 cells were trypsinized, washed in PBSA and incubated with various concentrations of Ab-Fn3 in a 96-well plate on ice. The number of cells and sample volumes were selected to ensure at least tenfold excess Ab-Fn3 relative to EGFR. Cells were incubated on ice for sufficient time to ensure that the approach to equilibrium was at least 99% complete. Cells were then washed and labeled with 66 nM PE-conjugated goat anti-human antibody (Rockland Immunochemicals, Gilbertsville, Pa.) for 20 minutes on ice. After a final wash, plates were analyzed on a FACS Calibur cytometer (BD Biosciences, San Jose, Calif.). Cell pelleting was conducted at 1000×g. The minimum and maximum fluorescence and the $K_d$ value were determined by minimizing the sum of squared errors assuming a 1:1 binding interaction (% Bound =[L]/([L]+$K_d$) where [L] is bispecific antibody concentration and $K_d$ is the equilibrium dissociation constant of the BS28 construct. Titrations were performed at both pH 6.0 (endosomal pH) and pH 7.4 (physiological pH).

mAb binding assays. To characterize mAb 225 and 806 binding to cells, the indicated cell lines were trypsinized, washed in PBSA, and incubated with 20 nM mAb 225 or 806 in a 96-well plate on ice for 1 hour. Cells were then washed and labeled with 66 nM PE-conjugated goat anti-mouse antibody (Invitrogen) for 20 minutes on ice. After a final wash, plates were analyzed on a FACS Calibur cytometer (BD Biosciences). Cell pelleting was conducted at 1000×g.

Receptor quantification. Cells were serum starved for 12-16 hours, washed, digested in trypsin-EDTA (for 20 minutes at 37° C.), neutralized with complete medium, and labeled with 20 nM 225 for 1 hour on ice. They were then washed, labeled with 66 nM phycoerythrin (PE)-conjugated goat anti-mouse antibody (Invitrogen) for 20 minutes on ice, washed again, and subjected to quantitative flow cytometry on an EPICS XL cytometer (Beckman Coulter, Fullerton, Calif.). Receptor density was calculated based on a curve of identically labeled anti-mouse IgG-coated beads (Bangs Laboratories, Fishers, Ind.).

Receptor downregulation assays. Cells were seeded at $5 \times 10^4$ per well in 96-well plates, serum starved for 12-16 hours, treated with the indicated mAbs or BS28 constructs in serum-free medium, and incubated at 37° C. for 13 hours. Subsequently, cells were washed and treated with trypsin-EDTA for 20 minutes at 37° C. Trypsin was neutralized with medium (10% FBS) and cells were transferred to v-bottom plates on ice. They were then washed, acid stripped (0.2 M acetic acid, 0.5 M NaCl, pH 2.5), and washed again prior to incubation with 20 nM 225 for 1 hour on ice to label surface EGFR. Cells were then washed and labeled with 66 nM PE-conjugated goat anti-mouse antibody (Invitrogen) for 20 minutes on ice. After a final wash, plates were analyzed on a FACS Calibur cytometer (BD Biosciences). Cell pelleting was conducted at 1000×g.

U87-SH mouse xenograft studies. Two million U87-SH glioblastoma cells (stably expressing EGFRvIII) were injected subcutaneously into the right flanks of three cohorts of Ncr nude mice. By day 8 post-injection, tumors had grown to a volume of approximately 70 mm$^3$ and a twice weekly retro-orbital injection regimen of phosphate buffered saline (PBS), mAb 225 plus mAb 806, or BS28-LC was commenced. Mice were dosed at a total of 5 mg/kg with the exception of the first bolus dose (day 8), which was 10 mg/kg. Treatments continued for 1.5 weeks and tumor volume was monitored daily with a digital caliper using the formula Volume=0.5×(Length)×(Width)$^2$. Throughout the experiment, mice were monitored for overall health and activity in accordance with Massachusetts Institute of Technology Committee on Animal Care.

What is claimed is:

1. A bispecific antibody that specifically binds a first epitope on EGFR recognized by cetuximab and specifically binds a second, non-overlapping epitope on EGFR recognized by monoclonal antibody 806 (mAb 806), wherein the bispecific antibody comprises, an IgG and a scFv, wherein the IgG comprises a heavy chain comprising the three heavy chain complementarity determining regions (CDRs) of cetuximab and a light chain comprising the three light chain CDRs of cetuximab, wherein the scFv comprises the three heavy and three light chain CDRs of mAb 806, and wherein
   (i) the scFv is fused, directly or indirectly, to the carboxy terminus of the IgG heavy chain; or
   (ii) the scFv is fused, directly or indirectly, to the carboxy terminus of the IgG light chain.

2. The bispecific antibody of claim 1, wherein the IgG is an IgG1, IgG2, IgG3 or IgG4.

3. The bispecific antibody or antigen-binding fragment of claim 2, wherein the IgG is human IgG1.

4. A pharmaceutical composition comprising the bispecific antibody or antigen-binding fragment of claim 3, and a pharmaceutically acceptable carrier.

5. The bispecific antibody or antigen-binding fragment of claim 1, wherein the IgG comprises a genetically modified variable region or a genetically modified constant region.

6. The bispecific antibody or antigen-binding fragment of claim 1, which is a chimeric, or humanized immunoglobulin.

7. The bispecific antibody or antigen-binding fragment of claim 1, further comprising an accessory protein.

8. The bispecific antibody or antigen-binding fragment of claim 7, wherein the accessory protein comprises an amino acid sequence that: prolongs the circulating half-life of the construct; facilitates isolation or purification of the construct; serves as a linker between one part of the construct and another or between the construct and another moiety; is detectable and thereby serves as a label, marker, or tag; or is cytotoxic.

9. A pharmaceutical composition comprising the bispecific antibody of claim 1, and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,464,136 B2 | Page 1 of 1 |
| APPLICATION NO. | : 13/817525 | |
| DATED | : October 11, 2016 | |
| INVENTOR(S) | : Karl Dane Wittrup et al. | |

It is certified that error appears in the above-identified patent and that said Letters Patent is hereby corrected as shown below:

In the Specification

Under the subheading CROSS-REFERENCE TO RELATED APPLICATIONS, at Column 1, Line number 8, after "application" insert -- is a 35 U.S.C. § 371 national stage filing of International Application No. PCT/US2011/048529 filed on August 20, 2011, which --

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*